US009175061B2

(12) United States Patent
Dörwald

(10) Patent No.: US 9,175,061 B2
(45) Date of Patent: Nov. 3, 2015

(54) PROTEIN CONJUGATES AND METHODS FOR THEIR PREPARATION

(75) Inventor: Florencio Zaragoza Dörwald, Smørum (DK)

(73) Assignee: Novo Nordisk Health Care AG, Zurich (CH)

( * ) Notice: Subject to any disclaimer, the term of this patent is extended or adjusted under 35 U.S.C. 154(b) by 1065 days.

(21) Appl. No.: 12/309,142

(22) PCT Filed: Jul. 5, 2007

(86) PCT No.: PCT/EP2007/056819
§ 371 (c)(1),
(2), (4) Date: Mar. 16, 2009

(87) PCT Pub. No.: WO2008/003750
PCT Pub. Date: Jan. 10, 2008

(65) Prior Publication Data
US 2011/0144017 A1    Jun. 16, 2011

Related U.S. Application Data

(60) Provisional application No. 60/819,694, filed on Jul. 10, 2006.

(30) Foreign Application Priority Data

Jul. 7, 2006   (EP) ..................................... 06116776

(51) Int. Cl.
C07K 14/61        (2006.01)
A61K 38/27        (2006.01)
A61K 38/00        (2006.01)
A61K 47/48        (2006.01)
C07K 1/107        (2006.01)

(52) U.S. Cl.
CPC ........... *C07K 14/61* (2013.01); *A61K 47/48215* (2013.01); *C07K 1/1077* (2013.01)

(58) Field of Classification Search
None
See application file for complete search history.

(56) References Cited

U.S. PATENT DOCUMENTS

| | | | | |
|---|---|---|---|---|
| 4,002,531 | A | | 1/1977 | Royer |
| 4,179,337 | A | * | 12/1979 | Davis et al. ................... 435/181 |
| 5,795,560 | A | * | 8/1998 | Reed ............................ 424/1.49 |
| 5,981,718 | A | | 11/1999 | Olsen et al. |
| 6,010,871 | A | | 1/2000 | Takahara et al. |
| 6,077,939 | A | | 6/2000 | Wei et al. |
| 6,566,506 | B2 | * | 5/2003 | Greenwald et al. ........ 530/391.1 |
| 6,673,347 | B1 | | 1/2004 | Offord et al. |
| 7,045,318 | B2 | | 5/2006 | Ballance |
| 7,049,285 | B2 | | 5/2006 | Park |
| 7,056,942 | B2 | | 6/2006 | Hildesheim et al. |
| 7,524,813 | B2 | * | 4/2009 | Zundel et al. ................... 514/1.1 |
| 7,816,320 | B2 | | 10/2010 | Hays et al. |

| | | |
|---|---|---|
| 2003/0190304 A1 | 10/2003 | Thompson et al. |
| 2004/0127417 A1 | 7/2004 | Finn |
| 2005/0170404 A1 | 8/2005 | Cho et al. |
| 2006/0135427 A1 | 6/2006 | Hays et al. |
| 2007/0099917 A1 | 5/2007 | Nice et al. |
| 2007/0105770 A1 | 5/2007 | Johansen et al. |
| 2007/0111926 A1 | 5/2007 | Zundel et al. |
| 2009/0325865 A1 | 12/2009 | Reslow |

FOREIGN PATENT DOCUMENTS

| | | |
|---|---|---|
| CN | 1528787 A | 9/2004 |
| CN | 1528797 | 9/2004 |
| EP | 137234 A2 | 4/1985 |
| EP | 243929 A2 | 11/1987 |
| EP | 605963 A2 | 7/1994 |
| EP | 785276 A1 | 7/1997 |
| EP | 950665 A1 | 10/1999 |
| EP | 1548016 | 6/2005 |
| JP | 2001-519784 | 10/2001 |
| RU | 2385879 | 2/2008 |
| WO | 90/03401 A1 | 4/1990 |
| WO | 9300109 A1 | 1/1993 |
| WO | 93/12812 A1 | 7/1993 |
| WO | 95/32003 A1 | 11/1995 |
| WO | 96/41813 A2 | 12/1996 |
| WO | 97/39768 A1 | 10/1997 |
| WO | 98/05363 | 2/1998 |
| WO | WO 9826747 | 6/1998 |
| WO | 01/58935 A2 | 8/2001 |
| WO | 01/70685 A2 | 9/2001 |
| WO | WO 02055532 | 7/2002 |
| WO | WO 03044056 | 5/2003 |
| WO | 04/000366 A1 | 12/2003 |
| WO | WO 2004007687 | 1/2004 |
| WO | 2004/108667 A2 | 12/2004 |
| WO | 2005/014024 A2 | 2/2005 |
| WO | 2005/034988 A1 | 4/2005 |
| WO | 2005/035565 A1 | 4/2005 |
| WO | WO 2005035553 | 4/2005 |
| WO | 2005/070468 A2 | 8/2005 |
| WO | 2005/074546 A2 | 8/2005 |
| WO | 2005070468 A2 | 8/2005 |
| WO | WO 2005/074650 | 8/2005 |
| WO | 2005123140 A2 | 12/2005 |
| WO | 2006/042848 A2 | 4/2006 |
| WO | 2006042847 A2 | 4/2006 |
| WO | 2006/069220 A2 | 6/2006 |
| WO | 2006/134148 A2 | 12/2006 |
| WO | 2006134148 A2 | 12/2006 |
| WO | 2007/025988 A2 | 3/2007 |

OTHER PUBLICATIONS

Website: http://legal-dictionary.thefreedictionary.com/represents, 1 page, retrieved on Jun. 24, 2014.*

(Continued)

*Primary Examiner* — Satyanarayana R Gudibande
(74) *Attorney, Agent, or Firm* — Jianjie Hu

(57) ABSTRACT

Reductive amination of peptide-derived aldehydes with anilines or heteroarylamines containing a property-modifying group provides new, hydrolytically stable protein conjugates, suitable for therapy.

11 Claims, 1 Drawing Sheet

(1 of 1 Drawing Sheet(s) Filed in Color)

(56) References Cited

OTHER PUBLICATIONS

Zhang and Tam, Analytical Biochemistry, 1996, vol. 223, pp. 87-93.
Zatsepin, et al, Bioconjugate Chemistry, 2002, vol. 13 pp. 822-830.
Tam J., Journal of the American Chemical Society, 1995, vol. 117, pp. 3893-3899.
Gaertner, H.F. et al, Bioconjugate Chemistry, 1996, vol. 7, No. 1, pp. 38-44.
Zalipsky S, Bioconjugate Chemistry, 1995, vol. 6, No. 2, pp. 150-165.
http://www.merriam-webster.com/dictionary/composition Dictionary Definition of Composition Retrived From . . . 3 pages.
Breinbauer, R et al. Chembiochem Azide—Alkyne Coupling: A Powerful Reaction for . . . 2003 4 11 1147-1149.
Baumann G et al. Metabolism: Clinical and Experimental In-Vivo Kinetics of a Covalent Growth Hormone-Binding Protein Complex 1989 38 4 330-333.
Clark et al. Journal of Biological Chemistry Long-Acting Growth Hormone Produced by Conjugation With Polyethylene Glycol 1996 271 36 21969-21977.
Durieux, P et al. Tetrahedron Letters. Synthesis of Biotinylated Glycosulfopeptides by . . . 2001 42 12 2297-2299.
Gorman, J.J et al. The Journal of Biological Chemistry Transglutaminase Amine Substrates for Photochemical Labeling and Cleavable Cross-Linking of Proteins 1980 255 3 1175-1180.
Huntsman—http://huntsman.com/textile_effects/media/cibacron_RAC_brochure.pdf 2008 . . . 4 pages.
Ingallinella, P et al. Bioorganic & Medicinal Chemistry Letters a New Method for Chemoselective Conjugation of . . . 2001 11 10 1343-1346.
King, H.D et al. Bioconjugate Chemistry Monoclonal Antibody Conjugates of . . . 1999 10 2 279-288.
Rose, Keith et al. Bioconjugate Chemistry Natural Peptides as Building Blocks for the Synthesis of Large Protein-Like Molecules With Hydrazone and Oxime Linkages 1996 7-552-556.
Sato, H et al. Bioconjugate Chemistry Transglutaminase-Mediated Dual and Site-Specific Incorporation of Poly . . . 2000 11 4 502-509.
Scott, W.L et al. Bioorganic & Medicinal Chemistry Letters Synthesis of Reagents for the One Step Incorporation of Hydrazide Functionality Onto the Lysine Residues . . . 1996 6 13 1491-1496.
Sato Haruya Advanced Drug Delivery Reviews Enzymatic Procedure for Site-Specific Pegylation of Proteins 2002 54 4 487-504.
Shao et al. Journal of the American Chemical Society Unprotected Peptides as Building Blocks for the Synthesis of Peptide Dendrimers With Oxime, Hydrazone, and Thiazolidine Linkages 1995 117 14 3893-3899.
Stella Journal of Pharmaceutical Sciences Prodrugs: Some Thoughts and Current Issues 2010 99-4755-4765.
Thumshirn, G et al. European Journal of Medicinal Chemistry. Multimeric Cyclic RGD Peptides as Potential Tools for . . . 2003 9 12 2717-2725.
Vippagunta et al. Advanced Drug Delivery Reviews Crystalline Solids 2001 48-3-26.
Wada, E et al. Biotechnology Letters Enzymatic Modification of . . . 2001 23-1367-1372.
Wilkinson, Ian R. et al. Nature Medicine a Ligand-Receptor Fusion of Growth Hormone Forms a Dimer and is a Potent Long-Acting Agonist 2007 13 9 1108-1113.
Yurkovetskiy, A. et al. Biomacromolecules. Fully Degradable Hydrophilic Polyals for Protein Modification 2005 6 5 2648-2658.
Zhang, L et al. Proceedings of the National Academy of Sciences of the USA Preparation of Functionally Active Cell-Permeable Peptides by . . . 1998 95 16 9184-9189.
Reactive Dye Affinity Chromatography Matrices, Sigma Website, 1996, http://sigmaaldrich.com , pp. 1-4.
U.S. Appl. No. 60/957,732, Aug. 24, 2007, Buchardt.
Uniprot database entry P01241 (retreived from http://www.uniprot.org/uniprot/P01241 on Nov. 6, 2013, 18 pages).
Native protein definition (retreived from http://www.biology-online.org/dictionary/Native_protein on Nov. 12, 2013, 2 pages).
National hormone and peptide program (retrieved from http://www.humc.edu/hormones/material.html on Nov. 12, 2013, 3 pages).
Lei Tao et al, Polymer Preprints, "New Pegylation Method for Tyrosine Via a Biomimetic Strategy", 2005, vol. 46, No. 2, pp. 309-310.
Lavey Brian J. et al.,Antibody catalyzed hydrolysis of a phosphotriester,Title :Bioorganic & Medicinal Chemistry Letters, 1996,vol. 6, Issue 13, pp. 1523-1524.
Ito S et al. Synthesis and Antitumor Activity of Cysteinyl-3,4-dihydroxyphenylalaninesa and Related Compounds, "J Med. Chem." Year 1981,vol. 24, pp. 673-677.
Berneis K et al. Metabolic actions of growth hormone direc and indirect, "Clinical Endocrinology and Metabolism" Year 1996, vol. 10, No. 3, pp. 337-352.
Chawla R K et al. Structural Variants of Human Growth Hormone: Biochemical, Genetic, and Clinical Aspects, "Annual Review of Medicine" Year 1983, vol. 34, pp. 519-545.
Edwards C k et al. A Newly Defined Property of Somatotropin: Primiing of Macrophages for Production of Superoxide Anion, "Science" Year1988, vol. 239, pp. 769-751.
Venkatachalam M A et al. Energy Thresholds That Determine Membrane Integrity and Injury in a Renal Epithelial Cell Line (LLC-PK1), "The Journal of Clinical Investigation" Year 1988, vol. 81, pp. 745-758.
Rudman D et al. Effects of Human Growth Hormone in Men Over 60 Years Old "The new England Journal of Medicine", Year 1990, vol. 323, No. 1.
Mateo C et al. Removal of Amphipathic Epitopes from Genetically Engineered Antibodies: Production modified Immunoglobulins withReduced Immunogenicity, "Hybridoma" Year 2000, vol. 19, pp. 463-471.
Sayed S et al.Potent Antithrombin Activity and Delayed Clearance From the Circulation Characterize Recombinant Hirudin Genetically Fused to Albumin, "Blood" Year 1997, vol. 89, pp. 3243-3252.
Theresa M. Allen, Opportunities in Drug Delivery, "Liposomes" Year 1997, vol. 54, Suppl 4, pp. 8-14.
Sada Eizo et al. Resistance to Proteolysis of Antibody Ligands Modified with Polyethylene Glycol, "Journal of Fermentation and Bioengineering" Year 1991, vol. 71, No. 2, pp. 137-139.
Karlsson F A et al. Biosensor Analysis of the Interaction between Immobilized Human Serum Albumin and Drug Compounds for Prediction of Human Serum Albumin Binding Levels, "J. Med. Chem." Year 2000, vol. 43, pp. 1986-1992.
Muller-Newen et al. Soluble Receptors for Cytokines and Growth Factors, "International Archives of Allergy and Immunology" Year 1996, vol. 111, pp. 99-106.
Baumann et al. The Effect of Circulating Growth Hormone-BindingProtein on Metabolic Clearance, Distribution, and Degradation of Human Growth Hormone,"Journal of Clinical Endocrinology and Metabolism" Year 1987, vol. 64, No. 4, pp. 657-660.
Gerhard Baumann Growth Hormone Heterogeneity: Genes, Isohormones, Variants, and Binding Proteins,"Endocrine Reviews" Year 1991, vol. 12, No. 4, pp. 424-449.
Ikura K et al. Incorporation of Amino acids in to Food Proteins by Transglutaminase, "Agric Biol Chem" Year 1981, vol. 45, No. 11, pp. 2587-2592.
Abuchowski A et al. Soluble Polymer-Enzyme Adducts,"Enzyme as drugs" Year 1981, pp. 367-383.
Fontana A et al. Site-specific modification and PEGylation of pharmaceutical proteins mediated by transglutaminase, "Advanced Drug Delivery Reviews" Year 2008, vol. 60, pp. 13-28.
Website: http://legal-dictionary.thefreedictionary.com/represents, 1 page.
Qian Y et al: "Probing the hydrophobic pocket of farnesyltransferase: aromatic substitution of CAAX peptidomimetics leads to highly potent inhibitors",Journal: Bioorganic & Medicinal Chemistry, vol. 7, No. 12,1 Year Dec. 1999, pp. 3011-3024.
Xiaoxia Wen et al: "Improved Radiolabeling of PEGylated Protein: PEGylated Annexin V for Noninvasive Imaging of Tumor Apoptosis",Journal :Cancer Biotherapy & Radiopharmaceuticals, Year 1 Oct. 2003,vol. 18, No. 5, pp. 819-827.

* cited by examiner

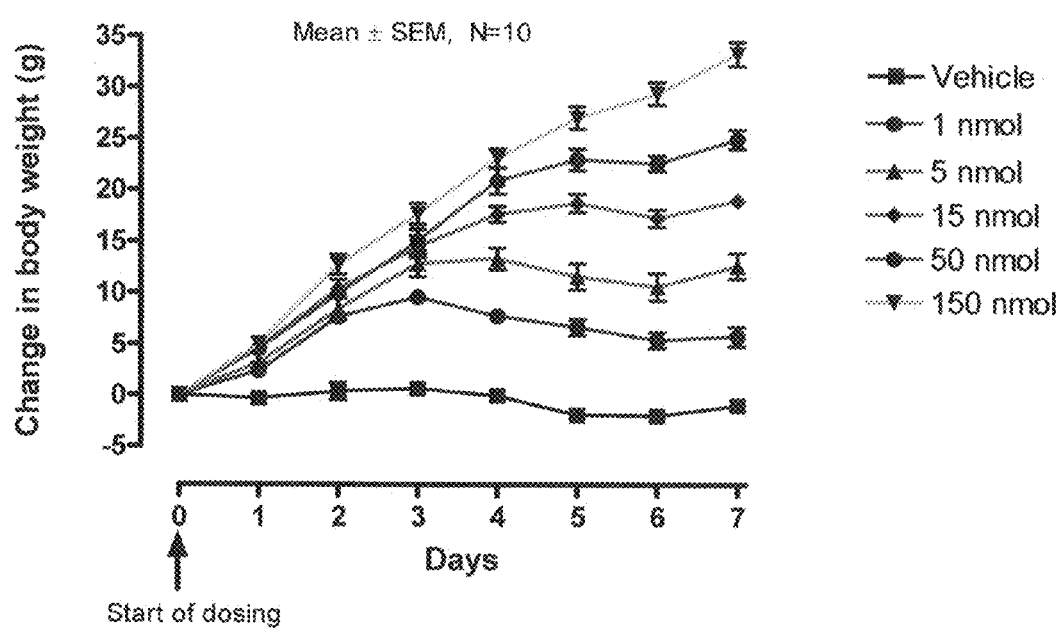

```
                        SEQUENCE LISTING

<160> NUMBER OF SEQ ID NOS: 4

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 2
<211> LENGTH: 261
<212> TYPE: PRT
<213> ORGANISM: Artificial Sequence
<220> FEATURE:
<223> OTHER INFORMATION: Synthetic

<400> SEQUENCE: 2

Met Val Asp Asn Lys Phe Asn Lys Glu Arg Arg Arg Ala Arg Arg Glu
1               5                   10                  15

Ile Arg His Leu Pro Asn Leu Asn Arg Glu Gln Arg Arg Ala Pro Ile
            20                  25                  30

Arg Ser Leu Arg Asp Asp Pro Ser Gln Ser Ala Asn Leu Leu Ala Glu
        35                  40                  45

Ala Lys Lys Leu Asn Arg Ala Gln Ala Pro Lys Tyr Arg Gly Gly Ser
    50                  55                  60

Asp Asp Asp Asp Lys Ser Phe Pro Thr Ile Pro Leu Ser Arg Leu Phe
65                  70                  75                  80

Asp Asn Ala Met Leu Arg Ala His Arg Leu His Gln Leu Ala Phe Asp
                85                  90                  95
```

```
Thr Tyr Gln Glu Phe Glu Glu Ala Tyr Ile Pro Lys Glu Gln Lys Tyr
                100                 105                 110

Ser Phe Leu Gln Asn Pro Gln Thr Ser Leu Cys Phe Ser Glu Ser Ile
            115                 120                 125

Pro Thr Pro Ser Asn Arg Glu Glu Thr Gln Gln Lys Ser Asn Leu Glu
        130                 135                 140

Leu Leu Arg Ile Ser Leu Leu Ile Gln Ser Trp Leu Glu Pro Val
145                 150                 155                 160

Gln Phe Leu Arg Ser Val Phe Ala Asn Ser Leu Val Tyr Gly Ala Ser
                165                 170                 175

Asp Ser Asn Val Tyr Asp Leu Leu Lys Asp Leu Glu Glu Gly Ile Gln
            180                 185                 190

Thr Leu Met Gly Arg Leu Glu Asp Gly Ser Pro Arg Thr Gly Gln Ile
        195                 200                 205

Phe Lys Gln Thr Tyr Ser Lys Phe Asp Thr Asn Ser His Asn Asp Asp
210                 215                 220

Ala Leu Leu Lys Asn Tyr Gly Leu Leu Tyr Cys Phe Arg Lys Asp Met
225                 230                 235                 240

Asp Lys Val Glu Thr Phe Leu Arg Ile Val Gln Cys Arg Ser Val Glu
                245                 250                 255

Gly Ser Cys Gly Phe
            260

<210> SEQ ID NO 3
<211> LENGTH: 45
<212> TYPE: PRT
<213> ORGANISM: Artificial Sequence
<220> FEATURE:
<223> OTHER INFORMATION: Synthetic

<400> SEQUENCE: 3

Gly Gly Ala Thr Cys Ala Gly Cys Gly Ala Cys Gly Ala Cys Gly
1               5                   10                  15

Ala Cys Ala Ala Ala Ala Gly Cys Thr Thr Cys Cys Cys Ala Ala Cys
                20                  25                  30

Cys Ala Thr Thr Cys Cys Cys Thr Thr Ala Thr Cys Cys
            35                  40                  45

<210> SEQ ID NO 4
<211> LENGTH: 45
<212> TYPE: PRT
<213> ORGANISM: Artificial Sequence
<220> FEATURE:
<223> OTHER INFORMATION: Synthetic

<400> SEQUENCE: 4

Gly Gly Ala Thr Ala Ala Gly Gly Ala Ala Thr Gly Gly Thr Thr
1               5                   10                  15

Gly Gly Gly Ala Ala Gly Cys Thr Thr Thr Thr Gly Thr Cys Gly Thr
                20                  25                  30

Cys Gly Thr Cys Gly Thr Cys Thr Gly Ala Thr Cys Cys
            35                  40                  45
```

PROTEIN CONJUGATES AND METHODS FOR THEIR PREPARATION

CROSS-REFERENCE TO RELATED APPLICATIONS

This application is a 35 U.S.C. §371 national stage application of International Patent Application PCT/EP2007/056819 (published as WO 2008/003750 A2), filed Jul. 5, 2007, which claimed priority of European Patent Application 06116776.3, filed Jul. 7, 2006; this application further claims priority under 35 U.S.C. §119 of U.S. Provisional Application 60/819,694, filed Jul. 10, 2006.

FIELD OF THE INVENTION

The present invention relates to new protein conjugates and new conjugates of growth hormones with improved pharmacological properties, to methods for their preparation, and to the use of said conjugates in therapy.

BACKGROUND OF THE INVENTION

It is well known that the properties of proteins may be modified by covalently conjugating groups to said proteins. Such conjugation generally requires some functional group in the protein to react with another functional group in the compound to be conjugated to the protein. Typically, amino groups, such as the N-terminal amino group, the ∈-amino group in lysines or the cysteine thiol group have been used in combination with a suitable acylating or alkylating reagent.

It is often desired to conjugate at specific sites, because the biological activity of a chemically modified protein will depend on the site of modification, and this is referred to as regioselective conjugation. Regioselective acylation of growth hormones, such as for instance human growth hormone (hGH) is, however, difficult because this protein contains nine lysine residues of similar reactivity, and mixtures of products usually result. The single components of these mixtures are difficult to isolate, and will therefore usually be obtained in low yield and purity only.

One strategy to attain regioselective conjugation of a property-modifying group to a protein consists in generating a functional group in the protein, which cannot be found in the natural proteinogenic amino acids. Such a unique functional group may, for instance, be an aldehyde or ketone, an alkyne, or an azide.

In particular protein-derived aldehydes have often been used for the conjugation of property-modifying groups to proteins. This conjugation can be achieved by treating the protein-derived aldehyde with an alkoxyamine (R—O—NH$_2$) to form an oxime, with hydrazine-derivatives to form hydrazones, or with 2-aminoethanethiols to form thiazolidines (see for instance Zhang and Tam, Analytical Biochemistry 233, 87-93 (1996); Zatsepin et al., Bioconjugate Chemistry 13, 822-830 (2002)). All these conjugating functional groups are hydrolytically unstable, and may be hydrolyzed by the treatment with acids or bases (Shao and Tam, J. Am. Chem. Soc. 117, 3893-3899 (1995)) at much higher rates than normal peptide bonds. For this reason, the above mentioned conjugates will slowly decompose in aqueous solution, what limits their utility.

Gaertner et al (Bioconjugate Chem. 7, 38-44 (1996)) disclose a method for conjugating Polyethylene glycol (PEG) to IL-8, G-CFS and IKL-1ra by generating an aldehyde at the N-terminus of these proteins, followed by reaction with an alkoxyamine-functionalized PEG. The aldehyde is generated at the N-terminus either by oxidation with periodate if the N-terminal amino acid residue is serine or threonine, or by metal catalyzed oxidative deamination if the N-terminal amino acid residue is different from serine.

N-terminal serine-extended human growth hormone, Ser-hGH, is disclosed as SEQ ID No. 66 in WO 04/007687. This application relates to multimeric forms of for instance hGH with improved properties.

US 20040127417 describes the reductive alkylation of native growth hormone with a PEG-derived aldehyde. In said procedure the slight difference in basicity between the lysine side-chain amino groups and the N-terminal amino group is exploited: under acidic conditions imine formation with the less extensively protonated N-terminal amino group is faster than imine formation with the lysine side-chains, so that a regioselective PEGylation of the N-terminal amino acid can be achieved.

SUMMARY OF THE INVENTION

The present invention provides conjugated peptides according to formula (I)

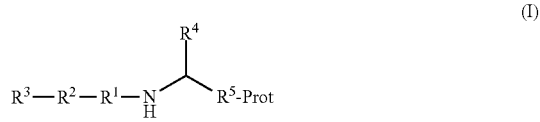

wherein
Prot represents a peptide-derived radical generated by the formal removal of a hydrogen atom from an amino group (—NH$_2$) of said peptide,
R$^1$ represents arylene or a heteroarylene, optionally substituted with a C$_{1-6}$-alkyl, halogen, cyano, nitro, hydroxyl, carboxyl, or aryl group;
R$^2$ represents a bond or a linker, wherein said linker comprises a diradical selected from the group consisting of —C(=O)—NH—, —NH—, —O—, —S—, —O—P(O)(OH)—O—, —O—C(=O)—NH—, —NH—C(=O)—NH—, —(CH$_2$)$_{1-10}$—, —O—(CH$_2$)$_3$—NH—C(=O)—, —C(=O)NH(CH$_2$)$_{2-30}$—, —(CH$_2$)$_{1-30}$C(=O)NH(CH$_2$)$_{2-30}$—, —(CH$_2$)$_{0-30}$C(=O)NH—(CH$_2$CH$_2$O)$_{1-10}$—(CH$_2$)$_{1-5}$—C(=O)—, —C(=O)NH—[(CH$_2$CH$_2$O)$_{1-10}$—(CH$_2$)$_{1-5}$—C(=O)]$_{1-5}$NH(CH$_2$)$_{2-30}$—, —C(=O)—, —(CH$_2$)$_{1-30}$—NHC(=O)—, —(CH$_2$)$_{1-30}$C(=O)—, —NHC(=O)NH(CH$_2$)$_{2-30}$—, —(CH$_2$)$_{1-30}$—NHC(=O)NH(CH$_2$)$_{2-30}$—, —(CH$_2$)$_{0-30}$C(=O)NH(CH$_2$)$_{2-30}$—NHC(=O)—(CH$_2$)$_{0-30}$—, —(CH$_2$)$_{0-30}$C(=O)NH(CH$_2$CH$_2$O)$_{1-30}$—CH$_2$CH$_2$NHC(=O)—(CH$_2$)$_{0-30}$—, or —NH(CH$_2$)$_{2-30}$—,

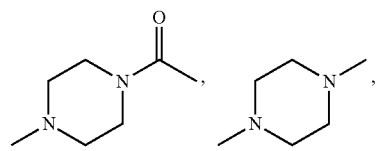

and combinations thereof, and
R$^3$ represents a property-modifying group;
R$^4$ represents hydrogen or C$_{1-6}$-alkyl;
R$^5$ represents —CH$_2$— or —C(=O)—,
or pharmaceutically acceptable salts, prodrugs and solvates thereof.

The present invention provides methods for preparing a peptide compound comprising a property-modifying group, said method comprising the steps of
(a) treatment of an aldehyde or ketone derived from the peptide compound with a property-modifying group-derived aniline or heteroarylamine to yield an imine or a hemiaminal,
(b) treatment of this imine or hemiaminal with a suitable reducing agent, such as NaCNBH$_3$, to yield a secondary amine.

The present invention provides compounds of formula (III)

(III)

wherein $R^1$, $R^2$, and $R^3$ are as defined above.

The present invention provides compounds according to the present invention for use in therapy.

The present invention provides pharmaceutical preparations comprising a compound according to the present invention.

The present invention provides methods of treating diseases benefiting from an increase in the level of circulating growth hormone, the method comprising the administration of a therapeutically effective amount of a compound or a pharmaceutical preparation according to the present invention to a patient in need thereof.

The present invention provides the use of a compound according to the present invention in the manufacture of a medicament for the treatment of a disease benefiting from an increase in the level of circulating growth hormone.

DESCRIPTION OF THE FIGURES

The patent or application file contains at least one drawing executed in color. Copies of this patent or patent application publication with color drawing(s) will be provided by the Office upon request and payment of necessary fee.

FIG. 1. Change in body weight compared to Day 0 of hypophysectomised Sprague Dawley rats after a single subcutaneous dose of the compound of example 2.

DESCRIPTION OF THE INVENTION

The present invention relates to new peptides and new growth hormone (GH) compounds regioselectively conjugated to improve pharmacological properties compared to the parent peptide. This disclosure also provides methods for the preparation of these compounds, and for their use for the treatment of diseases. The conjugates of the present invention are devoid of groups which can be hydrolyzed more readily than peptide bonds, and their stability should therefore be similar as the stability of the unconjugated peptides.

According to the present invention, peptide-derived aldehydes (or "aldehydes derived from the peptide") may be cleanly coupled to PEG-derived anilines or heteroarylamines. Due to the much lower basicity of anilines and heteroarylamines, if compared to aliphatic amines such as lysine side-chain amino groups or the N-terminal amino group of peptides or proteins, and because of the high stability of aniline- or heteroarylamine-derived imines (conjugation of the imine double bond with the aromatic system), a selective imine-formation between the aldehyde-functionality of the peptide and the aniline or heteroarylamine is observed. Reduction of this imine leads to the formation of stable N-alkyl anilines/heteroarylamines.

Accordingly, in one embodiment this invention provides compounds of formula (I)

(I)

wherein
Prot represents a peptide-derived radical generated by the formal removal of a hydrogen atom from an amino group (—NH$_2$) of said peptide,
$R^1$ represents arylene or a heteroarylene, optionally substituted with a $C_{1-6}$-alkyl, halogen, cyano, nitro, hydroxyl, carboxyl, or aryl group;
$R^2$ represents a bond or a linker, wherein said linker comprises a diradical selected from the group consisting of —C(=O)—NH—, —NH—, —O—, —S—, —O—P(O)(OH)—O—, —O—C(=O)—NH—, —NH—C(=O)—NH—, —(CH$_2$)$_{1-10}$—, —O—(CH$_2$)$_3$—NH—C(=O)—, —C(=O)NH(CH$_2$)$_{2-30}$—, —(CH$_2$)$_{1-30}$C(=O)NH(CH$_2$)$_{2-30}$—, —(CH$_2$)$_{0-30}$C(=O)NH—(CH$_2$CH$_2$O)$_{1-10}$—(CH$_2$)$_{1-5}$—C(=O)—, —C(=O)NH—[(CH$_2$CH$_2$O)$_{1-10}$—(CH$_2$)$_{1-5}$—C(=O)]$_{1-5}$NH(CH$_2$)$_{2-30}$—, —C(=O)—, —(CH$_2$)$_{1-30}$—NHC(=O)—, —(CH$_2$)$_{1-30}$C(=O)—, —NHC(=O)NH(CH$_2$)$_{2-30}$—, —(CH$_2$)$_{1-30}$—NHC(=O)NH(CH$_2$)$_{2-30}$—, —(CH$_2$)$_{0-30}$C(=O)NH(CH$_2$)$_{2-30}$—NHC(=O)—(CH$_2$)$_{0-30}$—, —(CH$_2$)$_{0-30}$C(=O)NH(CH$_2$CH$_2$O)$_{1-30}$—CH$_2$CH$_2$NHC(=O)—(CH$_2$)$_{0-30}$—, or —NH(CH$_2$)$_{2-30}$—,

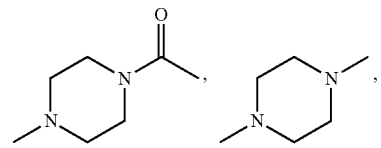

and combinations thereof, and
$R^3$ represents a property-modifying group;
$R^4$ represents hydrogen or $C_{1-6}$-alkyl;
$R^5$ represents —CH$_2$— or —C(=O)—,
or pharmaceutically acceptable salts, prodrugs and solvates thereof.

Unsymmetric biradicals are intended to be connectable to other molecular fragments in both possible directions, i.e. a biradical such as —C(=O)—NH— represents both —C(=O)—NH— and —HN—(C=O)—.

Said compounds have improved pharmacological properties compared to the corresponding unconjugated peptide. Examples of such pharmacological properties include functional in vivo half-life, immunogenicity, renal filtration, protease protection, and albumin binding.

The term "peptide" is intended to indicate a sequence of two or more amino acids joined by peptide bonds, wherein said amino acids may be natural or unnatural. The term encompasses the terms polypeptides and proteins, which may consists of two or more polypeptides held together by covalent interactions, such as for instance cysteine bridges, or non-covalent interactions. It is to be understood that the term is also intended to include peptides, which have been derivatized, for instance by the attachment of lipophilic groups, PEG or prosthetic groups.

The term "peptide-derived aldehyde (or ketone)" or "aldehyde (or ketone) derived from a peptide" is intended to indicate a peptide to which an aldehyde or ketone functional group has been covalently attached, or a peptide on which an aldehyde or ketone functional group has been generated. The preparation of peptide-derived aldehydes is well known to those skilled in the art, and any of these known procedures may be used to prepare the peptide-derived aldehyde required for the realization of the invention disclosed herein.

In the present context, the term "alkyl" is intended to indicate a straight or branched saturated monovalent hydrocarbon radical. The term "alkylene" indicates the corresponding diradical. A "lower alkyl" is an alkyl having from 1 to 6 carbon atoms, also denoted as $C_{1-6}$-alkyl. $C_{1-6}$-alkyl groups include for instance methyl, ethyl, n-propyl, isopropyl, n-butyl, sec-butyl, isobutyl, tert-butyl, n-pentyl, 2-methylbutyl, 3-methylbutyl, 4-methylpentyl, n-hexyl, 1,1-dimethylpropyl, 1,2-dimethylpropyl, 2,2-dimethylpropyl (neopentyl) and 1,2,2-trimethylpropyl.

The term "aryl" as used herein is intended to indicate a mono- or polycyclic carbocyclic aromatic ring radical with for instance 6 to 8 member atoms, or an aromatic ring system radical with for instance from 12 to 18 member atoms. Aryl is also intended to include the partially hydrogenated derivatives of the carbocyclic systems, wherein at least one ring is aromatic. Examples of such partially hydrogenated derivatives include 1,2,3,4-tetrahydronaphthyl, fluorenyl and 1,4-dihydronaphthyl.

The term "heteroaryl" as used herein is intended to indicate a mono- or polycyclic heterocyclic aromatic ring radical with for instance 5 to 7 member atoms, or a heterocyclic aromatic ring system radical with for instance from 7 to 18 member atoms, containing one or more heteroatoms selected from nitrogen, oxygen, and sulfur, wherein N-oxides and sulfur monoxides and sulfur dioxides are permissible heteroaromatic substitutions, such as for instance furyl, thienyl, thiophenyl, pyrrolyl, oxazolyl, thiazolyl, imidazolyl, pyrazolyl isoxazolyl, oxadiazoly, thiadiazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems, provided at least one ring comprising a hetero atom is aromatic. Examples of such partially hydrogenated derivatives include 2,3-dihydrobenzofuranyl, pyrrolinyl, pyrazolinyl, indolinyl, oxazolidinyl, oxazolinyl and oxazepinyl.

Examples of "aryl" and "heteroaryl" includes, but are not limited to phenyl, biphenylyl, indenyl, fluorenyl, phenanthrenyl, azulenyl, naphthyl (1-naphthyl, 2-naphthyl), anthracenyl (1-anthracenyl, 2-anthracenyl, 3-anthracenyl), thienyl (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydrobenzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), and tetrazolyl (5-tetrazolyl, N-tetrazolyl).

The term "arylene" as used herein is intended to indicate a diradical derived from a mono- or polycyclic carbocyclic aromatic ring with for instance 6 to 8 member atoms (for a monocyclic ring), or for instance from 12 to 18 member atoms (for a polycyclic ring). Examples of "arylene" include, but are not limited to, benzene-1,4-diyl, naphthalene-1,8-diyl, 1,2-phenylene, 1,3-phenylene, 1,4-phenylene, 1,2-naphthylene, 1,4-naphthylene, 4,4'-biphenylene, 4,4''-terphenylene and 4,4'''-quaterphenylene and the like and also any corresponding diradial of the radicals mentioned as examples of "aryl".

The term "heteroarylene" as used herein is intended to indicate a diradical derived from a mono- or polycyclic, heterocyclic aromatic ring with for instance 5 to 18 member atoms, containing one or more heteroatoms selected from nitrogen, oxygen, and sulfur, wherein N-oxides and sulfur monoxides and sulfur dioxides are permissible heteroaromatic substitutions. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, 2,5-pyridinediyl, 1,2,4-pyrazol-2,5-diyl, imidazol-1,2-diyl, thiazol-2,4-diyl, (4-phenylimidazole)-4,1'-diyl and (3,5-diphenyl-1,2,4-oxadiazole)-4,4"-diyl and the like and also any corresponding diradical of the radicals mentioned as examples of "heteroaryl".

The term 'linker' is intended to mean an organic diradical with a molecular weight from 14 to 5000.

The term "property-modifying group" is intended to indicate a chemical group, which, when attached to the peptide in question alters one or more of the physicochemical or pharmacological properties of the peptide. Such properties could be solubility, tissue- and organ distribution, lipophilicity, susceptibility to degradation by various proteases, affinity to plasma proteins, such as albumin, functional in vivo half-life, plasma in vivo half-life, mean residence time, clearance, immunogenicity, and renal filtration. It is well-known in the art, that several types of chemical groups may have such property-modifying effects.

The term "functional in vivo half-life" is used in its normal meaning, i.e., the time at which 50% of the biological activity of the peptide, for instance growth hormone, or conjugated peptide, for instance growth hormone, is still present in the body/target organ, or the time at which the activity of the peptide, for instance growth hormone, or peptide, for instance growth hormone, conjugate is 50% of its initial value. As an alternative to determining functional in vivo half-life, "in vivo plasma half-life" may be determined, i.e., the time at which 50% of the peptide, for instance growth hormone, or peptide, for instance growth hormone, conjugate circulate in the plasma or bloodstream prior to being cleared. Determination of plasma half-life is often more simple than determining functional half-life and the magnitude of plasma half-life is usually a good indication of the magnitude of functional in vivo half-life. Alternative terms to plasma half-life include serum half-life, circulating half-life, circulatory half-life, serum clearance, plasma clearance, and clearance half-life.

Measurement of in vivo plasma half-life may be carried out in a number of ways as described in the literature. An increase in in vivo plasma half-life may be quantified as a decrease in clearance (CL) or as an increase in mean residence time (MRT). Conjugated peptide, for instance growth hormone, of the present invention for which the CL is decreased to less than 70%, such as less than 50%, such than less than 20%, such than less than 10% of the CL of the parent peptide as determined in a suitable assay is said to have an increased in vivo plasma half-life. Conjugated peptide, for instance growth hormone, of the present invention for which MRT is increased to more than 130%, such as more than 150%, such as more than 200%, such as more than 500% of the MRT of the parent peptide in a suitable assay is said to have an increased in vivo plasma half-life. Clearance and mean residence time can be assessed in standard pharmacokinetic studies using suitable test animals. It is within the capabilities of a person skilled in the art to choose a suitable test animal for a given peptide. Tests in human, of course, represent the ultimate test. Suitable text animals include normal, Sprague-Dawley male rats, mice and cynomolgus monkeys. Typically the mice and rats are in injected in a single subcutaneous bolus, while monkeys may be injected in a single subcutaneous bolus or in a single iv dose. The amount injected depends on the test animal. Subsequently, blood samples are taken over a period of one to five days as appropriate for the assessment of CL and MRT. The blood samples are conveniently analysed by ELISA techniques.

The term "immunogenicity" of a compound refers to the ability of the compound, when administered to a human, to elicit a deleterious immune response, whether humoral, cellular, or both. In any human sub-population, there may exist individuals who exhibit sensitivity to particular administered peptides. Immunogenicity may be measured by quantifying the presence of antibodies against the peptide and/or peptide responsive T-cells in a sensitive individual, using conventional methods known in the art. In one embodiment the conjugated GH of the present invention exhibit a decrease in immunogenicity in a sensitive individual of at least about 10%, preferably at least about 25%, more preferably at least about 40% and most preferably at least about 50%, relative to the immunogenicity for that individual of the parent GH. In another aspect, immunogenicity may refer to the typical response in a population of similar subjects, such as the typical response in a patient population in a clinical trial.

The term "protease protection" or "protease protected" as used herein is intended to indicate that the conjugated peptide, for instance growth hormone, of the present invention is more resistant to the plasma peptidase or proteases than is the parent peptide. Protease and peptidase enzymes present in plasma are known to be involved in the degradation of circulating proteins and peptides, such as for instance circulating peptide hormones, such as growth hormone. The conjugated peptides of the present invention may also be more resistant to degradation by proteases present in certain tissues and organs, for instance the proteases present in the lung, and the conjugated peptides would thus be better suited for pulmonal or nasal delivery than the corresponding unconjugated peptides.

Resistance of a peptide to degradation by for instance dipeptidyl aminopeptidase IV (DPPIV) is determined by the following degradation assay: Aliquots of the peptide (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 79, 93-102 (1999) and Mentlein et al. Eur. J. Biochem. 214, 829-35 (1993). Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed. The resistance to other plasma proteases or peptidases may be determined in similar ways. In one embodiment the rate of hydrolysis of the peptide, for instance growth hormone, conjugate is less than 70%, such as less than 40%, such as less than 10% of that of the parent peptide.

The most abundant protein component in circulating blood of mammalian species is serum albumin, which is normally present at a concentration of approximately 3 to 4.5 grams per 100 mL of whole blood. Serum albumin is a blood protein of approximately 70,000 daltons which has several important functions in the circulatory system. It functions as a transporter of a variety of organic molecules found in the blood, as the main transporter of various metabolites such as fatty acids and bilirubin through the blood, and, owing to its abundance, as an osmotic regulator of the circulating blood. Serum albumin has a half-life of more than one week, and one approach to increasing the plasma half-life of peptides has been to conjugate to the peptide a group that binds to serum albumin. Albumin binding property may be determined as described in J. Med. Chem., 43, 1986-1992 (2000), which is incorporated herein by reference.

In one embodiment the property modified by the property-modifying group is the functional in vivo half-life of the peptide compound. In a further embodiment the functional in vivo half-life of the peptide compound is increased as compared to the peptide compound without the property-modifying group.

The term "increased" as used in connection with the functional in vivo half-life or plasma half-life is used to indicate that the relevant half-life of the peptide, for instance growth hormone, conjugate is statistically significantly increased relative to that of the parent peptide, as determined under comparable conditions. For instance the relevant half-life may be increased by at least about 25%, such as by at lest about 50%, for instance by at least about 100%, 150%, 200%, 250%, or 500%. In one embodiment the compounds of the present invention exhibit an increase in half-life of at least about 5 h, preferably at least about 24 h, more preferably at least about 72 h, and most preferably at least about 7 days, relative to the half-life of the parent GH.

In one embodiment the property modified by the property-modifying group is the in vivo plasma half-life of the peptide compound. In a further embodiment the in vivo plasma half-life of the peptide is increased as compared to the peptide compound without the property-modifying group. In a further embodiment the in vivo plasma half-life of the peptide is increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

In one embodiment $R^3$ represents a linear or branched polymer or oligomer, optionally substituted with acidic or negatively charged functional groups (such as for instance carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof; or $R^3$ represents a linear or branched $C_{10}$-$C_{90}$ alkyl group, optionally substituted with acidic or negatively charged functional groups (e.g. carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof.

The term "polymer" as used herein is intended to indicate a large molecule consisting of structural units and repeating units connected by covalent chemical bonds. Polymers are distinguished from other molecules in the repetition of many identical, similar, or complementary molecular subunits, also known as monomers in these chains. The monomers are small molecules of low to moderate molecular weight, and are linked to each other by polymerization. Instead of being identical, similar monomers can have varying chemical substituents. The differences between monomers can affect properties such as solubility, flexibility, and strength. Polymers may be organic or inorganic. Examples of polymers for use with the present invention are linear or branched polyethylene glycol (PEG), poloxamer, poly(lactic acid), polylactide-glycolide copolymers, oligosaccharide, peptides, proteins, and linear or branched oligosaccharides selected from such as cellulose, starch, hyaluronic acid, agar, hydroxyethyl cellulose, hydroxyethyl starch or pentosan, or combinations thereof.

The term "oligomer" as used herein is intended to indicate a large molecule consisting of structural units and repeating units connected by covalent chemical bonds and which consists of a relatively small, known number of monomer units, in contrast to a polymer which consists of a large, unknown number of monomers.

In one embodiment $R^3$ represents a linear or branched polyethylene glycol (PEG), poloxamer, poly(lactic acid), poly(lactide)-glycolide copolymer, oligosaccharide, peptides, proteins, or combinations thereof, optionally substituted with acidic or negatively charged functional groups, with basic or cationic functional groups, or with combinations thereof.

The term "polyethylene glycol", "Peg" or "PEG" (poly (ethylene glycol) means a polydisperse or monodisperse diradical of the structure

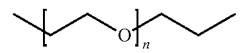

wherein n is an integer larger than 1, and its molecular weight is between approximately 100 and approximately 1,000,000 Da.

The term "mPEG" or "mPeg" means a polydisperse or monodisperse radical of the structure

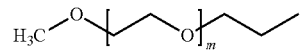

wherein m is an integer larger than 1. Thus, an mPEG wherein m is 90 has a molecular weight of 3991 Da, i.e. approximately 4 kDa. Likewise, an mPEG with an average molecular weight of 20 kDa has an average m of 454. Due to the process for producing mPEG these molecules often have a distribution of molecular weights. This distribution is described by the polydispersity index.

Due to this distribution of m, mPEG with a molecular weight of 20 kDa may also be referred to as MeO—$(CH_2CH_2O)_{400-500}$, mPEG with a molecular weight of 30 kDa may also be referred to as MeO—$(CH_2CH_2O)_{600-700}$, and mPEG with a molecular weight of 40 kDa may also be referred to as MeO—$(CH_2CH_2O)_{850-950}$. The heavier mPEG chains may be difficult to prepare as a single chain molecule, and they are thus made as branched mPEG. Notably, mPEG with a molecular weight of 40 kDa may be achieved with as a branched mPEG comprising to arms of 20 kDa each.

The term "polydispersity index" as used herein means the ratio between the weight average molecular weight and the number average molecular weight, as known in the art of polymer chemistry (see for instance "Polymer Synthesis and Characterization", J. A. Nairn, University of Utah, 2003). The polydispersity index is a number which is greater than or equal to one, and it may be estimated from Gel Permeation Chromatographic data. When the polydispersity index is 1, the product is monodisperse and is thus made up of compounds with a single molecular weight. When the polydispersity index is greater than 1 it is a measure of the polydispersity of that polymer, i.e. how broad the distribution of polymers with different molecular weights is.

The use of for example "mPEG20000" in formulas, compound names or in molecular structures indicates an mPEG residue wherein mPEG is polydisperse and has a molecular weight of approximately 20 kDa.

The polydispersity index typically increases with the molecular weight of the PEG or mPEG. When reference is made to 20 kDa PEG and in particular 20 kDa mPEG it is intended to indicate a compound (or in fact a mixture of compounds) with a polydisperisty index below 1.06, such as below 1.05, such as below 1.04, such as below 1.03, such as between 1.02 and 1.03. When reference is made to 30 kDa PEG and in particular 30 kDa mPEG it is intended to indicate a compound (or in fact a mixture of compounds) with a polydisperisty index below 1.06, such as below 1.05, such as below 1.04, such as below 1.03, such as between 1.02 and 1.03. When reference is made to 40 kDa PEG and in particular 40 kDa mPEG it is intended to indicate a compound (or in fact a mixture of compounds) with a polydisperisty index below 1.06, such as below 1.05, such as below 1.04, such as below 1.03, such as between 1.02 and 1.03

In one embodiment $R^3$ represents a linear or branched $C_{10}$-$C_{90}$ alkyl group, optionally substituted with acidic or negatively charged functional groups (e.g. carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof.

In formula (I), Prot designates a peptide monoradical, that is a peptide having an unpaired electron. The unpaired electron may be present anywhere in the peptide, but will primarily be obtainable by removing a hydrogen atom from an NH group. In one embodiment the Prot radical is formed by the formal removal of a hydrogen atom from the N-terminal amino group. In one embodiment the Prot radical is formed by the formal removal of a hydrogen atom from an amino acid side chain. In one embodiment the Prot radical is formed by the formal removal of a hydrogen atom from the amino group of lysine side chains. In one embodiment the Prot radical is formed by the formal removal of a hydrogen atom from the $NH_2$ group of glutamine side chains. In one embodiment the Prot radical is formed by the formal removal of a hydrogen atom from the NH group of asparagine side chains. This formal removal may be performed by any of several methods known in the art, for instance by use of a method according to the invention.

In one embodiment Prot is obtainable from a peptide-derived aldehyde or ketone of formula

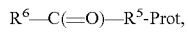

$$R^6-C(=O)-R^5\text{-Prot},$$

wherein
$R^5$ is as described above, and
$R^6$ represents hydrogen or an optionally substituted α-carbon atom.

In one embodiment $R^6$ represents hydrogen, $C_{1-6}$-alkyl or $C_{1-6}$-cycloalkyl.

In the present context, the term "cycloalkyl" is intended to indicate a cyclic saturated monovalent hydrocarbon radical. A "lower cycloalkyl" is an cycloalkyl having from three to six carbon atoms, also denoted as $C_{1-6}$-cycloalkyl. $C_{1-6}$-cycloalkyl groups include for instance cyclopropyl, cyclobutyl, cyclopentyl, 2-methyl-cyclopentyl, and cyclohexyl.

In one embodiment Prot represents a peptide-derived radical generated by the formal removal of a hydrogen atom from an amino group ($-NH_2$) of a peptide or protein, and wherein said amino group is the N-terminal amino group of the peptide, a side-chain amino group of lysine residue in the peptide, or a side-chain amino group of glutamine or asparagine ($CONH_2$) residue in the peptide.

In one embodiment Prot represents a growth hormone-derived radical.

The term "growth hormone" or "GH" is intended to indicate a protein, which exhibits growth hormone activity as determined in assay I herein, or, when used in connection with structural formulas, a radical derived from such protein. hGH indicates the human growth hormone. A peptide which exhibits an activity above 20%, such as above 40%, such as above 60%, such as above 80% of that of hGH in assay (I) is defined as a growth hormone compound.

In one embodiment Prot represents a human growth hormone-derived radical. In one embodiment Prot is a radical of human growth hormone (hGH) having an amino acid sequence as set forth in SEQ ID No. 1. In one embodiment Prot is formed by removal of a hydrogen atom from the N-terminal amino acid. In one embodiment the Prot radical is formed by the formal removal of a hydrogen atom from the side-chain aminocarbonyl group ($H_2N-CO-$) of the glutamine at the position corresponding to position 40 in SEQ ID No. 1. In one embodiment, the Prot radical is formed by the formal removal of a hydrogen atom from the side-chain aminocarbonyl group ($H_2N-CO-$) of the glutamine at the position corresponding to position 141 in SEQ ID No. 1.

In one embodiment the growth hormone part of the growth hormone-derived radical is a variant of hGH, wherein a variant is understood to be the compound obtained by substituting one or more amino acid residues in the hGH sequence with another natural or unnatural amino acid; and/or by adding one or more natural or unnatural amino acids to the hGH sequence; and/or by deleting one or more amino acid residue from the hGH sequence, wherein any of these steps may optionally be followed by further derivatization of one or more amino acid residues, for instance by pegylation resulting in a di- or multi-pegylated growth hormone variant. In particular, such substitutions are conservative in the sense that one amino acid residue is substituted by another amino acid residue from the same group, i.e. by another amino acid residue with similar properties. Amino acids may conveniently be divided in the following groups based on their properties: Basic amino acids (such as arginine, histidine and lysine), acidic amino acids (such as glutamic acid and aspartic acid), polar amino acids (such as glutamine, histidine, cysteine and asparagine), hydrophobic amino acids (such as leucine, isoleucine, proline, methionine and valine), aromatic amino acids (such as phenylalanine, tryptophan, tyrosine) and small amino acids (such as glycine, alanine, serine and threonine).

In one embodiment the peptide may be extended with up to about 100 amino acid residues at the N-terminal as compared to the parent peptide. Such an N-terminally extended peptide may be described by the formula Z-XX-Prot, wherein Z represent serine or threonine, XX represents any sequence of 1-50 amino acids, and Prot represents the parent peptide. In one embodiment Z represents serine. In one embodiment XX represents a sequence with up to 40, such as up to 20, such as up to 10, such as up to 5, such as 1, 2, 3, 4 or 5 amino acid residues. In one embodiment the peptide is hGH extended with up to 100 amino acid residues at the N-terminal as compared to SEQ ID No. 1. In particular, said extension is up to 50, such as up to 40, such as up to 20, such as up to 10, such as up to 5, such as 1, 2 or 3 amino acid residues.

In one embodiment the peptide has at least 80%, such as at least 85%, such as at least 90%, such as at least 95% identity with the amino acid sequence in SEQ ID No. 1. In one embodiment said identity is coupled to at least 20%, such as at least 40%, such as at least 60%, such as at least 80% of the growth hormone activity of hGH as determined in assay I herein.

The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two peptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci. USA 89, 10915-10919 (1992) for the BLOSUM 62 comparison matrix) is also used by the algorithm.

Preferred parameters for a peptide sequence comparison include the following:

Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

In one embodiment Prot represents an antibody-derived radical. In one embodiment Prot represents a radical derived from a fragment of an antibody.

The term "antibody" is intended to indicate an immunoglobulin molecule or a derivative of either thereof, which has the ability to specifically bind to an antigen under typical physiological conditions for significant periods of time such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen). The term antibody also includes diabodies and single chain antibodies.

Furthermore, although the two domains of the Fv fragment, $V_L$ and $V_H$, are coded for by separate genes, they may be joined, using recombinant methods, by a synthetic linker that enables them to be made as a single peptide chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Other forms of single chain antibodies, such as diabodies are included within the term antibody.

It also should be understood that the term antibody also generally includes polyclonal antibodies, monoclonal antibodies (mAbs), antibody-like polypeptides, such as chimeric antibodies and humanized antibodies, and anti-idiotypic (anti-Id) antibodies to antibodies. An antibody as generated can possess any isotype.

The term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)).

The term "fragment of an antibody" or "antibody-fragment" is intended to indicate a fragment of an antibody which fragment retains the ability to specifically bind to an antigen. Examples of binding fragments encompassed within the term "antibody" include (i) a Fab fragment, a monovalent fragment consisting of the $V_L$, $V_H$, $C_L$ and $C_H1$ domains; (ii) $F(ab)_2$ and $F(ab')_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain; and (vi) an isolated complementarity determining region (CDR). The antibody fragments may be provided by any known technique, such as enzymatic cleavage, peptide synthesis, and recombinant techniques.

Examples of structural formulas for compounds of formula I comprise:

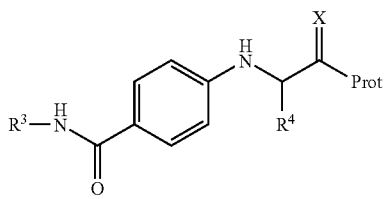

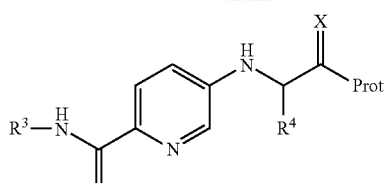

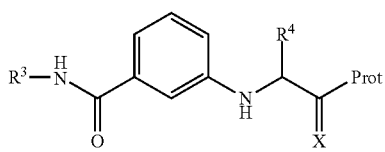

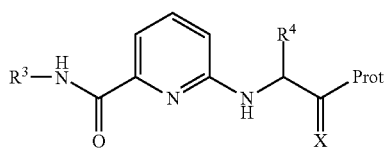

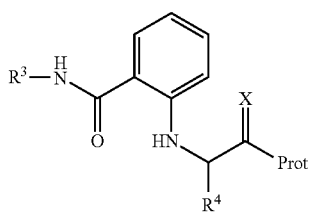

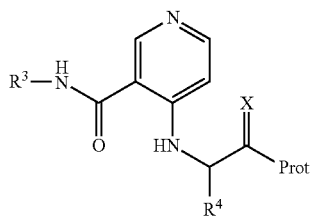

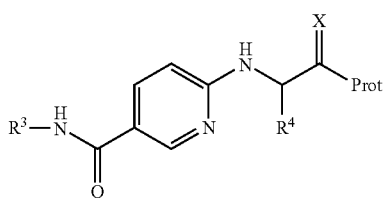

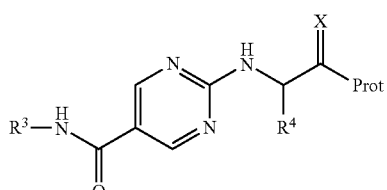

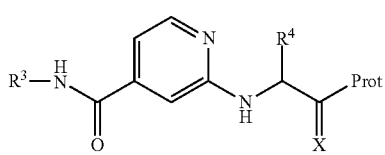

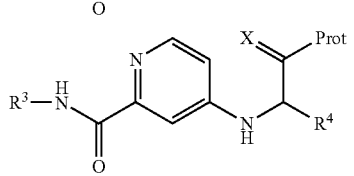

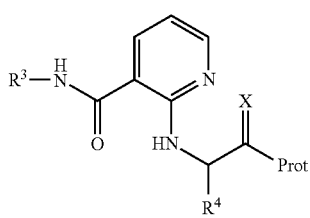

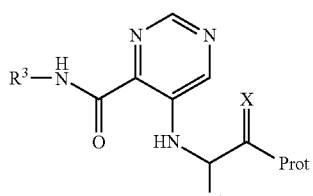

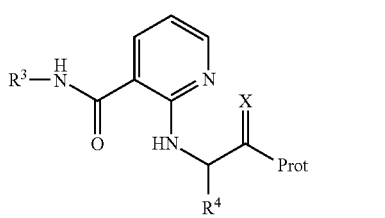

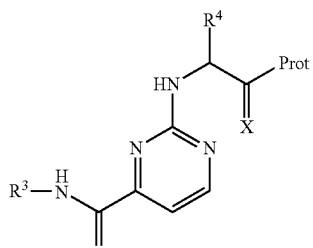

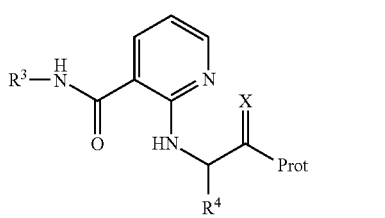

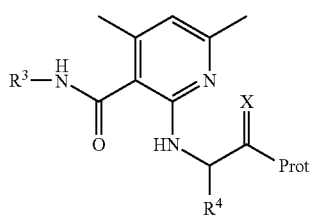

17
-continued
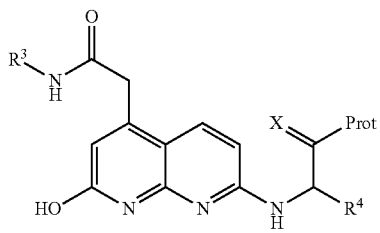
18
-continued
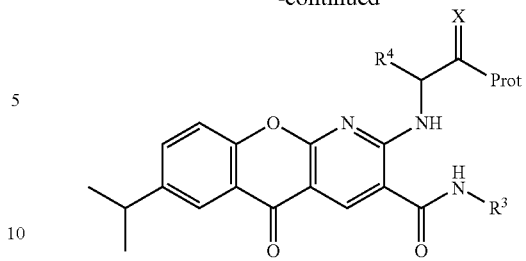
Non-limiting examples of compounds of formula (I) comprise:
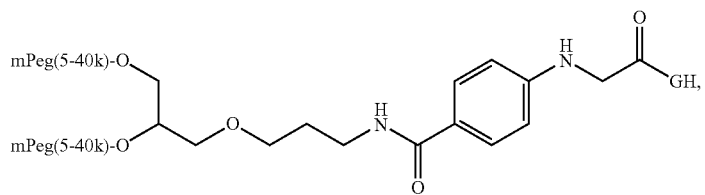
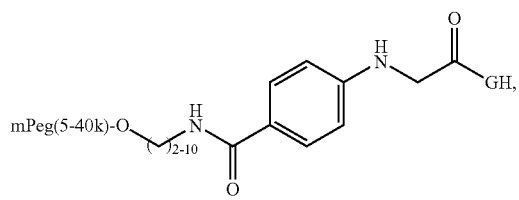
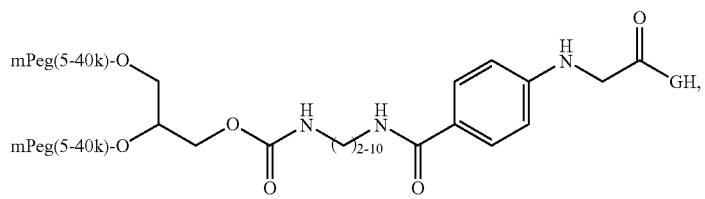
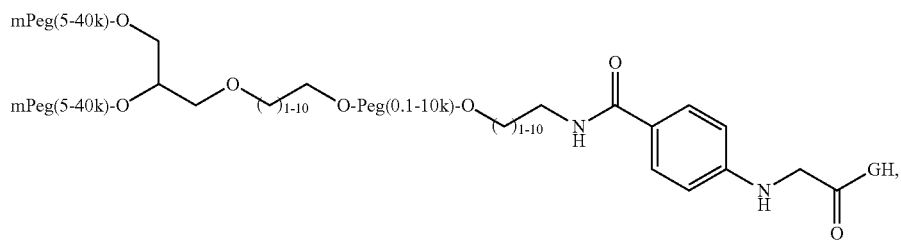
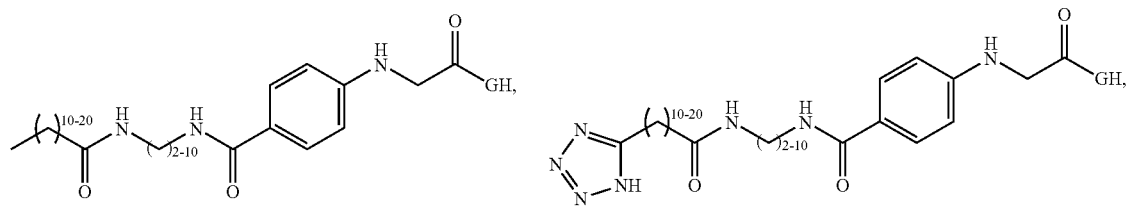
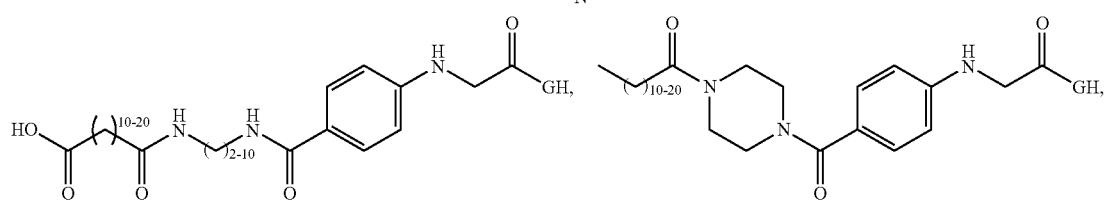

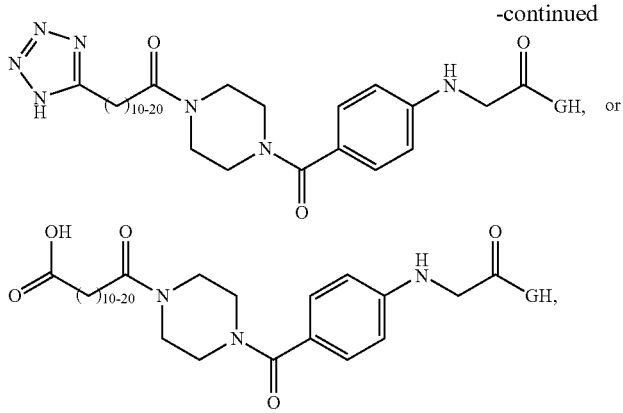

and pharmaceutically acceptable salts, prodrugs and solvates thereof, wherein GH represents a radical formed from a growth hormone, for instance human growth hormone, wherein the GH radical is formed by removal of one hydrogen atom from the N-terminal amino group. These compounds can be prepared by periodate-mediated oxidation of Ser-GH (growth hormone extended at the N-terminus with one serine), followed by condensation of the resulting aldehyde with a 4-aminobenzamide and reduction of the resulting imine with $NaCNBH_3$ or another suitable reducing agent.

Non-limiting examples of compounds of formula (I) comprise:

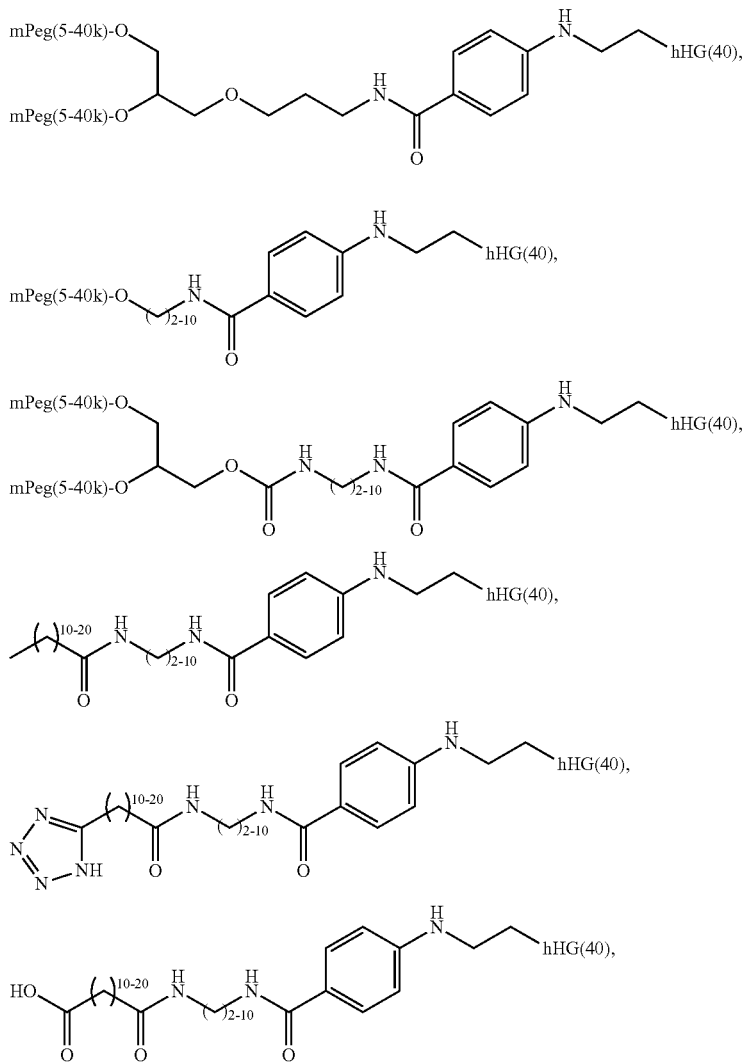

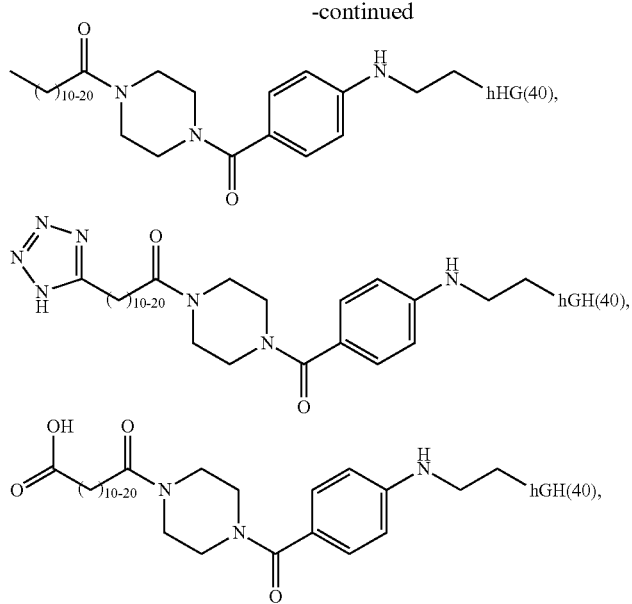

and pharmaceutically acceptable salts, prodrugs and solvates thereof, wherein hGH(40) represents a radical formed by the formal removal of one hydrogen atom from the side-chain aminocarbonyl group ($H_2N-CO-$) of glutamine at position 40 in human growth hormone (hGH). These compounds can be prepared by transglutaminase-mediated transamination of hGH with 1,3-diamino-2-propanol, followed by periodate-mediated oxidation to an aldehyde of the formula $H-CO-CH_2$-hGH(40), followed by imine-formation with a 4-aminobenzamide and reduction of the resulting imine with $NaCNBH_3$ or another suitable reducing agent.

Non-limiting examples of compounds of formula (I) comprise:

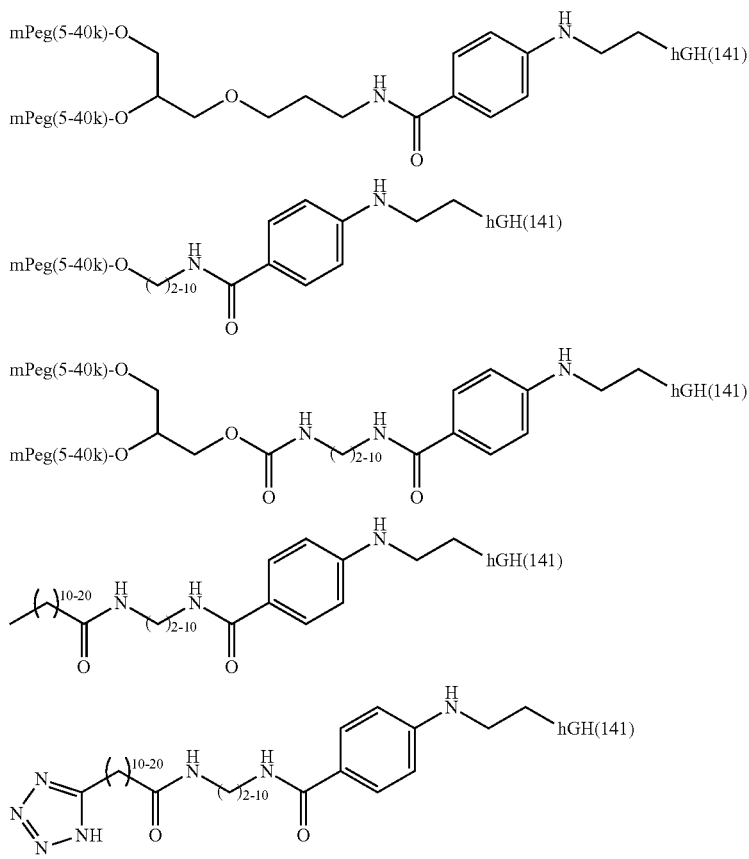

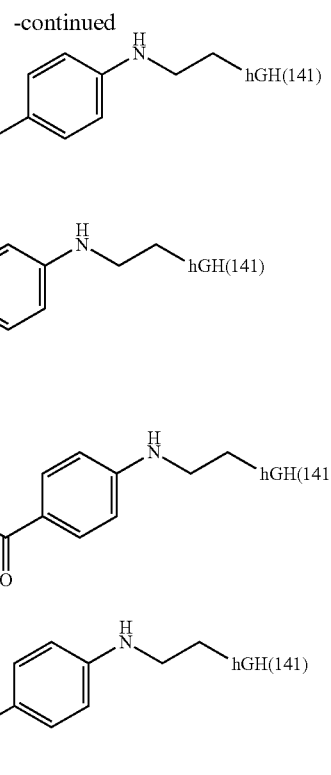

and pharmaceutically acceptable salts, prodrugs and solvates thereof, wherein hGH(141) represents a radical formed by removal of one hydrogen atom from the side-chain aminocarbonyl group ($H_2N$—CO—) of glutamine at position 141 in human growth hormone (hGH). These compounds can be prepared by transglutaminase-mediated transamination of hGH with 1,3-diamino-2-propanol, followed by periodate-mediated oxidation to an aldehyde of the formula H—CO—$CH_2$-hGH(141), followed by imine-formation with a 4-aminobenzamide and reduction of the resulting imine with $NaCNBH_3$ or another suitable reducing agent.

$NaCNBH_3$ is mentioned herein as an example of a suitable reducing agent. However, a number of other reagents may be considered as alternatives to $NaCNBH_3$ as reducing agent for the conversion of imines into secondary amines. Thus, imines derived from oxidized carbohydrates and proteins have been reduced in aqueous solution with the commercially available adduct of borane ($BH_3$) and pyridine (Hashimoto et al., J. Biochem. 123, 468-478 (1998); Yoshida and Lee, Carbohydr. Res 251, 175-186 (1994)). Related reagents are adducts of borane and dimethylsulfide, phosphines, phosphites, substituted pyridines, pyrimidines, imidazoles, pyrazoles, thiazoles, sulfides, ethers, and the like. Further alternatives to $NaCNBH_3$ are catalytic hydrogenation (heterogeneous or homogeneous), $NaBH_4$, (Ehrenfreund-Kleinmann et al., Biomaterials 23, 1327-1335 (2002); Zito and Martinez-Carrion, J. Biol. Chem. 255, 8645-8649 (1980)), $NaHB(OAc)_3$ (Drummond et al., Proteomics 1, 304-310 (2001)), NADPH (the reduced form of NADP, nicotineamide adenine dinucleotide phosphate) or related dihydropyridines (Itoh et al., Tetrahedron Lett. 43, 3105-3108 (2002)), or mixtures of $NaBH_4$ and AcOH. NADPH may also be used in combination with a suitable enzyme, such as glutamate dehydrogenase (Fisher et al., J. Biol. Chem. 257, 13208-13210 (1982)). Each of these reagents may require adjustment of the pH of the solution, in order to provide for a high rate of imine-reduction if compared to the rate of hydrogen-formation (hydronium ion reduction). Thus, some reagents may reduce the imine under neutral or basic reaction conditions, whereas other reagents may require more acidic reaction conditions. Furthermore, some of these reagents may require the use of cosolvents, such as formamide, NMP, acetonitrile, ethylene glycol, isopropanol, and the like, in order to improve the solubility of all reactants or in order to reduce the concentration of water, and thus the rate of hydronium ion reduction.

As used herein, the term "prodrug" includes biohydrolyzable amides and biohydrolyzable esters, acetals, aminals, thioaminals, thioacetals, and hydrazones, and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

As used herein, the term "biohydrolyzable ester" is an ester of a drug substance (in casu, a compound according to the invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable ester is absorbed from the gut and is transformed to a compound according to the present invention in plasma. Many examples of such are known in the art and include by way of example lower alkyl esters (for instance $C_1$-$C_4$-alkyl), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in casu, a compound according to the present invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable amide is absorbed from the gut and is transformed to a compound according to the present invention in plasma. Many examples of such are known in the art and include by way of example lower alkyl amides, α-amino acid amides, alkoxyacyl amides, and alkylaminoalkylcarbonyl amides.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 66, 2 (1977), which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

As used herein, the term "solvate" is a complex of defined stoichiometry formed by a solute and a solvent. Solvents may be, by way of example, water, ethanol, or acetic acid.

In one embodiment the invention relates to methods of improving the pharmacological properties of a peptide, such as growth hormone, the method comprising preparing a conjugated peptide as described below. In particular, improving the pharmacological properties is intended to indicate an increase in the functional in vivo half-life, the plasma in vivo half-life, the mean residence time, or an decrease in the clearance as also described elsewhere herein.

In one embodiment the invention relates to a method of preparing a compound of formula (I), said method comprising the steps of
(a) treatment of an aldehyde or ketone derived from the peptide compound with a property-modifying group-derived aniline or heteroarylamine to yield an imine or a hemiaminal,
(b) treatment of this imine or hemiaminal with a suitable reducing agent to yield a secondary amine.

In one embodiment the property modified by the property-modifying group is the functional in vivo half-life of the peptide compound with the property-modifying group, as compared to the peptide compound without said property-modifying group. In one embodiment the functional in vivo half-life of the peptide compound is increased as compared to the peptide compound without the property-modifying group. in a further embodiment, the approximate functional in vivo half-life of the peptide is increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Peptide-derived aldehydes or ketones may be prepared by several routes.

In one embodiment the peptide-derived aldehyde or ketone is prepared by periodate-mediated oxidation of a peptide containing serine or threonine as the N-terminal amino acid. Such peptide may either be a natural peptide, or may be prepared by standard genetic modification of E. coli or other suitable cells to produce the desired, recombinant variant of the peptide of interest. Alternatively, one or more amino acids comprising an N-terminal serine or threonine may be attached to the N-terminal position of a peptide, such as for instance hGH, by means of an enzyme, for instance an aminopeptidase, in the presence of a large excess of said amino acid(s). The serine or threonine added to the peptide need not be attached directly to the N-terminal amino acid residue. One or more amino acid residues may be inserted between the serine or threonine and the original N-terminus. In this embodiment, the resulting serine- or threonine-comprising peptide may be described by the formula Z-XX-Prot, such as Z-XX-hGH, wherein Z represent serine or threonine, XX represents any sequence of 1-50 amino acids, and Prot represents the peptide, for instance growth hormone. In one embodiment Z represents serine. In one embodiment XX represents a sequence with up to 40, such as up to 20, such as up to 10, such as up to 5, such as 1, 2, 3, 4 or 5 amino acid residues.

In one embodiment the peptide-derived aldehyde or ketone, is prepared by periodate-mediated oxidation of a derivative of the peptide, in which one or several of the available side-chains of asparagine or glutamine have been used to acylate an amine of the general formula $H_2N-CH_2-CH(R^7)-CH_2-NH_2$, wherein $R^7$ represents OH, SH, or $NH_2$. Such an acylation may be accomplished selectively by treating a peptide, such as for instance hGH, with an excess of said amine and a suitable enzyme, such as a glutamyl or aspartyl transpeptidase.

In one embodiment the peptide-derived aldehyde or ketone is prepared by periodate-mediated oxidation of a peptide compound containing a 2-aminoethanol substructure.

In one embodiment a peptide-derived aldehyde is prepared by periodate-mediated oxidation of a peptide transaminated enzymatically with 1,3-diamino-2-propanol.

In one embodiment a peptide-derived aldehyde or ketone is prepared by coupling a thiol of the general formula $HS-R^8-C(=O)-R^9$, wherein $R^8$ represents an organic diradical, and $R^9$ represents hydrogen or an organic radical, to one of the available tyrosine residues by means of a tyrosinase, for instance a mushroom tyrosinase, as described in the literature (S. Ito et al., J. Med. Chem. 24, 673-677 (1981)).

In one embodiment a peptide-derived aldehyde is prepared by coupling a thiol of the general formula $HS-R^{10}-CH(R^{11})-CH_2-R^{12}$, wherein $R^{10}$ represents an organic diradical, and $R^{11}$ and $R^{12}$ independently of each other represents OH or $NH_2$, by means of a tyrosinase, for instance a mushroom tyrosinase, as described in the literature (S. Ito et al., J. Med. Chem. 24, 673-677 (1981))., followed by periodate-mediated oxidation of the resulting product.

In one embodiment a peptide-derived aldehyde or ketone is prepared by amide formation of the carboxy-terminal amino acid of the peptide with an unnatural α-amino acid amide, which contains a ketone or an aldehyde as side-chain functional group. Such an unnatural α-amino acid amide may be coupled with the peptide with the aid of an enzyme, such as a carboxypeptidase.

In one embodiment a peptide-derived aldehyde or ketone is obtained by regioselective alkylation of the N-terminal amino group with a compound comprising a moiety which subsequently can be transformed into an aldehyde or a ketone, by exploiting the lower basicity of the N-terminal amino group if compared to the lysine side-chain amino groups (see US 20040127417).

In one embodiment a peptide-derived aldehyde or ketone is prepared by hydrolysis of an acetal or a hemiacetal.

In one embodiment a peptide-derived aldehyde or ketone is prepared by feeding a genetically modified or unmodified organism producing said peptide with an unnatural amino acid containing an aldehyde or ketone functionality, wherein said amino acid will be incorporated into the peptide, followed by isolation and purification of the peptide into which the unnatural amino acid has been incorporated. This can be, for instance, also achieved by means of a mutated tRNA synthetase, as described in the literature (Tsao et al., J. Am. Chem. Soc. 128, 4572-4573 (2006), and articles cited therein). Use of this method may provide control over the position at which the property-modifying group is inserted as the unnatural amino acid will be incorporated at a certain codon, the position of which can be chosen as desired. In one embodiment said unnatural amino acid is (acetylphenyl)alanine or (formylphenyl)alanine. In one embodiment the mRNA encoding the peptide comprises at least one codon encoding phenylalanine.

The peptide part of the peptide-derived aldehyde or ketone may be any peptide, for which the conjugation to a property-modifying group is desirable. The peptide may thus be a therapeutically effective peptide. There are myriads of therapeutically effective and interesting peptides in the scientific literature and the patent literature, and it is well-known that property-modification of such peptides may provide therapeutical benefits or other benefits. For instance will an increase in functional in vivo half-life be interesting for a number of these peptides, but there is also other examples of interesting properties to be modified as described elsewhere herein. The person skilled in the art is quite capable of determining which peptides would benefit from a derivatization according to the present invention. The methods and compounds of the invention are thus not limited by the nature of the peptide chosen.

In one embodiment the peptide is a growth hormone. In one embodiment the peptide is human growth hormone. In one embodiment the peptide is human growth hormone (hGH) which comprises the amino acid sequence as set forth in SEQ ID No. 1. In one embodiment the growth hormone part of the growth hormone-derived radical is a variant of hGH as described elsewhere herein. In one embodiment the peptide is growth hormone, such as human growth hormone, extended with up to about 100 amino acid residues at the N-terminal as compared to the parent peptide as described elsewhere herein. In one embodiment the peptide is a growth hormone, for instance human growth hormone, such as a human growth hormone having the amino acid sequence of SEQ ID No. 1, which growth hormone has been N-terminally extended with one residue, wherein this residue is serine or threonine. In one embodiment the peptide is has at least 80%, such as at least 85%, such as at least 90%, such as at least 95% identity with the amino acid sequence in SEQ ID No. 1. In one embodiment said identity is coupled to at least 20%, such as at least 40%, such as at least 60%, such as at least 80% of the growth hormone activity of hGH as determined in assay I herein.

In one embodiment the growth hormone peptide is derivatized with the aldehyde or ketone functionality in the position corresponding to position 40 in SEQ ID No. 1 and in another embodiment, the growth hormone peptide is derivatized with the aldehyde or ketone functionality in the position corresponding to position 141 in SEQ ID No. 1. This regioselective derivatization may be obtained by use of a suitable method as described above, for instance by transglutaminase-mediated coupling of hGH with 1,3-diamino-2-propanol, followed by periodate-mediated oxidation of the transaminated hGH to the corresponding aldehyde. In one embodiment GH is converted into an aldehyde by periodate-mediated oxidation of Ser-GH.

In one embodiment Prot represents an antibody-derived radical. In one embodiment Prot represents a radical derived from a fragment of an antibody.

The peptide part of the peptide-derived aldehyde or ketone may be prepared in a number of different ways depending on the nature of the peptide, such as for instance synthesis using standard protein synthesis techniques. In one embodiment however, the peptide is expressed in a suitable host after incorporation of a suitable nucleic acid construct into said host.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial nucleotide sequence encoding a peptide of interest. The construct may optionally contain other nucleic acid segments.

The nucleic acid construct of the invention encoding the peptide of interest may suitably be of genomic or cDNA origin, for instance obtained by preparing a genomic or cDNA library and screening for DNA sequences coding for all or part of the peptide by hybridization using synthetic oligonucleotide probes in accordance with standard techniques (cf. J. Sambrook, E. F. Fritsch, and T. Maniatus, 1989, Molecular Cloning, A Laboratory Manual, 2d edition, Cold Spring Harbor, N.Y.). In one embodiment the DNA sequence encoding the peptide, such as a growth hormone, is of human origin, i.e. derived from a human genomic DNA or cDNA library. In particular, the DNA sequence may be of human origin, for instance cDNA from a particular human organ or cell type or a gene derived from human genomic DNA.

The nucleic acid construct encoding the peptide may also be prepared synthetically by established standard methods, for instance the phosphoamidite method described by Beaucage and Caruthers, Tetrahedron Letters 22, 1859-1869 (1981), or the method described by Matthes et al., EMBO Journal 3, 801-805 (1984). According to the phosphoamidite method, oligonucleotides are synthesized, for instance in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., Science 239, 487-491 (1988).

In one embodiment the nucleic acid construct is a DNA construct which term will be used as an example of a nucleic acid construct in the following.

The DNA construct encoding the peptide of interest may be inserted into a recombinant vector. The recombinant vector into which the DNA construct is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, for instance a plasmid. Alternatively, the vector may be one which, when introduced into a host cell, is integrated into the host cell genome and replicated together with the chromosome(s) into which it has been integrated.

The vector may be an expression vector in which the DNA sequence encoding the peptide of interest is operably linked to additional segments required for transcription of the DNA. In general, the expression vector is derived from plasmid or viral DNA, or may contain elements of both. The term "operably linked" indicates that the segments are arranged so that they function in concert for their intended purposes, for instance transcription initiates in a promoter and proceeds through the DNA sequence coding for the peptide.

The promoter may be any DNA sequence which shows transcriptional activity in the host cell of choice and may be derived from genes encoding proteins either homologous or heterologous to the host cell.

Examples of suitable promoters for directing the transcription of the DNA encoding a peptide, such as growth hormone, in mammalian cells are the SV40 promoter (Subramani et al., Mol. Cell. Biol. 1, 854-864 (1981)), the MT-1 (metallothionein gene) promoter (Palmiter et al., Science 222, 809-814 (1983)) or the adenovirus 2 major late promoter.

An example of a suitable promoter for use in insect cells is the polyhedrin promoter (U.S. Pat. No. 4,745,051; Vasuvedan et al., FEBS Lett. 311, 7-11 (1992)), the P10 promoter (J. M. Vlak et al., J. Gen. Virology 69, 765-776 (1988), the *Autographa californica* polyhedrosis virus basic protein promoter (EP 397 485), the baculovirus immediate early gene 1 promoter (U.S. Pat. Nos. 5,155,037; 5,162,222), or the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., J. Biol. Chem. 255, 12073-12080 (1980); Alber and Kawasaki, J. Mol. Appl. Gen. 1, 419-434 (1982)) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4-c (Russell et al., Nature 304, 652-654 (1983)) promoters.

Examples of suitable promoters for use in filamentous fungus host cells are, for instance, the ADH3 promoter (McKnight et al., The EMBO J. 4, 2093-2099 (1985)) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or by the phage Lambda $P_R$ or $P_L$ promoters or the *E. coli* lac, trp or tac promoters.

The DNA sequence encoding the peptide, such as a growth hormone, may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (for instance from SV40 or the adenovirus 5 Elb region), transcriptional enhancer sequences (for instance the SV40 enhancer) and translational enhancer sequences (for instance the ones encoding adenovirus VA RNAs).

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2μ replication genes REP 1-3 and origin of replication.

When the host cell is a bacterial cell, sequences enabling the vector to replicate are DNA polymerase III complex encoding genes and origin of replication.

The vector may also comprise a selectable marker, for instance a gene the product of which complements a defect in the host cell, such as the gene coding for dihydrofolate reductase (DHFR) or the *Schizosaccharomyces pombe* TPI gene (described by P. R. Russell, Gene 40, 125-130 (1985), or one which confers resistance to a drug, for instance ampicillin, kanamycin, tetracyclin, chloramphenicol, neomycin, hygromycin or methotrexate. For filamentous fungi, selectable markers include amdS, pyrG, argB, niaD and sC.

To direct the peptide into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that which is normally associated with the peptide or may be from a gene encoding another secreted peptide.

For secretion from yeast cells, the secretory signal sequence may encode any signal peptide which ensures efficient direction of the expressed peptide into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., Nature 289, 643-646 (1981)), a modified carboxypeptidase signal peptide (cf. L. A. Valls et al., Cell 48, 887-897 (1987)), the yeast BAR1 signal peptide (cf. WO 87/02670), or the yeast aspartic protease 3 (YAP3) signal peptide (cf. M. Egel-Mitani et al., Yeast 6, 127-137 (1990)).

For efficient secretion in yeast, a sequence encoding a leader peptide may also be inserted downstream of the signal sequence and upstream of the DNA sequence encoding the peptide. The function of the leader peptide is to allow the expressed peptide to be directed from the endoplasmic reticulum to the Golgi apparatus and further to a secretory vesicle for secretion into the culture medium (i.e. exportation of the peptide across the cell wall or at least through the cellular membrane into the periplasmic space of the yeast cell). The leader peptide may be the yeast α-factor leader (the use of which is described in for instance U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the peptide of interest, the promoter and optionally the terminator and/or secretory signal sequence, respectively, and to insert them into suitable vectors containing the information necessary for replication, are well known to persons skilled in the art (cf., for instance, Sambrook et al., op.cit.).

The host cell into which the DNA construct or the recombinant vector is introduced may be any cell which is capable of producing the encoded peptide and includes bacteria, yeast, fungi and higher eukaryotic cells.

Examples of bacterial host cells which, on cultivation, are capable of producing GH are grampositive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinus*, or gramnegative bacteria such as *Echerichia coli*. The transformation of the bacteria may be effected by protoplast transformation or by using competent cells in a manner known per se (cf. Sambrook et al., supra).

When expressing a peptide in bacteria such as *E. coli*, the peptide may be retained in the cytoplasm, typically as insoluble granules (known as inclusion bodies), or may be directed to the periplasmic space by a bacterial secretion sequence. In the former case, the cells are lysed and the granules are recovered and denatured after which the peptide is refolded by diluting the denaturing agent. In the latter case, the peptide may be recovered from the periplasmic space by disrupting the cells, for instance by sonication or osmotic shock, to release the contents of the periplasmic space and recovering the peptide.

Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in for instance Kaufman and Sharp, J. Mol. Biol. 159, 601-621 (1982); Southern and Berg, J. Mol. Appl. Genet. 1, 327-341 (1982); Loyter et al., PNAS USA 79, 422-426 (1982); Wigler et al., Cell 14, 725 (1978); Corsaro and Pearson, Somatic Cell Genetics 7, 603 (1981), Graham and van der Eb, Virology 52, 456 (1973); and Neumann et al., EMBO J. 1, 841-845 (1982).

Examples of suitable yeast cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous peptides therefrom are described, for instance in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, for instance leucine. A suitable vector for use in yeast is the POT1 vector disclosed in U.S. Pat. No. 4,931,373. The DNA sequence encoding a peptide of the invention may be preceded by a signal sequence and optionally a leader sequence, for instance as described above. Further examples of suitable yeast cells are strains of *Kluyveromyces*, such as *K. lactis, Hansenula*, for instance *H. polymorpha*, or *Pichia*, for instance *P. pastoris* (cf. Gleeson et al., J. Gen. Microbiol. 132, 3459-3465 (1986); U.S. Pat. No. 4,882,279).

Examples of other fungal cells are cells of filamentous fungi, for instance *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of peptides is described in, for instance, EP 272 277 and EP 230 023. The transformation of *F. oxysporum* may, for instance, be carried out as described by Malardier et al., Gene 78, 147-156 (1989).

When a filamentous fungus is used as the host cell, it may be transformed with the DNA construct, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, for instance by homologous or heterologous recombination.

Transformation of insect cells and production of heterologous peptides therein may be performed as described in U.S. Pat. Nos. 4,745,051; 4,879,236; 5,155,037; 5,162,222; EP 397,485) all of which are incorporated herein by reference. The insect cell line used as the host may suitably be a *Lepidoptera* cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting the expression of the peptide of interest, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (for instance in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, for instance ammonium sulphate, purification by a variety of chromatographic procedures, for instance ion exchange chromatography, gelfiltration chromatography, affinity chromatography, or the like, dependent on the specific peptide in question.

The conjugated peptides, such as growth hormones obtainable by use of a method according to the invention used may also be derivatized by other means, if so desired. Such additional derivatization may be performed before, during or after use of the steps of the method of the invention. It is within the skill of a person skilled in the art to determine the timing of such additional derivatisation. The peptide used may also already be conjugated to a property-modifying group at one or more further positions in addition to the site or sites to be conjugated according to the present invention.

In one embodiment the property-modifying group-derived aniline or heteroarylamine is of the formula

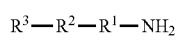

(III)

wherein $R^1$, $R^2$, and $R^3$ are as defined above.

In one embodiment $R^2$ represents a bond, —C(=O)—, —C(=O)—NH—, or

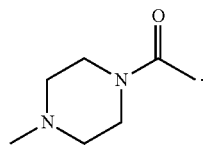

In one embodiment the property modified by the property-modifying group is the functional in vivo half-life of the peptide compound. In a further embodiment the functional in vivo half-life of the peptide compound is increased as compared to the peptide compound without the property-modifying group.

In one embodiment the approximate functional in vivo half-life of the peptide is increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

In one embodiment the property modified by the property-modifying group is the in vivo plasma half-life of the peptide compound. In a further embodiment the in vivo plasma half-life of the peptide is increased as compared to the peptide compound without the property-modifying group. In a further embodiment the in vivo plasma half-life of the peptide is increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

In one embodiment $R^3$ represents a linear or branched polymer or oligomer, optionally substituted with acidic or negatively charged functional groups (such as for instance carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof; or $R^3$ represents a linear or branched $C_{10}$-$C_{90}$ alkyl group, optionally substituted with acidic or negatively charged functional groups (e.g. carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof.

In one embodiment $R^3$ represents a linear or branched $C_{10}$-$C_{90}$ alkyl group, optionally substituted with acidic or negatively charged functional groups (e.g. carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof.

In one embodiment the peptide-derived aldehyde or ketone is of the formula

wherein
Prot is as described above
$R^5$ is —CH$_2$— or —C(=O)—, and
$R^6$ represents hydrogen or an optionally substituted α-carbon atom.

In one embodiment $R^5$ represents —CH$_2$—. In one embodiment $R^5$ represents —C(=O)—. In one embodiment $R^6$ represents hydrogen, $C_{1-6}$-alkyl or $C_{1-6}$-cycloalkyl. In one embodiment $R^6$ represents hydrogen, methyl, ethyl, propyl, cyclopropyl, cyclobutyl, cyclopentyl, or cyclohexyl. In one embodiment $R^6$ represents hydrogen or methyl.

The present invention provides compounds of formula (III)

(III)

wherein $R^1$, $R^2$, and $R^3$ are as defined above.

In one embodiment the property modified by the property-modifying group is the functional in vivo half-life of the peptide compound. In a further embodiment the functional in vivo half-life of the peptide compound is increased as compared to the peptide compound without the property-modifying group.

In one embodiment the property modified by the property-modifying group is the in vivo plasma half-life of the peptide compound. In a further embodiment the in vivo plasma half-life of the peptide is increased as compared to the peptide compound without the property-modifying group. In a further embodiment the in vivo plasma half-life of the peptide is increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

In one embodiment $R^3$ represents a linear or branched polymer or oligomer, optionally substituted with acidic or negatively charged functional groups (such as for instance carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof; or $R^3$ represents a linear or branched $C_{10}$-$C_{90}$ alkyl group, optionally substituted with acidic or negatively charged functional groups (e.g. carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof.

In one embodiment $R^3$ represents a linear or branched $C_{10}$-$C_{90}$ alkyl group, optionally substituted with acidic or negatively charged functional groups (e.g. carboxyl groups, tetrazolyl groups, acylsulfonyl groups, phosphonyl groups, boronic acid groups, phosphates, sulfates, etc), with basic or cationic functional groups (e.g. amino groups, ammonium groups, phosphonium groups), or with combinations thereof.

In one embodiment the invention provides the use of a compound according to formula (III) for the preparation of conjugated peptide with improved pharmacological properties compared to the unconjugated peptide. In a further embodiment the conjugation is performed by use of a method of the present invention.

In one embodiment said growth hormone is a human growth hormone.

In one embodiment said growth hormone comprises the amino acid sequence of SEQ ID No. 1.

In one embodiment the peptide has at least 80%, such as at least 85%, such as at least 90%, such as at least 95% identity with the amino acid sequence in SEQ ID No. 1. In one embodiment said identity is coupled to at least 20%, such as at least 40%, such as at least 60%, such as at least 80% of the growth hormone activity of hGH as determined in assay I herein.

In one embodiment said improved pharmacological property is increased functional in vivo half-life of the peptide.

Compounds of formula (I) wherein Prot represents growth hormone and which exert growth hormone activity may as such be used in the treatment of diseases or states which will benefit from an increase in the amount of circulating growth hormone.

The present invention consequently provides a pharmaceutical composition comprising a conjugated growth hormone of the present invention. In one embodiment the conjugated growth hormone is present in a concentration corresponding to from $10^{-15}$ mg growth hormone pr ml to 200 mg growth hormone pr. ml, such as for instance corresponding to $10^{-10}$ mg growth hormone pr ml to 5 mg growth hormone pr ml. In one embodiment a pharmaceutical composition of the present invention has a pH from 2.0 to 10.0. The composition may further comprise a buffer system, preservative(s), tonicity agent(s), chelating agent(s), stabilizers and surfactants. In one embodiment of the invention the pharmaceutical composition is an aqueous composition, i.e. composition comprising water. Such composition is typically a solution or a suspension. In a further embodiment the pharmaceutical composition is an aqueous solution. The term "aqueous composition" is intended to indicate a composition comprising at least 50% w/w water. Likewise, the term "aqueous solution" is intended to indicate a solution comprising at least 50% w/w water, and the term "aqueous suspension" intended to indicate a suspension comprising at least 50% w/w water.

In one embodiment the pharmaceutical composition is a freeze-dried composition, whereto the physician or the patient adds solvents and/or diluents prior to use.

In one embodiment the pharmaceutical composition is a dried composition (for instance freeze-dried or spray-dried) ready for use without any prior dissolution.

In one embodiment the pharmaceutical composition comprising an aqueous solution of a growth hormone conjugate of the invention, and a buffer, wherein said growth hormone conjugate is present in a concentration corresponding to from 0.1-100 mg growth hormone pr ml or above, and wherein said composition has a pH from 2.0 to 10.0.

In one embodiment the pH of the pharmaceutical composition is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In one embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)aminomethan, bicine, tricine, malic acid, succinate, maleic acid, fumaric acid, tartaric acid, aspartic acid or mixtures thereof. Each one of these specific buffers constitutes an alternative embodiment of the invention.

In one embodiment the composition further comprises a pharmaceutically acceptable preservative. In a further embodiment the preservative is selected from the group consisting of phenol, o-cresol, m-cresol, p-cresol, methyl p-hydroxybenzoate, propyl p-hydroxy-benzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In one embodiment the preservative is present in a concentration of from 0.1 mg/ml to 20 mg/ml. In one embodiment the preservative is present in a concentration of from 0.1 mg/ml to 5 mg/ml. In one embodiment the preservative is present in a concentration of from 5 mg/ml to 10 mg/ml. In one embodiment the preservative is present in a concentration of from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 20$^{th}$ edition, 2000.

In one embodiment the pharmaceutical composition further comprises an isotonic agent. In a further embodiment of the invention the isotonic agent is selected from the group consisting of a salt (for instance sodium chloride), a sugar or sugar alcohol, an amino acid (for instance L-glycine, L-histidine, arginine, lysine, isoleucine, aspartic acid, tryptophan, threonine), an alditol (for instance glycerol (glycerine), 1,2-propanediol (propyleneglycol), 1,3-propanediol, 1,3-butanediol) polyethyleneglycol (for instance PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a $C_{4-8}$-hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects obtained using the methods of the invention. In one embodiment the sugar or sugar alcohol concentration is between 1 mg/ml and 150 mg/ml. In one embodiment the isotonic agent is present in a concentration from 1 mg/ml to 50 mg/ml. In one embodiment the isotonic agent is present in a concentration from 1 mg/ml to 7 mg/ml. In one embodiment the isotonic agent is present in a concentration from 8 mg/ml to 24 mg/ml. In one embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 20th edition, 2000.

In one embodiment the pharmaceutical composition further comprises a chelating agent. In a further embodiment of the invention the chelating agent is selected from salts of ethylenediaminetetraacetic acid (EDTA), citric acid, and aspartic acid, and mixtures thereof. In one embodiment the chelating agent is present in a concentration of from 0.1 mg/ml to 5 mg/ml. In one embodiment the chelating agent is present in a concentration of from 0.1 mg/ml to 2 mg/ml. In one embodiment the chelating agent is present in a concentration of from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 20$^{th}$ edition, 2000.

In one embodiment the pharmaceutical composition further comprises a stabilizer. The use of a stabilizer in pharmaceutical compositions is well-known to the skilled person. For convenience reference is made to Remington: The Science and Practice of Pharmacy, 20$^{th}$ edition, 2000.

A pharmaceutical composition of the invention may further comprise an amount of a agent sufficient to decrease aggregate formation by the peptide during storage of the composition. The term "aggregate formation" is intended to indicate a physical interaction between the peptide molecules that results in formation of oligomers, which may remain soluble, or large visible aggregates that precipitate from the solution. The term "during storage" is intended to indicate a liquid pharmaceutical composition or composition once prepared, is not immediately administered to a subject. Rather, following preparation, it is packaged for storage, either in a liquid form, in a frozen state, or in a dried form for later reconstitution into a liquid form or other form suitable for administration to a subject. The term "dried form" is intended to indicate the liquid pharmaceutical composition or composition is dried either by freeze drying (i.e., lyophilization; see, for example, Williams and Polli J. Parenteral Sci. Technol. 38, 48-59 (1984)), spray drying (see Masters (1991) in Spray-Drying Handbook (5th ed; Longman Scientific and Technical, Essez, U.K.), pp. 491-676; Broadhead et al. Drug Devel. Ind. Pharm. 18, 1169-1206 (1992); and Mumenthaler et al. Pharm. Res. 11, 12-20 (1994)), or air drying (Carpenter and Crowe Cryobiology 25, 459-470 (1988); and Roser Biopharm. 4, 47-53 (1991)). In one embodiment, said agent is an amino acid base. The term "amino acid base" is intended to indicate an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment amino acids to use in preparing the compositions of the invention are those carrying a charged side chain, such as arginine, lysine, aspartic acid, and glutamic acid. Any stereoisomer (i.e., L or D isomer, or mixtures thereof) of a particular amino acid (methionine, histidine, arginine, lysine, isoleucine, aspartic acid, tryptophan, threonine and mixtures thereof) or combinations of these stereoisomers or glycine or an organic base such as but not limited to imidazole, may be present in the pharmaceutical compositions of the invention so long as the particular amino acid or organic base is present either in its free base form or its salt form. In one embodiment the L-stereoisomer of an amino acid is used. In one embodiment the L-stereoisomer is used. Compositions of the invention may also be formulated with analogues of these amino acids. The term "amino acid analogue" is intended to indicate a derivative of the naturally occurring amino acid that brings about the desired effect of decreasing aggregate formation by the peptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In one embodiment of the invention the amino acids or amino acid analogues are used in a concentration, which is sufficient to prevent or delay aggregation of the peptide.

In one embodiment the pharmaceutical composition further comprises methionine (or other sulphuric amino acids or amino acid analogous) to inhibit oxidation of methionine residues to methionine sulfoxide when the peptide acting as the therapeutic agent is a peptide comprising at least one methionine residue susceptible to such oxidation. The term "inhibit" is intended to indicate minimal accumulation of methionine oxidized species over time. Inhibiting methionine oxidation results in greater retention of the peptide in its proper molecular form. Any stereoisomer of methionine (L or D isomer) or any combinations thereof may be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be obtained by adding methionine such that the ratio of methionine added to methionine residues ranges from about 1:1 to about 1000:1, such as 10:1 to about 100:1.

In one embodiment the pharmaceutical composition further comprises a stabilizer selected from the group of high molecular weight polymers or low molecular compounds. In one embodiment the stabilizer is selected from polyethylene glycol (for instance PEG 3350), polyvinyl alcohol (PVA), polyvinylpyrrolidone, carboxy-/hydroxycellulose or derivates thereof (for instance HPC, HPC-SL, HPC-L and HPMC), cyclodextrins, sulphur-containing substances as monothioglycerol, thioglycolic acid and 2-methylthioethanol, and different salts (for instance. sodium chloride). Each one of these specific stabilizers constitutes an alternative embodiment of the invention.

A pharmaceutical composition of the invention may also comprise additional stabilizing agents, which further enhance stability of a therapeutically active peptide therein. Stabilizing agents include, but are not limited to, methionine and EDTA, which protect the peptide against methionine oxidation, and a nonionic surfactant, which protects the peptide against aggregation associated with freeze-thawing or mechanical shearing.

In one embodiment the pharmaceutical composition further comprises a surfactant. In one embodiment the surfactant is selected from a detergent, ethoxylated castor oil, polyglycolyzed glycerides, acetylated monoglycerides, sorbitan fatty acid esters, polyoxypropylene-polyoxyethylene block polymers (for instance poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, for instance Tween-20, Tween-40, Tween-80 and Brij-35), monoglycerides or ethoxylated derivatives thereof, diglycerides or polyoxyethylene derivatives thereof, alcohols, glycerol, lectins and phospholipids (for instance phosphatidyl serine, phosphatidyl choline, phosphatidyl ethanolamine, phosphatidyl inositol, diphosphatidyl glycerol and sphingomyelin), derivates of phospholipids (for instance dipalmitoyl phosphatidic acid) and lysophospholipids (for instance palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, for instance lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (for instance cephalins), glyceroglycolipids (for instance galactopyransoide), sphingoglycolipids (for instance ceramides, gangliosides), dodecylphosphocholine, hen egg lysolecithin, fusidic acid derivatives—(for instance sodium tauro-dihydrofusidate etc.), long-chain fatty acids and salts thereof (for instance oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (for instance N-alkyl-N, N-dimethylammonio-1-propanesulfonates, 3-cholamido-1-propyldimethylammonio-1-propanesulfonate, cationic surfactants (quaternary ammonium bases) (for instancecetyltrimethylammonium bromide, cetylpyridinium chloride), non-ionic surfactants (for instance Dodecyl β-D-glucopyranoside), poloxamines (for instance Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: The Science and Practice of Pharmacy, 20$^{th}$ edition, 2000.

It is possible that other ingredients may be present in a pharmaceutical composition of the present invention. Such additional ingredients may include wetting agents, emulsifiers, antioxidants, bulking agents, tonicity modifiers, chelating agents, metal ions, oleaginous vehicles, proteins (for instance human serum albumin, gelatine or other proteins) and a zwitterion (for instance an amino acid such as betaine, taurine, arginine, glycine, lysine and histidine). Such additional ingredients, of course, should not adversely affect the overall stability of the pharmaceutical composition of the present invention.

Pharmaceutical compositions containing a growth hormone conjugate according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Pharmaceutical compositions of the invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Pharmaceutical compositions of the invention may further be compounded in, or attached to, for example through covalent, hydrophobic and electrostatic interactions, a drug carrier, drug delivery system and advanced drug delivery system in order to further enhance stability of the GH conjugate, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Pharmaceutical compositions of the invention are useful in the composition of solids, semisolids, powder and solutions for pulmonary administration of GH conjugate, using, for example a metered dose inhaler, dry powder inhaler and a nebulizer, all being devices well known to those skilled in the art.

Pharmaceutical compositions of the invention are specifically useful in the composition of controlled, sustained, protracting, retarded, and slow release drug delivery systems. More specifically, but not limited to, compositions are useful in composition of parenteral controlled release and sustained release systems (both systems leading to a many-fold reduction in number of administrations), well known to those skilled in the art. Even more preferably, are controlled release and sustained release systems administered subcutaneous.

Without limiting the scope of the invention, examples of useful controlled release system and compositions are hydrogels, oleaginous gels, liquid crystals, polymeric micelles, microspheres, nanoparticles, Methods to produce controlled release systems useful for compositions of the invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration may be performed by means of an infusion pump. A further option is a composition which may be a solution or suspension for the administration of the GH conjugate in the form of a nasal or pulmonal spray. As a still further option, the pharmaceutical compositions containing the GH conjugate of the invention can also be adapted to transdermal administration, for instance by needle-free injection or from a patch, optionally an iontophoretic patch, or transmucosal, for instance buccal, administration.

The term "stabilized composition" refers to a composition with increased physical stability, increased chemical stability or increased physical and chemical stability.

The term "physical stability" of a peptide composition as used herein refers to the tendency of the peptide to form biologically inactive and/or insoluble aggregates of the peptide as a result of exposure of the peptide to thermo-mechanical stresses and/or interaction with interfaces and surfaces that are destabilizing, such as hydrophobic surfaces and interfaces. Physical stability of the aqueous peptide compositions is evaluated by means of visual inspection and/or turbidity measurements after exposing the composition filled in suitable containers (for instance cartridges or vials) to mechanical/physical stress (for instance agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition is classified physical unstable with respect to peptide aggregation, when it shows visual turbidity in daylight. Alternatively, the turbidity of the composition can be evaluated by simple turbidity measurements well-known to the skilled person. Physical stability of the aqueous peptide compositions can also be evaluated by using a spectroscopic agent or probe of the conformational status of the peptide. The probe is preferably a small molecule that preferentially binds to a non-native conformer of the peptide. One example of a small molecular spectroscopic probe of peptide structure is Thioflavin T. Thioflavin T is a fluorescent dye that has been widely used for the detection of amyloid fibrils. In the presence of fibrils, and perhaps other peptide configurations as well, Thioflavin T gives rise to a new excitation maximum at about 450 nm and enhanced emission at about 482 nm when bound to a fibril peptide form. Unbound Thioflavin T is essentially non-fluorescent at the wavelengths.

Other small molecules may be used as probes of the changes in peptide structure from native to non-native states. For instance the "hydrophobic patch" probes that bind preferentially to exposed hydrophobic patches of a peptide. The hydrophobic patches are generally buried within the tertiary structure of a peptide in its native state, but become exposed as a peptide begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the peptide compositions as used herein refers to the ability of said peptide to withstand chemical reactions involving the breaking of covalent bonds or the formation of new covalent bonds in the peptide structure leading to formation of chemical degradation products with potential less biological potency and/or potential increased immunogenic properties compared to the native peptide structure. Various chemical degradation products can be formed depending on the type and nature of the native peptide and the environment to which the peptide is exposed. When conjugated to a suitable group, the peptides of the present invention may be significantly more chemically stable than the corresponding unconjugated peptides.

Most peptides are prone to deamidation, a process in which the side chain amide group in glutaminyl or asparaginyl residues is hydrolysed to form a free carboxylic acid. Other degradation pathways involves formation of high molecular weight transformation products where two or more peptide molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. The chemical stability of the peptide composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (for instance SEC-HPLC and/or RP-HPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

In one embodiment the pharmaceutical composition comprising the growth hormone conjugate is stable for more than 6 weeks of usage and for more than 3 years of storage.

In one embodiment than 4 weeks of usage and for more than 3 years of storage.

In one embodiment the pharmaceutical composition comprising the growth hormone conjugate is stable for more than 4 weeks of usage and for more than two years of storage.

In one embodiment the pharmaceutical composition comprising the growth hormone conjugate is stable for more than 2 weeks of usage and for more than two years of storage.

As stated, compounds of formula (I) wherein Prot represents growth hormone and which exert growth hormone activity (or pharmaceutical compositions comprising such compounds) may as such be used in the treatment of diseases or states which will benefit from an increase in the amount of circulating growth hormone.

Consequently, the present invention provides a compound of the present invention for use in therapy.

The present invention also provides a method of treating a disease, condition or disorder benefiting from an increase in the level of circulating growth hormone, the method comprising the administration of a therapeutically effective amount of a compound of the invention to a patient in need thereof.

The present invention also provides a method for the treatment of growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in for instance hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteotomia, for instance from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; traumatic spinal cord injury; subarachnoid haemorrhage; very low birth weight; metabolic syndrome; glucocorticoid myopathy; or short stature due to glucucorticoid treatment in children, the method comprising administering to a patient in need thereof a therapeutically effective amount of a compound according to formula (I).

The term "treatment" and "treating" is intended to indicate the management and care of a patient for the purpose of combating a condition, a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs. The term "therapeutically effective amount" of a compound is intended to indicate an amount sufficient to cure, alleviate or partially arrest the clinical manifestations of a given disease and its complications. An amount adequate to accomplish this is defined as "therapeutically effective amount". Effective amounts for each purpose will depend on for instance the severity of the disease or injury as well as the weight, sex, age and general state of the subject. It will be understood that determining an appropriate dosage may be achieved using routine experimentation, by constructing a matrix of values and testing different points in the matrix, which is all within the ordinary skills of a trained physician or veterinary.

In one embodiment, the compound of the invention is administered by parental administration. A typical parenteral dose is in the range of $10^{-9}$ mg/kg to about 100 mg/kg body weight per administration. Typical administration doses are from about 0.0000001 to about 10 mg/kg body weight per administration. The exact dose will depend on for instance indication, medicament, frequency and mode of administration, the sex, age and general condition of the subject to be treated, the nature and the severity of the disease or condition to be treated, the desired effect of the treatment and other factors evident to the person skilled in the art.

Typical dosing frequencies are twice daily, once daily, bi-daily, twice weekly, once weekly or with even longer dosing intervals. Due to the prolonged halflives of the conjugated peptides of the present invention, a dosing regime with long dosing intervals, such as twice weekly, once weekly or with even longer dosing intervals is a particular embodiment of the invention.

In one embodiment said administration is performed every second day or with longer intervals.

In one embodiment said administration is performed once a week or with longer intervals.

In one embodiment said administration is performed once a month or with longer intervals.

In one embodiment said condition, disease or disorder is selected from wasting in AIDS patients, GH-deficiency due to a pituitary tumor, and poor growth in children due to GH-deficiency, renal failure, Turner syndrome, and Prader-Willi syndrome.

In one embodiment the invention provides a method for the acceleration of the healing of muscle tissue, nervous tissue or wounds; the acceleration or improvement of blood flow to damaged tissue; or the decrease of infection rate in damaged tissue, the method comprising administration to a patient in need thereof an effective amount of a therapeutically effective amount of a compound of formula (I).

The present invention also provides the use of a compound of the invention in the manufacture of a medicament for the treatment of a condition, disease or disorder benefiting from an increase in the level of circulating growth hormone.

In one embodiment, said condition, disease or disorder is selected from growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in for instance hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, for instance from tibia or 1$^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; traumatic spinal cord injury; subarachnoid haemorrhage; very low birth weight; metabolic syndrome; glucocorticoid myopathy; and short stature due to glucucorticoid treatment in children.

In one embodiment said disease is selected from wasting in AIDS patients, GH-deficiency due to a pituitary tumor, and poor growth in children due to GH-deficiency, renal failure, Turner syndrome, or Prader-Willi syndrome.

Many diseases are treated using more than one medicament in the treatment, either simultaneously administered or sequentially administered. It is therefore within the scope of the present invention to use compounds of formula (I) in therapeutic methods for the treatment of one of the above mentioned diseases in combination with one or more other therapeutically active compound normally used in the treatment said diseases. By analogy, it is also within the scope of the present invention to use compounds of formula (I) in combination with other therapeutically active compounds normally used in the treatment of one of the above mentioned diseases in the manufacture of a medicament for said disease.

The following is a list of embodiments of the present invention:

Embodiment 1: A Conjugated Peptide According to Formula (I)

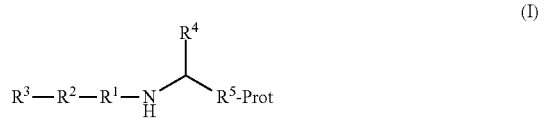

wherein
Prot represents a peptide-derived radical generated by the formal removal of a hydrogen atom from an amino group (—NH$_2$) of said peptide,
R$^1$ represents arylene or a heteroarylene, optionally substituted with a C$_{1-6}$-alkyl, halogen, cyano, nitro, hydroxyl, carboxyl, or aryl group;
R$^2$ represents a bond or a linker, wherein said linker comprises a diradical selected from the group consisting of —C(=O)—NH—, —NH—, —O—, —S—, —O—P(O)(OH)—O—, —O—C(=O)—NH—, —NH—C(=O)—NH—, —(CH$_2$)$_{1-10}$—, —O—(CH$_2$)$_3$—NH—C(=O)—, —C(=O)NH(CH$_2$)$_{2-30}$—, —(CH$_2$)$_{1-30}$C(=O)NH(CH$_2$)$_{2-30}$—, —(CH$_2$)$_{0-30}$C(=O)NH—(CH$_2$CH$_2$O)$_{1-10}$—(CH$_2$)$_{1-5}$—C(=O)—, —C(=O)NH—[(CH$_2$CH$_2$O)$_{1-10}$—(CH$_2$)$_{1-5}$—C(=O)]$_{1-5}$NH(CH$_2$)$_{2-30}$—, —C(=O)—, —(CH$_2$)$_{1-30}$—NHC(=O)—, —(CH$_2$)$_{1-30}$C(=O)—, —NHC(=O)NH(CH$_2$)$_{2-30}$—, —(CH$_2$)$_{1-30}$—NHC(=O)NH(CH$_2$)$_{2-30}$—, —(CH$_2$)$_{0-30}$C(=O)NH(CH$_2$)$_{2-30}$—NHC(=O)—(CH$_2$)$_{0-30}$—, —(CH$_2$)$_{0-30}$C(=O)NH(CH$_2$CH$_2$O)$_{1-30}$—CH$_2$CH$_2$NHC(=O)—(CH$_2$)$_{0-30}$—, or —NH(CH$_2$)$_{2-30}$—,

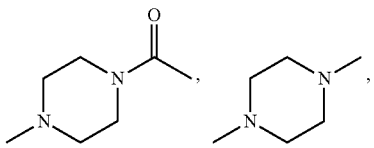

and combinations thereof, and
R$^3$ represents a property-modifying group;
R$^4$ represents hydrogen or C$_{1-6}$-alkyl;
R$^5$ represents —CH$_2$— or —C(=O)—,
or pharmaceutically acceptable salts, prodrugs and solvates thereof.

Embodiment 2: A compound according to embodiment 1, wherein R$^1$ represents arylene or a heteroarylene, optionally substituted with a C$_{1-6}$-alkyl, halogen, cyano, nitro, hydroxyl, carboxyl, or C$_{5-22}$-aryl group.

Embodiment 3: A compound according to embodiment 2, wherein R$^1$ represents arylene or a heteroarylene, optionally substituted with a C$_{1-6}$-alkyl, halogen, cyano, nitro, hydroxyl, carboxyl, or C$_{6-18}$-aryl group.

Embodiment 4: A compound according to embodiment 3, wherein R$^1$ represents arylene or a heteroarylene, optionally substituted with a C$_{1-6}$-alkyl, halogen, cyano, nitro, hydroxyl, carboxyl, or C$_{4-16}$-aryl group.

Embodiment 5: A compound according to embodiment 4, wherein R$^1$ represents arylene or a heteroarylene, optionally substituted with a C$_{1-6}$-alkyl, halogen, cyano, nitro, hydroxyl, carboxyl, or C$_{6-8}$-aryl group.

Embodiment 6: A compound according to any of embodiments 1 to 5, wherein R$^1$ represents a C$_{5-22}$-arylene, optionally substituted as described above.

Embodiment 7: A compound according to embodiment 6, wherein R$^1$ represents a C$_{6-18}$-arylene, optionally substituted as described above.

Embodiment 8: A compound according to embodiment 7, wherein R$^1$ represents a C$_{6-14}$-arylene, optionally substituted as described above.

Embodiment 9: A compound according to any of embodiments 1 to 5, wherein R$^1$ represents a C$_{5-22}$-heteroarylene, optionally substituted as described above.

Embodiment 10: A compound according to embodiment 9, wherein R$^1$ represents a C$_{6-18}$-heteroarylene, optionally substituted as described above.

Embodiment 11: A compound according to embodiment 10, wherein R$^1$ represents a C$_{6-14}$-heteroarylene, optionally substituted as described above.

Embodiment 12: A compound according to any of embodiments 1 to 5, wherein R$^1$ represents a C$_{6-8}$-arylene, a C$_{12-18}$-arylene or a C$_{5-18}$-heteroarylene, optionally substituted as described above.

Embodiment 13: A compound according to embodiment 12, wherein R$^1$ represents a phenylene or a pyridylene group.

Embodiment 14: A compound according to embodiment 13, wherein $R^1$ represents 1,4-phenylene.

Embodiment 15: A compound according to any of embodiments 1 to 14, in which $R^2$ represents a bond, —C(=O)—, —C(=O)—NH—, or

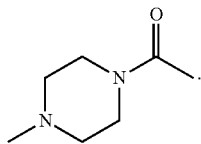

Embodiment 16: A compound according to embodiment 15, wherein $R^2$ represents —C(=O)—NH—.

Embodiment 17: A compound according to any of embodiments 1 to 16, wherein the property modified by the property-modifying group is the functional in vivo half-life of the peptide compound.

Embodiment 18: A compound according to embodiment 17, wherein the functional in vivo half-life of the peptide compound is increased as compared to the peptide compound without the property-modifying group.

Embodiment 19: A method according to embodiment 18, wherein the approximate functional in vivo half-life of the peptide is increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Embodiment 20: A compound according to any of embodiments 1 to 19, wherein
$R^3$ represents a linear or branched polymer or oligomer, optionally substituted with acidic or negatively charged functional groups, with basic or cationic functional groups, or with combinations thereof; or
$R^3$ represents a linear or branched $C_{10}$-$C_{90}$ alkyl group, optionally substituted with acidic or negatively charged functional groups, with basic or cationic functional groups, or with combinations thereof.

Embodiment 21: A compound according to embodiment 20, wherein $R^3$ represents a linear or branched polyethylene glycol (PEG), poloxamer, poly(lactic acid), poly(lactide)-glycolide copolymer, oligosaccharide, peptides, proteins, or combinations thereof, optionally substituted with acidic or negatively charged functional groups, with basic or cationic functional groups, or with combinations thereof.

Embodiment 22: A compound according to embodiment 21, wherein $R^3$ represents a linear or branched oligosaccharide selected from such as cellulose, starch, hyaluronic acid, agar, hydroxyethyl cellulose, hydroxyethyl starch, or pentosan or combinations thereof, optionally substituted with acidic or negatively charged functional groups, with basic or cationic functional groups, or with combinations thereof.

Embodiment 23: A compound according to embodiment 21, wherein $R^3$ represents a linear or branched polyethylene glycol of a molecular weight of 5-60 kDa.

Embodiment 24: A compound according to according to embodiment 20, wherein $R^3$ represents a linear or branched $C_{10}$-$C_{90}$ alkyl group, optionally substituted with acidic or negatively charged functional groups, with basic or cationic functional groups, or with combinations thereof.

Embodiment 25: A compound according to embodiment 24, wherein $R^3$ represents $CH_3$—$(CH_2)_{10-30}$—, (5-tetrazolyl)-$(CH_2)_{10-30}$—, or $HO_2C$—$(CH_2)_{10-30}$—.

Embodiment 26: A compound according to according to embodiment 20, wherein $R^3$ is selected from

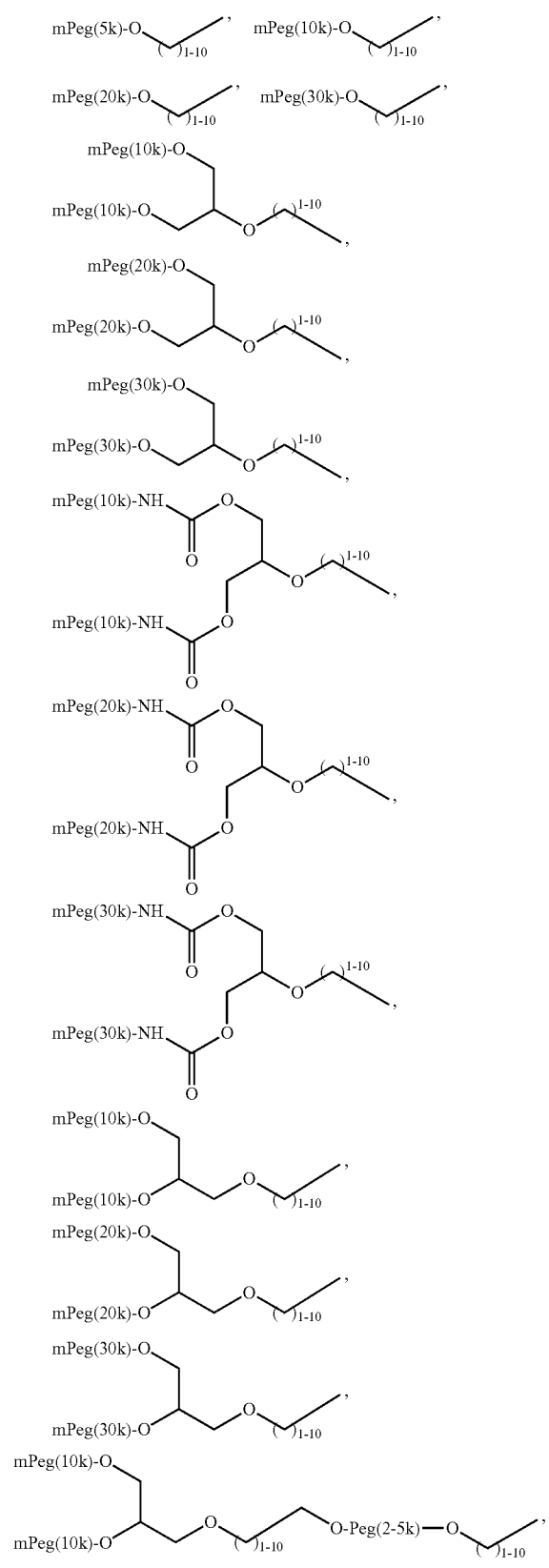

-continued

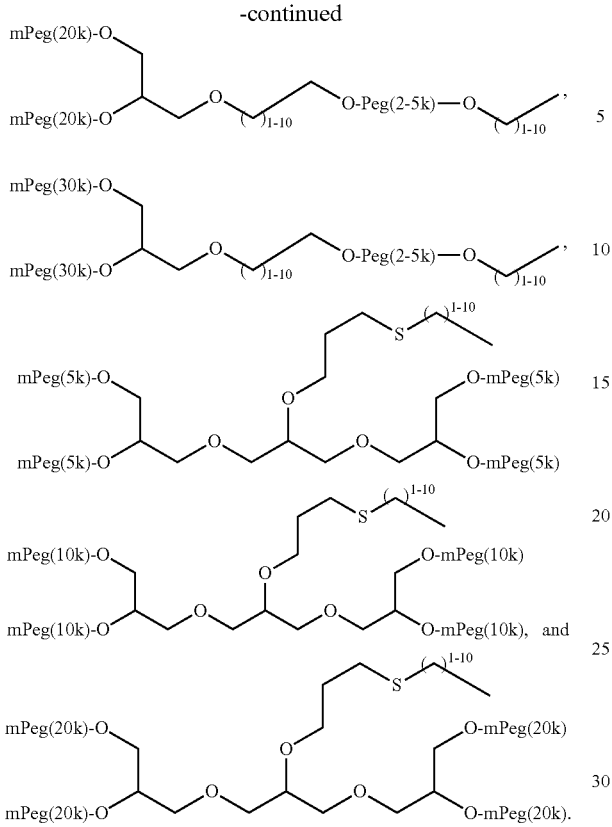

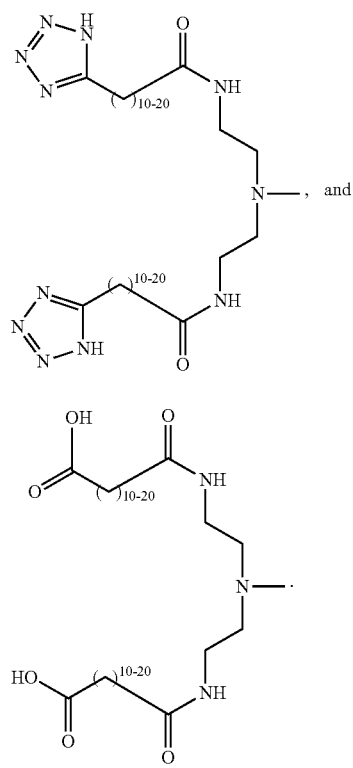

Embodiment 27: A compound according to according to embodiment 20, wherein $R^3$ is selected from Me-$(CH_2)_{12}$—, Me-$(CH_2)_{14}$—, Me-$(CH_2)_{16}$—, Me-$(CH_2)_{18}$—, (5-tetrazolyl)-$(CH_2)_{12}$—, (5-tetrazolyl)-$(CH_2)_{13}$—, (5-tetrazolyl)-$(CH_2)_{14}$—, (5-tetrazolyl)-$(CH_2)_{15}$—, (5-tetrazolyl)-$(CH_2)_{16}$—, (5-tetrazolyl)-$(CH_2)_{17}$—, (5-tetrazolyl)-$(CH_2)_{18}$—, $HO_2C$—$(CH_2)_{14}$—, $HO_2C$—$(CH_2)_{15}$—, $HO_2C$—$(CH_2)_{16}$—, $HO_2C$—$(CH_2)_{17}$—, $HO_2C$—$(CH_2)_{18}$—, (5-tetrazolyl)$_2$CH—$(CH_2)_{14}$—, Embodiment 28: A compound according to any of embodiments 1 to 27, in which $R^4$ represents hydrogen.

Embodiment 29: A compound according to any of embodiments 1 to 27, in which $R^4$ represents $C_{1-6}$-alkyl.

Embodiment 30: A compound according to any of embodiments 1 to 29, in which $R^5$ represents —$CH_2$—.

Embodiment 31: A compound according to any of embodiments 1 to 29, in which $R^5$ represents —$C(=O)$—.

Embodiment 32: A compound according to embodiment 1 having a structural formula selected from

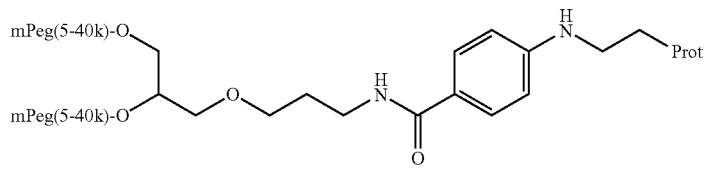

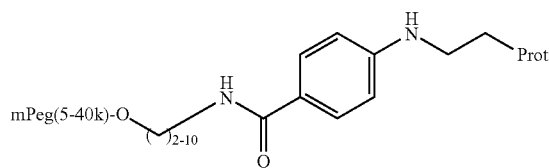

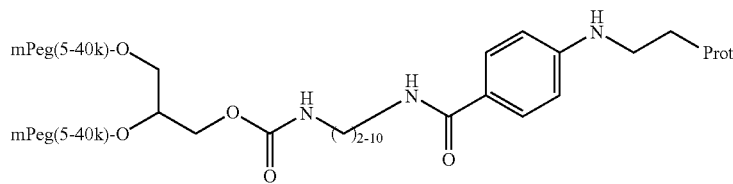

-continued
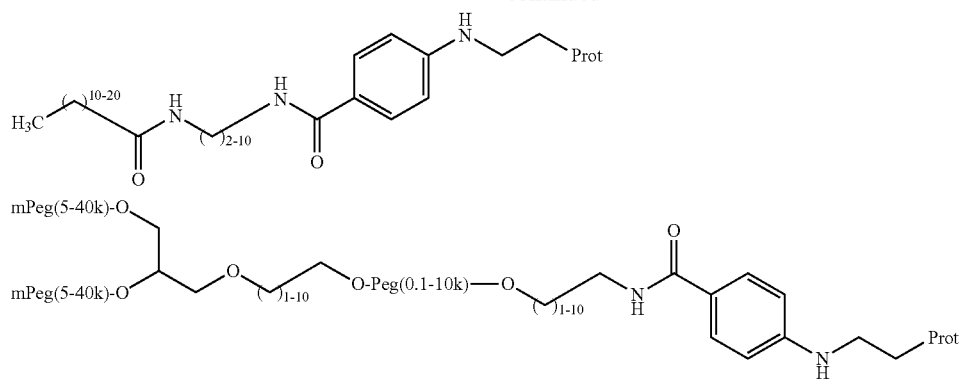
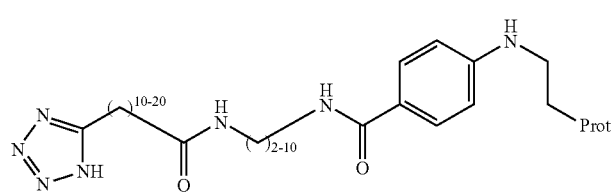
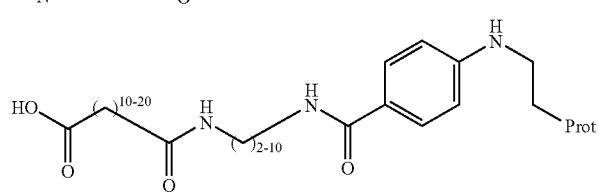
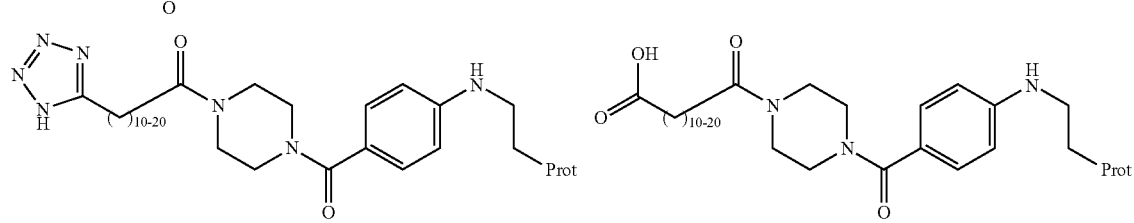
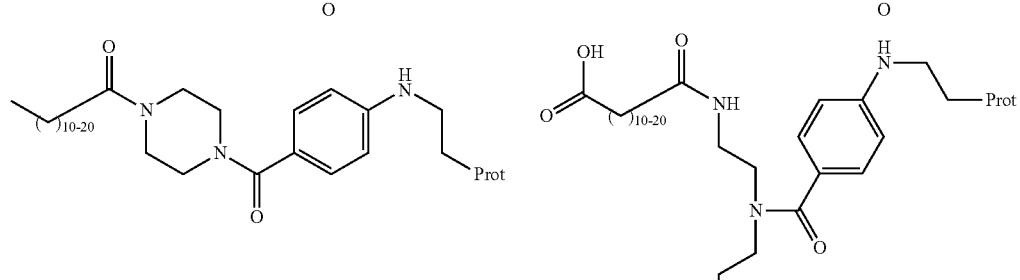
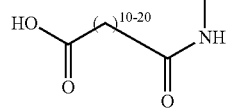
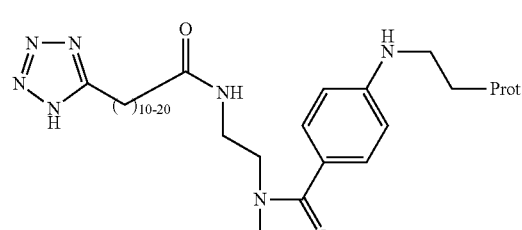
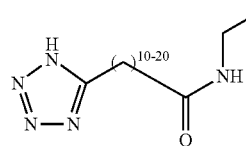

or pharmaceutically acceptable salts, prodrugs and solvates thereof.

Embodiment 33: A compound according to any of embodiments 1 to 32, wherein Prot is obtainable from a peptide-derived aldehyde or ketone of formula

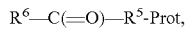

$R^6$—C(=O)—$R^5$-Prot, wherein
$R^5$ is as described above, and
$R^6$ represents hydrogen or an optionally substituted α-carbon atom.

Embodiment 34: A compound according to embodiment 33, wherein $R^6$ represents hydrogen, $C_{1-6}$-alkyl or $C_{1-6}$-cycloalkyl.

Embodiment 35: A compound according to embodiment 34, wherein $R^6$ represents hydrogen, methyl, ethyl, propyl, cyclopropyl, cyclobutyl, cyclopentyl, or cyclohexyl.

Embodiment 36: A compound according to embodiment 35, wherein $R^6$ represents hydrogen or methyl.

Embodiment 37: A compound according to any of embodiments 1 to 36, wherein Prot represents a peptide-derived radical generated by the formal removal of a hydrogen atom from an amino group (—$NH_2$) of a peptide or protein, and wherein said amino group is the N-terminal amino group of the peptide, a side-chain amino group of lysine residue in the peptide, or a side-chain amino group of glutamine or asparagine ($CONH_2$) residue in the peptide.

Embodiment 38: A compound according to embodiment 37, wherein Prot represents a peptide radical formally generated by removal of one hydrogen atom from the N-terminal amino group.

Embodiment 39: A compound according to embodiment 37, wherein Prot represents a peptide radical formally generated by removal of one hydrogen atom from a side-chain amino group of lysine residue in the peptide.

Embodiment 40: A compound according to embodiment 37, wherein Prot represents a peptide radical formally generated by removal of one hydrogen atom from a side-chain amino group of glutamine or asparagine residue in the peptide.

Embodiment 41: A compound according to any of embodiments 1 to 40, wherein Prot represents a growth hormone-derived radical.

Embodiment 42: A compound according to embodiment 41, wherein Prot represents a growth hormone-derived radical with an amino acid sequence having at least 80% identity with the amino acid sequence in SEQ ID No. 1.

Embodiment 43: A compound according to embodiment 42, wherein Prot represents a growth hormone-derived radical with an amino acid sequence having at least 85% identity with the amino acid sequence in SEQ ID No. 1.

Embodiment 44: A compound according to embodiment 43, wherein Prot represents a growth hormone-derived radical with an amino acid sequence having at least 90% identity with the amino acid sequence in SEQ ID No. 1.

Embodiment 45: A compound according to embodiment 44, wherein Prot represents a growth hormone-derived radical with an amino acid sequence having at least 95% identity with the amino acid sequence in SEQ ID No. 1.

Embodiment 46: A compound according to embodiment 41, wherein Prot represents a human growth hormone-derived radical.

Embodiment 47: A compound according to embodiment 46, wherein Prot represents a human growth hormone-derived radical comprising the amino acid sequence of SEQ ID No. 1.

Embodiment 48: A compound according to embodiment 40, wherein Prot represents a growth hormone-derived radical.

Embodiment 49: A compound according to embodiment 48, wherein Prot represents a growth hormone-derived radical with an amino acid sequence having at least 80% identity with the amino acid sequence in SEQ ID No. 1.

Embodiment 50: A compound according to embodiment 49, wherein Prot represents a growth hormone-derived radical with an amino acid sequence having at least 85% identity with the amino acid sequence in SEQ ID No. 1.

Embodiment 51: A compound according to embodiment 50, wherein Prot represents a growth hormone-derived radical with an amino acid sequence having at least 90% identity with the amino acid sequence in SEQ ID No. 1.

Embodiment 52: A compound according to embodiment 51, wherein Prot represents a growth hormone-derived radical with an amino acid sequence having at least 95% identity with the amino acid sequence in SEQ ID No. 1.

Embodiment 53: A compound according to embodiment 48, wherein Prot represents a human growth hormone-derived radical.

Embodiment 54: A compound according to embodiment 53, wherein Prot represents a human growth hormone-derived radical comprising the amino acid sequence of SEQ ID No. 1.

Embodiment 55: A compound according to any of embodiments 48 to 54, wherein the Prot radical represents a peptide radical formally generated by removal of one hydrogen atom from the side-chain aminocarbonyl group ($H_2N$—CO—) of the glutamine at the position corresponding to position 40 in SEQ ID No. 1.

Embodiment 56: A compound according to any of embodiments 48 to 54, wherein the Prot radical represents a peptide radical formally generated by removal of one hydrogen atom from the side-chain aminocarbonyl group ($H_2N$—CO—) of the glutamine at the position corresponding to position 141 in SEQ ID No. 1.

Embodiment 57: A compound according to any of embodiments 41 to 56, wherein the peptide has an activity of at least 20% of the activity of hGH in assay (I).

Embodiment 58: A compound according to any of embodiments 41 to 56, wherein the peptide has an activity of at least 40% of the activity of hGH in assay (I).

Embodiment 59: A compound according to any of embodiments 41 to 56, wherein the peptide has an activity of at least 60% of the activity of hGH in assay (I).

Embodiment 60: A compound according to any of embodiments 41 to 56, wherein the peptide has an activity of at least 80% of the activity of hGH in assay (I).

Embodiment 61: A compound according to embodiment 1, wherein the peptide is

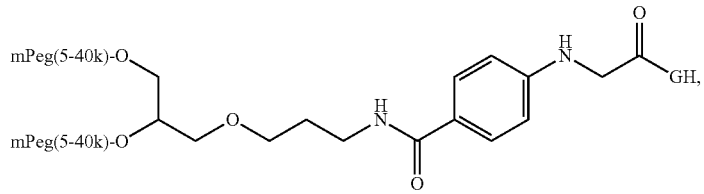

-continued
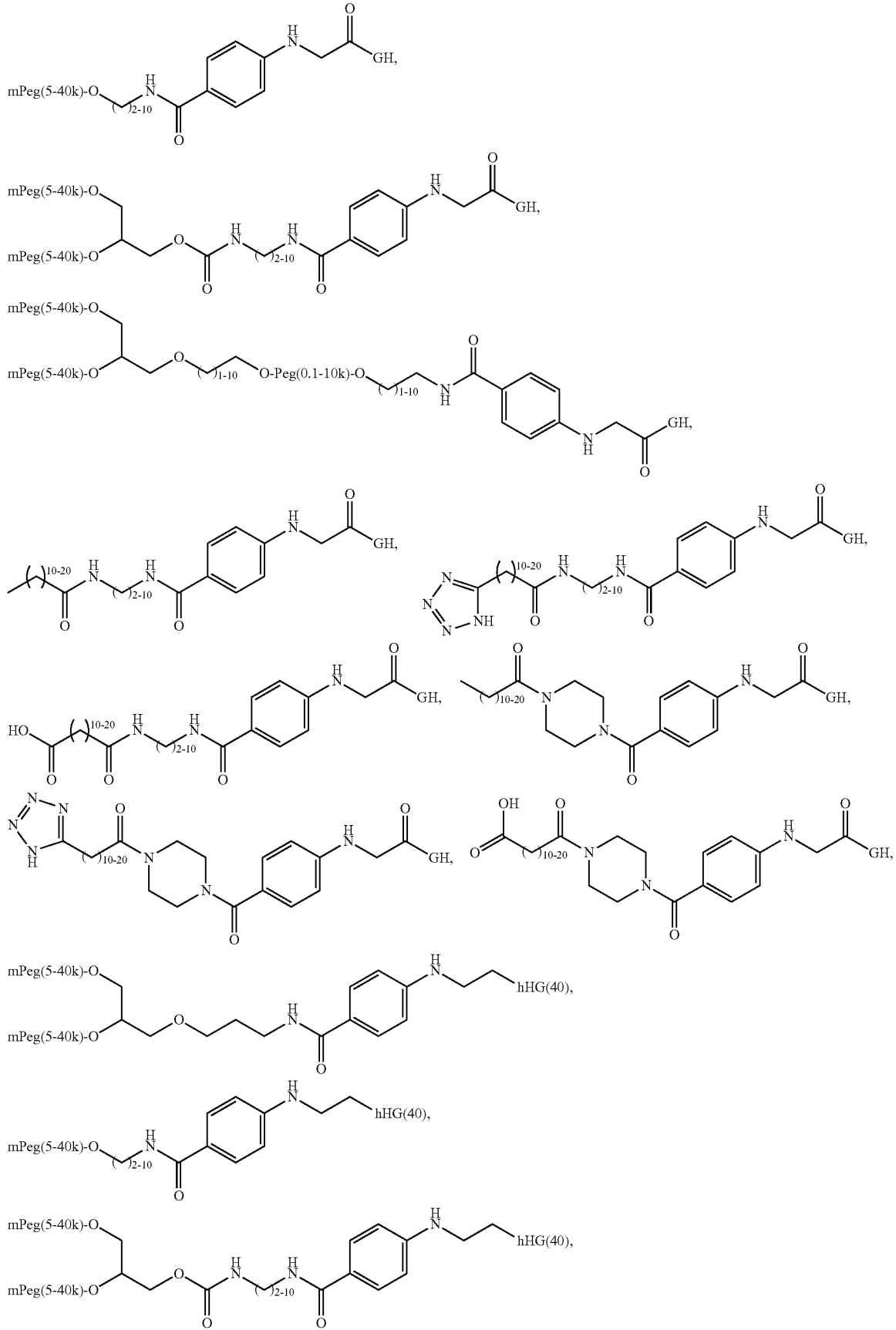

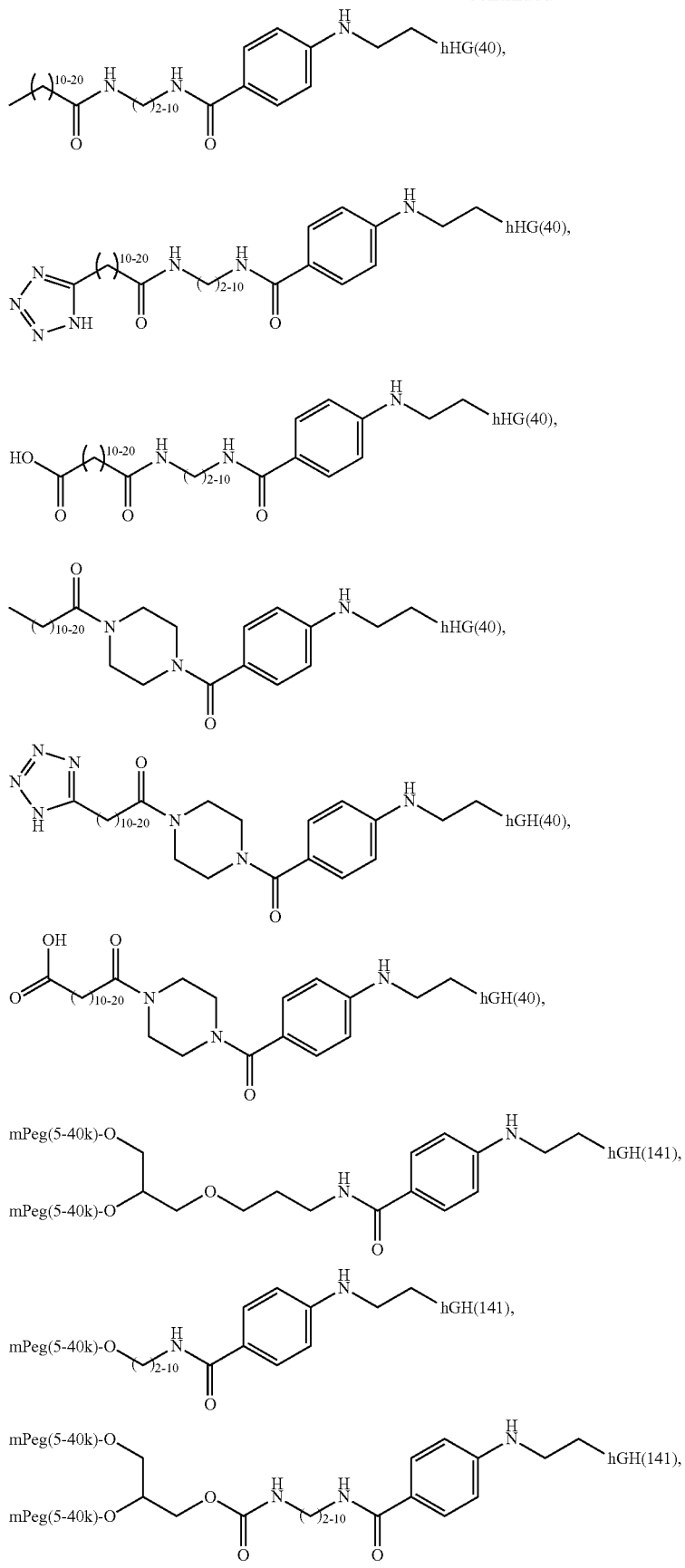

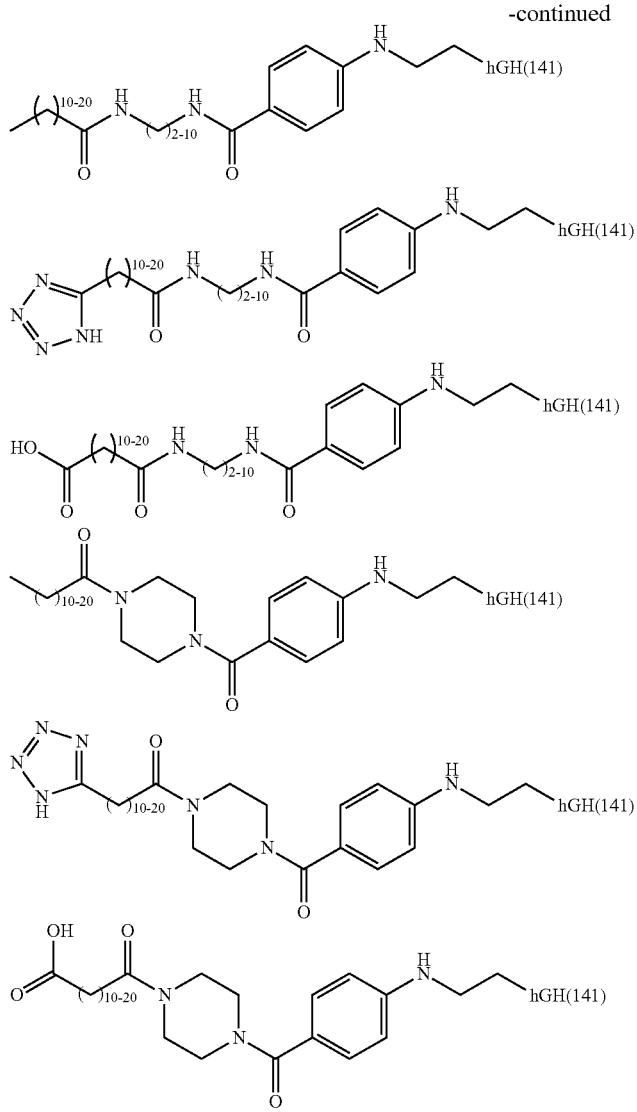

or pharmaceutically acceptable salts, prodrugs and solvates thereof.

Embodiment 62: A compound according to any of embodiments 1 to 40, wherein Prot represents an antibody-derived radical.

Embodiment 63: A compound according to any of embodiments 1 to 40, wherein Prot represents a radical derived from a fragment of an antibody.

Embodiment 64: A method for preparing a peptide compound comprising a property-modifying group, said method comprising the steps of
(a) treatment of an aldehyde or ketone derived from the peptide compound with a property-modifying group-derived aniline or heteroarylamine to yield an imine or a hemiaminal,
(b) treatment of this imine or hemiaminal with a suitable reducing agent, such as NaCNBH$_3$, to yield a secondary amine.

Embodiment 65: A method according to embodiment 64, wherein the property modified by the property-modifying group of the peptide compound comprising a property-modifying group when compared to the peptide compound without said property-modifying group is the functional in vivo half-life of the peptide compound.

Embodiment 66: A method according to embodiment 65, wherein the functional in vivo half-life of the peptide compound is increased as compared to the peptide compound without the property-modifying group.

Embodiment 67: A method according to embodiment 66, wherein the approximate functional in vivo half-life of the peptide has been increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Embodiment 68: A method according to any of embodiments 64 to 67, wherein the peptide compound comprising a property-modifying group is a compound according to any of embodiments 1 to 63.

Embodiment 69: A method according to any of embodiments 64 to 68, wherein the peptide-derived aldehyde or ketone is prepared by periodate-mediated oxidation of a peptide compound containing a 2-aminoethanol substructure.

Embodiment 70: A method according to any of embodiments 64 to 68, wherein the peptide-derived aldehyde or ketone is prepared by hydrolysis of an acetal or a hemiacetal.

Embodiment 71: A method according to any of embodiments 64 to 68, wherein the peptide-derived aldehyde is prepared by periodate-mediated oxidation of a peptide containing serine or threonine as the N-terminal amino acid.

Embodiment 72: A method according to any of embodiments 64 to 68, wherein the peptide-derived aldehyde is prepared by periodate-mediated oxidation of a peptide transaminated enzymatically with 1,3-diamino-2-propanol.

Embodiment 73: A method according to any of embodiments 64 to 68, wherein the peptide-derived aldehyde or ketone is prepared by feeding a genetically modified or unmodified organism producing said peptide with an unnatural amino acid containing an aldehyde or ketone functionality, wherein said amino acid will be incorporated into the peptide, followed by isolation and purification of the peptide into which the unnatural amino acid has been incorporated.

Embodiment 74: A method according to embodiment 73, wherein the unnatural amino acid is (acetylphenyl)alanine or (formylphenyl)alanine.

Embodiment 75: A method according to embodiment 73 or embodiment 74, wherein the mRNA encoding the peptide comprises at least one codon encoding phenylalanine.

Embodiment 76: A method according to any of embodiments 64 to 75, wherein the property-modifying group-derived aniline or heteroarylamine is of the formula $$R^3-R^2-R^1-NH_2 \quad (III)$$

wherein $R^1$, $R^2$, and $R^3$ are as defined in embodiment 1.

Embodiment 77: A method according to embodiment 76, wherein $R^1$ represents arylene or a heteroarylene, optionally substituted with a $C_{1-6}$-alkyl, halogen, cyano, nitro, hydroxyl, carboxyl, or $C_{5-22}$-aryl group.

Embodiment 78: A method according to embodiment 77, wherein $R^1$ represents arylene or a heteroarylene, optionally substituted with a $C_{1-6}$-alkyl, halogen, cyano, nitro, hydroxyl, carboxyl, or $C_{6-18}$-aryl group.

Embodiment 79: A method according to embodiment 78, wherein $R^1$ represents arylene or a heteroarylene, optionally substituted with a $C_{1-6}$-alkyl, halogen, cyano, nitro, hydroxyl, carboxyl, or $C_{4-16}$-aryl group.

Embodiment 80: A method according to embodiment 79, wherein $R^1$ represents arylene or a heteroarylene, optionally substituted with a $C_{1-6}$-alkyl, halogen, cyano, nitro, hydroxyl, carboxyl, or $C_{6-8}$-aryl group.

Embodiment 81: A method according to any of embodiments 76 to 80, wherein $R^1$ represents a $C_{5-22}$-arylene, optionally substituted as described above.

Embodiment 82: A method according to embodiment 81, wherein $R^1$ represents a $C_{6-18}$-arylene, optionally substituted as described above.

Embodiment 83: A method according to embodiment 82, wherein $R^1$ represents a $C_{6-14}$-arylene, optionally substituted as described above.

Embodiment 84: A method according to any of embodiments 76 to 80, wherein $R^1$ represents a $C_{5-22}$-heteroarylene, optionally substituted as described above.

Embodiment 85: A method according to embodiment 84, wherein $R^1$ represents a $C_{16-18}$-heteroarylene, optionally substituted as described above.

Embodiment 86: A method according to embodiment 85, wherein $R^1$ represents a $C_{6-14}$-heteroarylene, optionally substituted as described above.

Embodiment 87: A method according to any of embodiments 76 to 80, wherein $R^1$ represents a $C_{6-8}$-arylene, a $C_{12-18}$-arylene or a $C_{5-18}$-heteroarylene, optionally substituted as described above.

Embodiment 88: A method according to embodiment 87, wherein $R^1$ represents a phenylene or a pyridylene group.

Embodiment 89: A method according to embodiment 88, in which $R^1$ represents 1,4-phenylene.

Embodiment 90: A method according to any of embodiments 76 to 89, wherein $R^2$ represents a bond, —C(=O)—NH—, or

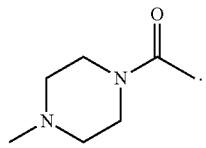

Embodiment 91: A method according to embodiment 90, wherein $R^2$ represents —C(=O)—NH—.

Embodiment 92: A method according to any of embodiments 76 to 91, wherein
$R^3$ represents a linear or branched polymer or oligomer, optionally substituted with acidic or negatively charged functional groups; or
$R^3$ represents a linear or branched $C_{10}C_{90}$ alkyl group, optionally substituted with acidic or negatively charged functional groups.

Embodiment 93: A method according to embodiment 92, wherein $R^3$ represents a linear or branched polyethylene glycol (PEG), poloxamer, poly(lactic acid), poly(lactide)-glycolide copolymer, oligosaccharide, peptides, proteins, or combinations thereof.

Embodiment 94: A method according to embodiment 93, wherein $R^3$ represents a linear or branched oligosaccharide selected from such as cellulose, starch, hyaluronic acid, agar, hydroxyethyl cellulose, hydroxyethyl starch, or pentosan or combinations thereof.

Embodiment 95: A method according to embodiment 93, wherein $R^3$ represents a linear or branched polyethylene glycol of a molecular weight of 5-60 kDa.

Embodiment 96: A method according to embodiment 92, wherein $R^3$ represents $CH_3-(CH_2)_{10-30}-$, (5-tetrazolyl)-$(CH_2)_{10-30}-$, or $HO_2C-(CH_2)_{10-30}-$.

Embodiment 97: A method according to embodiment 92, wherein $R^3$ is selected from

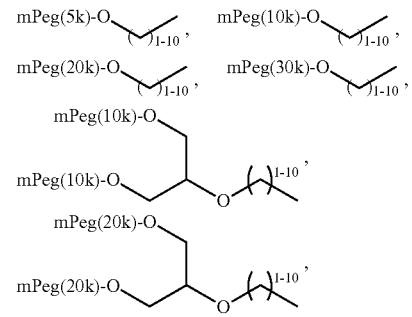

-continued

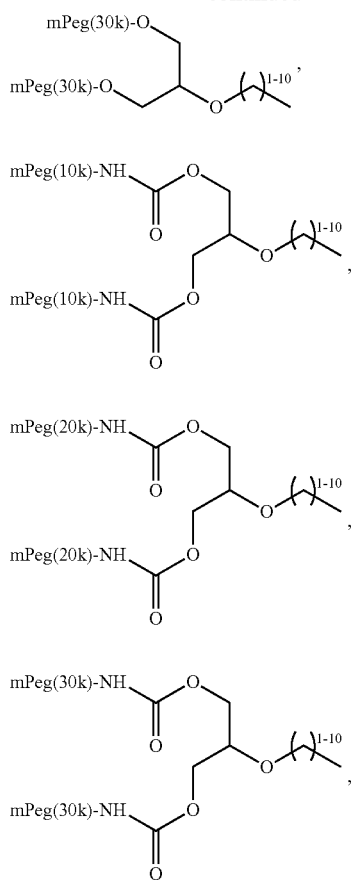

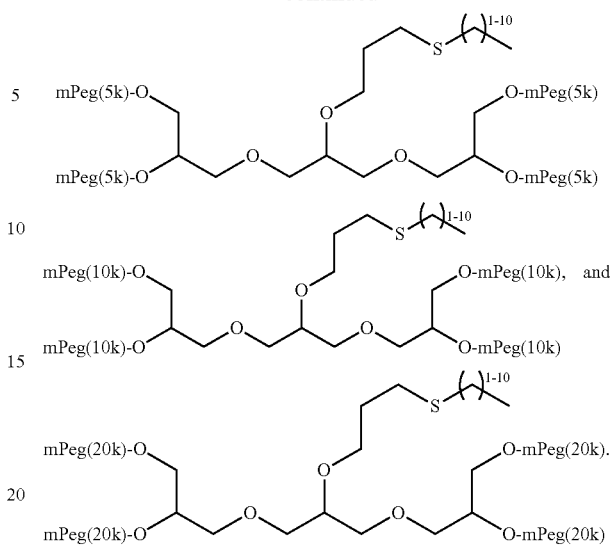

Embodiment 98: A method according to embodiment 92, wherein $R^3$ is selected from Me-$(CH_2)_{12}$—, Me-$(CH_2)_{14}$—, Me-$(CH_2)_{16}$—, Me-$(CH_2)_{18}$—, (5-tetrazolyl)-$(CH_2)_{12}$—, (5-tetrazolyl)-$(CH_2)_{13}$—, (5-tetrazolyl)-$(CH_2)_{14}$—, (5-tetrazolyl)-$(CH_2)_{15}$—, (5-tetrazolyl)-$(CH_2)_{16}$—, (5-tetrazolyl)-$(CH_2)_{17}$—, (5-tetrazolyl)-$(CH_2)_{18}$—, $HO_2C$—$(CH_2)_{14}$—, $HO_2C$—$(CH_2)_{15}$—, $HO_2C$—$(CH_2)_{16}$—, $HO_2C$—$(CH_2)_{17}$—, $HO_2C$—$(CH_2)_{18}$—, (5-tetrazolyl)$_2$CH—$(CH_2)_{14}$—,

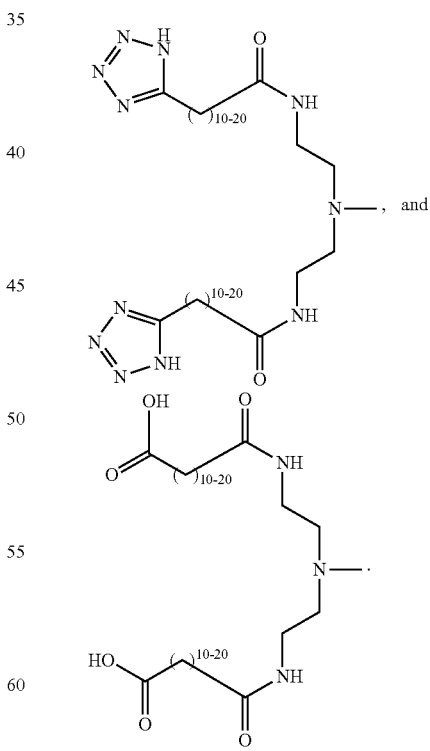

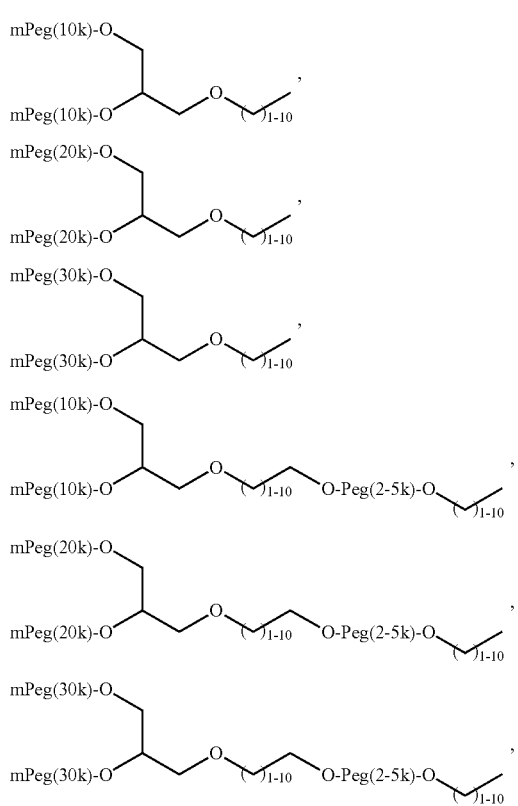

Embodiment 99: A method according to embodiment 76, wherein the property-modifying group-derived aniline or heteroarylamine is selected from

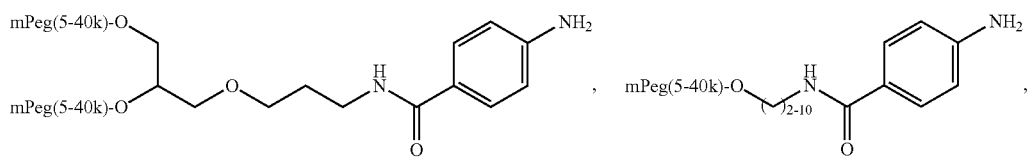
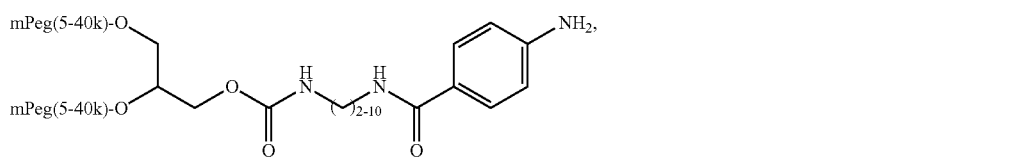
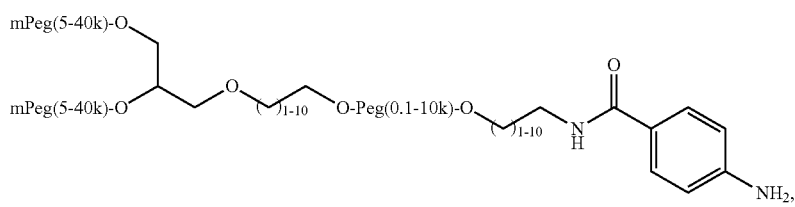
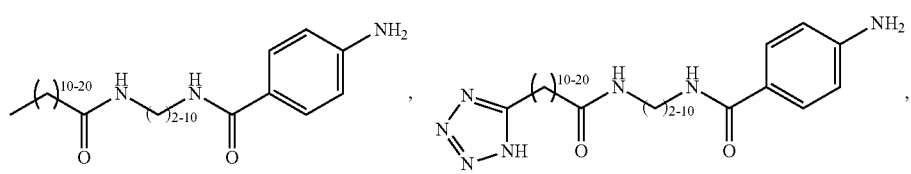
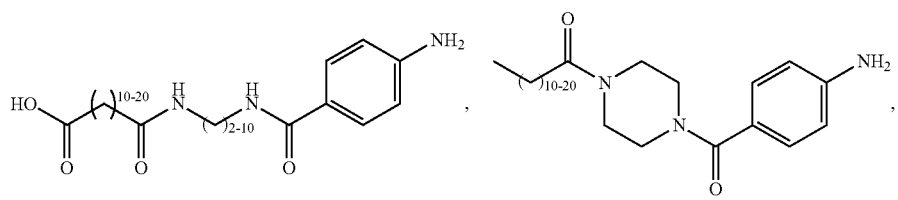
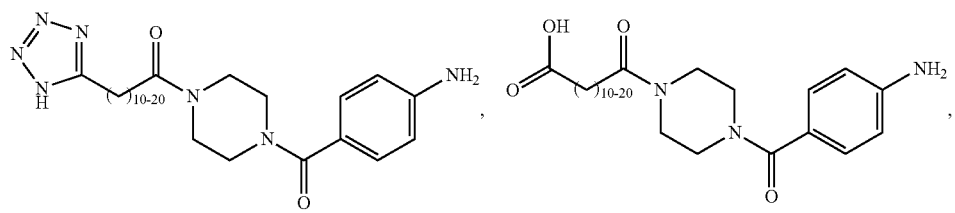
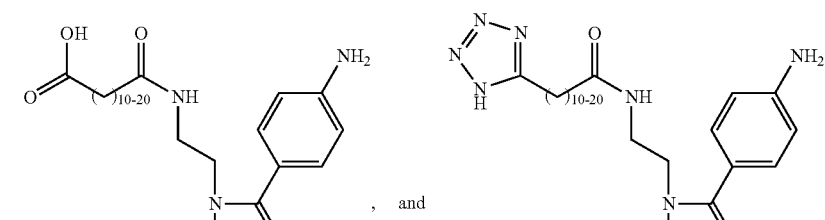
, and
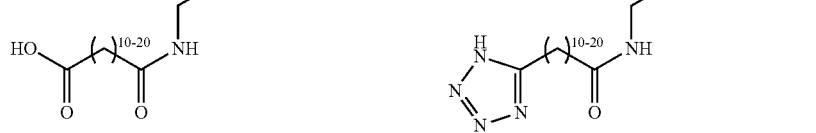
.

Embodiment 100: A method according to any of embodiments 64 to 99, wherein the peptide-derived aldehyde or ketone is of the formula $$R^6-C(=O)-R^5\text{-Prot},$$

wherein
Prot is as described in embodiment 1,
$R^5$ is —CH$_2$— or —C(=O)—, and
$R^6$ represents hydrogen or an optionally substituted α-carbon atom.

Embodiment 101: A method according to embodiment 100, in which $R^5$ represents —CH$_2$—.

Embodiment 102: A method according to embodiment 100, in which $R^5$ represents —C(=O)—.

Embodiment 103: A method according to any of embodiments 100 to 102, wherein $R^6$ represents hydrogen, $C_{1-6}$-alkyl or $C_{1-6}$-cycloalkyl.

Embodiment 104: A method according to embodiment 103, wherein $R^6$ represents hydrogen, methyl, ethyl, propyl, cyclopropyl, cyclobutyl, cyclopentyl, or cyclohexyl.

Embodiment 105: A method according to embodiment 104, wherein $R^6$ represents hydrogen or methyl.

Embodiment 106: A method according to any of embodiments 64 to 105, wherein said peptide is a growth hormone.

Embodiment 107: A method according to embodiment 106, wherein Prot represents a growth hormone-derived radical with an amino acid sequence having at least 80% identity with the amino acid sequence in SEQ ID No. 1.

Embodiment 108: A method according to embodiment 107, wherein Prot represents a growth hormone-derived radical with an amino acid sequence having at least 85% identity with the amino acid sequence in SEQ ID No. 1.

Embodiment 109: A method according to embodiment 108, wherein Prot represents a growth hormone-derived radical with an amino acid sequence having at least 90% identity with the amino acid sequence in SEQ ID No. 1.

Embodiment 110: A method according to embodiment 109, wherein Prot represents a growth hormone-derived radical with an amino acid sequence having at least 95% identity with the amino acid sequence in SEQ ID No. 1.

Embodiment 111: A method according to any of embodiments 106 to 110, wherein the peptide has least 20%, such as at least 40%, such as at least 60%, such as at least 80% of the growth hormone activity of hGH as determined in assay I herein.

Embodiment 112: A method according to embodiment 106, wherein said growth hormone is human growth hormone.

Embodiment 113: A method according to embodiment 106, wherein said growth hormone comprises the amino acid sequence of SEQ ID No. 1.

Embodiment 114: A method according to any of embodiments 106 to 113, wherein the property-modifying group is conjugated to the peptide on the position corresponding to position 40 in SEQ ID No. 1.

Embodiment 115: A method according to embodiment 106 to 113, wherein the property-modifying group is conjugated to the peptide on the position corresponding to position 141 in SEQ ID No. 1.

Embodiment 116: A compound of formula (III)

$$R^3-R^2-R^1-NH_2 \quad (III)$$

wherein $R^1$, $R^2$, and $R^3$ are as defined in embodiment 1.

Embodiment 117: A compound according to embodiment 116, wherein $R^1$ represents arylene or a heteroarylene, optionally substituted with a $C_{1-6}$-alkyl, halogen, cyano, nitro, hydroxyl, carboxyl, or $C_{5-22}$-aryl group.

Embodiment 118: A compound according to embodiment 117, wherein $R^1$ represents arylene or a heteroarylene, optionally substituted with a $C_{1-6}$-alkyl, halogen, cyano, nitro, hydroxyl, carboxyl, or $C_{6-18}$-aryl group.

Embodiment 119: A compound according to embodiment 118, wherein $R^1$ represents arylene or a heteroarylene, optionally substituted with a $C_{1-6}$-alkyl, halogen, cyano, nitro, hydroxyl, carboxyl, or $C_{4-16}$-aryl group.

Embodiment 120: A compound according to embodiment 119, wherein $R^1$ represents arylene or a heteroarylene, optionally substituted with a $C_{1-6}$-alkyl, halogen, cyano, nitro, hydroxyl, carboxyl, or $C_{6-8}$-aryl group.

Embodiment 121: A compound according to any of embodiments 116 to 120, wherein $R^1$ represents a $C_{5-22}$-arylene, optionally substituted as described above.

Embodiment 122: A compound according to embodiment 121, wherein $R^1$ represents a $C_{6-18}$-arylene, optionally substituted as described above.

Embodiment 123: A compound according to embodiment 122, wherein $R^1$ represents a $C_{6-14}$-arylene, optionally substituted as described above.

Embodiment 124: A compound according to any of embodiments 116 to 120, wherein $R^1$ represents a $C_{5-22}$-heteroarylene, optionally substituted as described above.

Embodiment 125: A compound according to embodiment 124, wherein $R^1$ represents a $C_{6-18}$-heteroarylene, optionally substituted as described above.

Embodiment 126: A compound according to embodiment 125, wherein $R^1$ represents a $C_{6-14}$-heteroarylene, optionally substituted as described above.

Embodiment 127: A compound according to any of embodiments 116 to 120,
wherein $R^1$ represents a $C_{6-8}$-arylene, a $C_{12-18}$-arylene or a $C_{5-18}$-heteroarylene, optionally substituted as described above.

Embodiment 128: A compound according to embodiment 127, wherein $R^1$ represents a phenylene or a pyridylene group.

Embodiment 129: A compound according to embodiment 128, wherein $R^1$ represents 1,4-phenylene.

Embodiment 130: A compound according to any of embodiments 116 to 129, in which $R^2$ represents a bond, —C(=O)—, —C(=O)—NH—, or

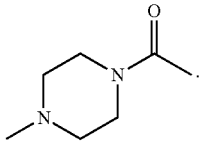

Embodiment 131: A compound according to embodiment 130, wherein $R^2$ represents —C(=O)—NH—.

Embodiment 132: A compound according to any of embodiments 116 to 131, wherein the property modified by the property-modifying group is the functional in vivo half-life of the peptide compound.

Embodiment 133: A compound according to embodiment 132, wherein the functional in vivo half-life of the peptide compound is increased as compared to the peptide compound without the property-modifying group.

Embodiment 134: A compound according to embodiment 133, wherein the approximate functional in vivo half-life of the peptide has been increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Embodiment 135: A compound according to any of embodiments 116 to 134, wherein $R^3$ represents a linear or branched polymer or oligomer, optionally substituted with acidic or negatively charged functional groups, with basic or cationic functional groups, or with combinations thereof; or $R^3$ represents a linear or branched $C_{10}C_{90}$ alkyl group, optionally substituted with acidic or negatively charged functional groups, with basic or cationic functional groups, or with combinations thereof.

Embodiment 136: A compound according to embodiment 135, wherein $R^3$ represents a linear or branched polyethylene glycol (PEG), poloxamer, poly(lactic acid), poly(lactide)-glycolide copolymer, oligosaccharide, peptides, proteins, or combinations thereof, optionally substituted with acidic or negatively charged functional groups, with basic or cationic functional groups, or with combinations thereof.

Embodiment 137: A compound according to embodiment 136, wherein $R^3$ represents a linear or branched oligosaccharide selected from such as cellulose, starch, hyaluronic acid, agar, hydroxyethyl cellulose, hydroxyethyl starch, or pentosan or combinations thereof, optionally substituted with acidic or negatively charged functional groups, with basic or cationic functional groups, or with combinations thereof.

Embodiment 138: A compound according to embodiment 136, wherein $R^3$ represents a linear or branched polyethylene glycol of a molecular weight of 5-60 kDa.

Embodiment 139: A compound according to any of embodiments 116 to 135, wherein $R^3$ represents $CH_3—(CH_2)_{10-30}—$, (5-tetrazolyl)-$(CH_2)_{10-30}—$, or $HO_2C—(CH_2)_{10-30}—$.

Embodiment 140: A compound according to embodiment 135, wherein $R^3$ is selected from

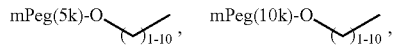
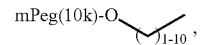
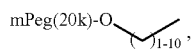
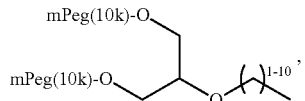
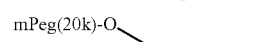
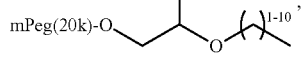
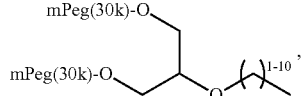

-continued

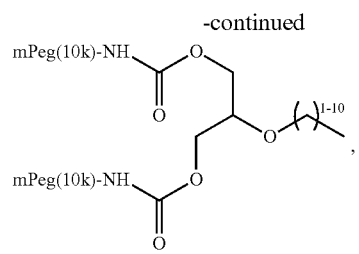
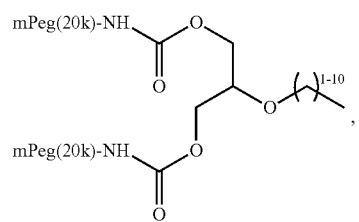
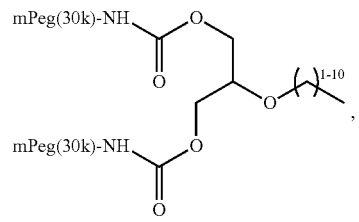
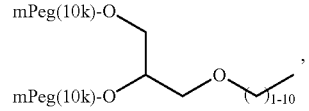
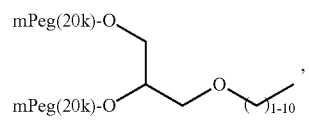
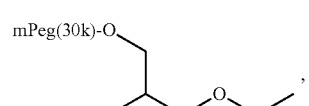
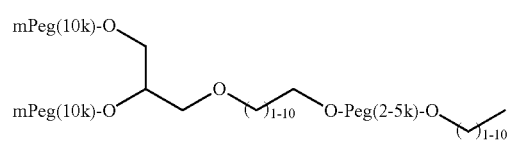
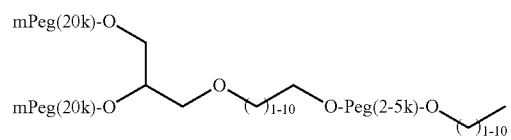
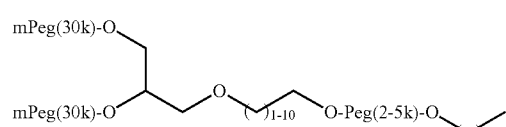

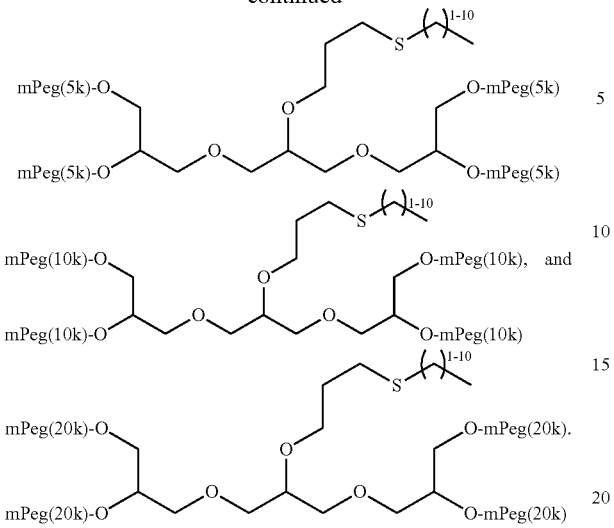

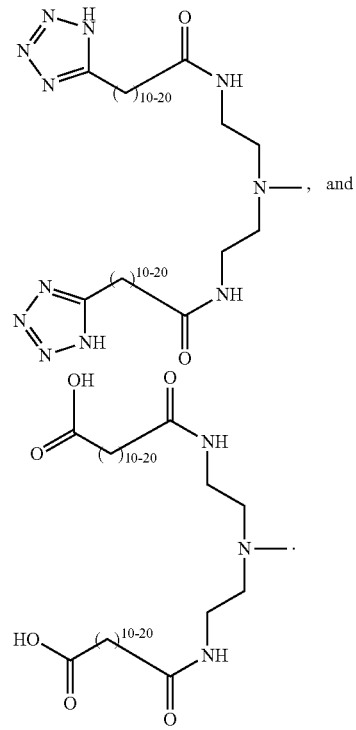

Embodiment 141: A compound according to any of embodiments 116 to 135, wherein $R^3$ is selected from Me-$(CH_2)_{12}$—, Me-$(CH_2)_{14}$—, Me—$(CH_2)_{16}$—, Me—$(CH_2)_{18}$—, (5-tetrazolyl)-$(CH_2)_{12}$—, (5-tetrazolyl)-$(CH_2)_{13}$—, (5-tetrazolyl)-$(CH_2)_{14}$—, (5-tetrazolyl)-$(CH_2)_{15}$—, (5-tetrazolyl)-$(CH_2)_{16}$—, (5-tetrazolyl)-$(CH_2)_{17}$—, (5-tetrazolyl)-$(CH_2)_{18}$—, $HO_2C$—$(CH_2)_{14}$—, $HO_2C$—$(CH_2)_{15}$—, $HO_2C$—$(CH_2)_{16}$—, $HO_2C$—$(CH_2)_{17}$—, $HO_2C$—$(CH_2)_{18}$—, (5-tetrazolyl)$_2$CH—$(CH_2)_{14}$—, Embodiment 142: A compound according to embodiment 116 selected from

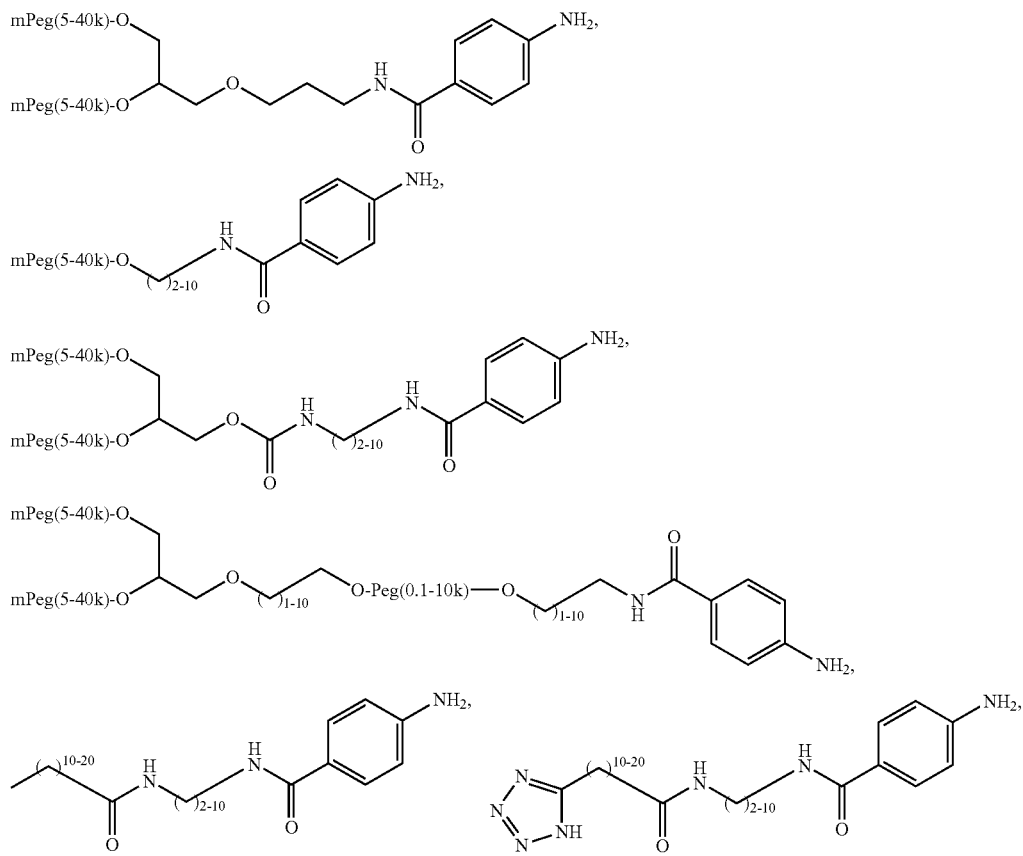

-continued

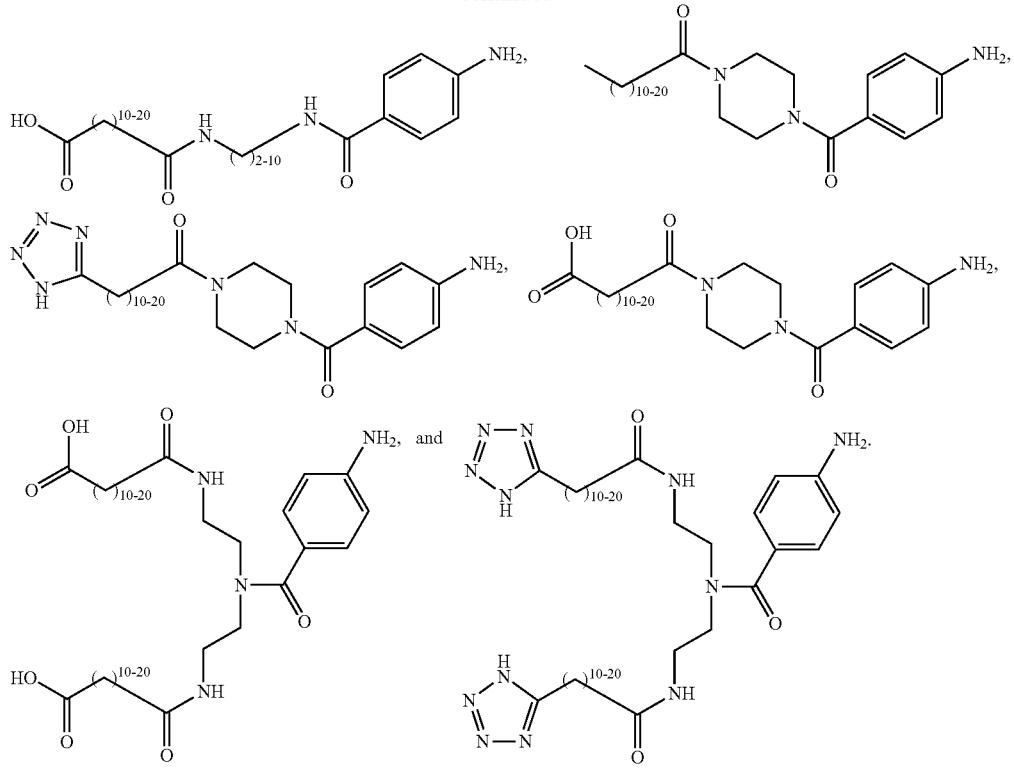

Embodiment 143: Use of a compound according to any of embodiments 116 to 142 for the preparation of conjugated peptide with improved pharmacological properties compared to the unconjugated parent peptide.

Embodiment 144: Use according to embodiment 143, wherein said conjugated peptide is a conjugated antibody or antibody fragment.

Embodiment 145: Use according to embodiment 143, wherein said conjugated peptide is a conjugated growth hormone.

Embodiment 146: Use according to embodiment 145, wherein said growth hormone is a human growth hormone.

Embodiment 147: Use according to any of embodiments 143 to 146, wherein said improved pharmacological property is increased functional in vivo half-life.

Embodiment 148: Use according to 147, wherein the approximate functional in vivo half-life of the peptide has been increased by 1 hour, 2 hours, 3 hours, 4 hours, 5 hours, 10 hours, 1 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Embodiment 149: A compound according to any of embodiments 41 to 61 for use in therapy.

Embodiment 150: A pharmaceutical preparation comprising a compound according to any of embodiments 41 to 61.

Embodiment 151: A method of treating diseases benefiting from an increase in the level of circulating growth hormone, the method comprising the administration of a therapeutically effective amount of a compound according to any of embodiments 41 to 61 or a pharmaceutical preparation according to embodiment 150 to a patient in need thereof.

Embodiment 152: A method according to embodiment 151, wherein said administration is performed every second day or with longer intervals.

Embodiment 153: A method according to embodiment 152, wherein said administration is performed once a week or with longer intervals.

Embodiment 154: A method according to embodiment 153, wherein said administration is performed once a month or with longer intervals.

Embodiment 155: A method according to any of embodiments 151 to 154, wherein said disease is selected from wasting in AIDS patients, GH-deficiency due to a pituitary tumor, and poor growth in children due to GH-deficiency, renal failure, Turner syndrome, and Prader-Willi syndrome.

Embodiment 156: Use of a compound according to any of embodiments 41 to 61 in the manufacture of a medicament for the treatment of a disease benefiting from an increase in the level of circulating growth hormone.

Embodiment 157: Use according to embodiment 156, wherein said disease is selected from wasting in AIDS patients, GH-deficiency due to a pituitary tumor, and poor growth in children due to GH-deficiency, renal failure, Turner syndrome, or Prader-Willi syndrome.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (for instance all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language ("for instance", "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (for instance a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

EXAMPLES

The following abbreviations are used:
Boc: tert-butyloxycarbonyl
Bt: 1-benzotriazolyl
DBU: 1,8-diazabicyclo[5.4.0]undec-7-ene
DCM: dichloromethane, methylenechloride
DIPEA diisopropylethylamine
DMF: N,N-dimethyl formamide
DMSO: dimethyl sulfoxide
EDAC: N-ethyl-N'-(3-dimethylaminopropyl)carbodiimide hydrochloride
Fmoc: 9-fluorenylmethyloxycarbonyl
HBTU: 2-(1H-Benzotriazol-1-yl-)-1,1,3,3 tetramethyluronium hexafluorophosphate
HOBt: N-hydroxybenzotriazole, 1-hydroxybenzotriazole
NMP: N-methylpyrrolidone
HPLC: high pressure liquid chromatography
r.t. room temperature
Su: succinimidyl
TFA: trifluoroacetic acid
TSTU O-(1-succinimidyl)-N,N,N',N'-tetramethyluronium hexafluorophosphate NMR spectra were recorded on Bruker 300 MHz and 400 MHz instruments. HPLC-MS was performed on a Perkin Elmer instrument (API 100).

HPLC-systems from Merck-Hitachi (Hibar™ RT 250-4, Lichrosorb™ RP 18, 5.0 µm, 4.0×250 mm, gradient elution, 20% to 80% acetonitrile in water within 30 min, 1.0 ml/min, detection at 254 nm) and Waters (Symmetry™, C18, 3.5 µm, 3.0×150 mm, gradient elution, 5% to 90% acetonitrile in water within 15 min, 1.0 ml/min, detection at 214 nm) were used.

General Method (A)

The compounds of formula (I) according to this invention may be prepared as follows:

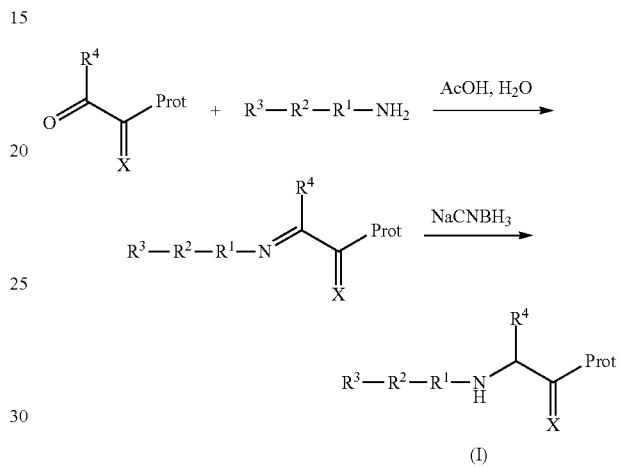

A solution of the peptide-derived aldehyde in a suitable solvent, such as water and an optional dipolar solvent, is added to a solution of the property-modifying group-derived aniline or heteroarylamine in a mixture of acetic acid, water, and an optional dipolar solvent, such as NMP or DMF. The resulting mixture is allowed to stand for some time, for instance between 1 and 70 hours, and an aqueous solution of NaCNBH$_4$, optionally acidified by addition of acetic acid, is added. The resulting mixture is shaken or allowed to stand at room temperature for 1-60 h. Addition of a buffer (pH≥7), followed by standard purification yields the compound of formula (I). The term "dipolar solvent" refers to a solvent with a dielectric constant larger than 6.0.

Example 1

Human Growth Hormone Pegylated at the N-Terminus (Position 1) with mPeg(40 k)

(A): Preparation of Ser-hGH

The Ser-hGH analogue expression plasmid was created on the basis of pNNC13 (Zbasic2mt-D4K-hGH), which expresses the wild type hGH in fusion with Zbasic domain.

(SEQ ID No. 2)
MVDNKFNKERRRARREIRHLPNLNREQRRAPIRSLRDDPSQSANLLAEA

KKLNRAQAPKYRGGSDDDDKSFPTIPLSRLFDNAMLRAHRLHQLAFDTY

QEFEEAYIPKEQKYSFLQNPQTSLCFSESIPTPSNREETQQKSNLELLR

ISLLLIQSWLEPVQFLRSVFANSLVYGASDSNVYDLLKDLEEGIQTLMG

```
RLEDGSPRTGQIFKQTYSKFDTNSHNDDALLKNYGLLYCFRKDMDKVET
FLRIVQCRSVEGSCGF.
```

Additional Ser was inserted in front of Phe, the first amino acid of mature hGH, by QuikChange® XL Site-Directed Mutagenesis Kit from Stratagene with a pair of primes:

```
5' end:                                    (SEQ ID No. 3)
 pNNC13 Ser-F
5'-GGATCAGACGACGACGACAAAagcTTCCCAACCATTCCCTTA
TCC-3' and

3' end: pNNC13 Ser-R                       (SEQ ID No. 4)
5'-GGATAAGGGAATGGTTGGGAAgctTTTGTCGTCGTCGTCTGA
TCC-3'.
```

E. coli BL21(DE3) was transformed by pET11a-Zbasic2mt-D4K-Ser-hGH. A single colony was inoculated into 100 ml LB media with 100 μg/ml Amp and grown at 37° C. When OD600 reached 0.6, the cell culture temperature was reduced to 30° C., and the cells were induced with 1 mM IPTG for 4 hours at 30° C. The bacteria cells were harvested by centrifugation at 3000 g for 15 min (Eppendorf centrifuge 5810R). The cell pellet was resuspended in cell lysis buffer (25 mM $Na_2HPO_4$ 25 mM $NaH_2PO_4$ pH 7, 5 mM EDTA, 0.1% Triton X-100), and the cells were disrupted by cell disruption at 30 kpsi (Constant Cell Disruption Systems). The lysate was clarified by centrifugation at 10000 g for 30 min. The supernatant was saved and used for purification, while the pellet was discarded.

Zbasic2mt-D4K-Ser-hGH was purified on SP-Sepharose using a step gradient elution (buffer A: 25 mM $Na_2HPO_4$ 25 mM $NaH_2PO_4$ pH 7; buffer B: 25 mM $Na_2HPO_4$ 25 mM $NaH_2PO_4$ pH 7, 1 M NaCl). The protein was subsequently cleaved using enteropeptidase for the release of Ser-hGH. Ser-hGH was further purified on a Butyl Sepharose 4FF column to separate the product from the Zbasic2mt-D4K domain and Enteropeptidase (buffer A: 100 mM Hepes pH 7.5; buffer B: 100 mM Hepes pH 7.5, 2 M NaCl, a linear gradient was used). The final product of Ser-hGH was buffer exchanged and lyophilized from 50 mM $NH_4HCO_3$, pH 7.8.

(B) 4-(Boc-Amino)benzoyl mPeg(40 k)

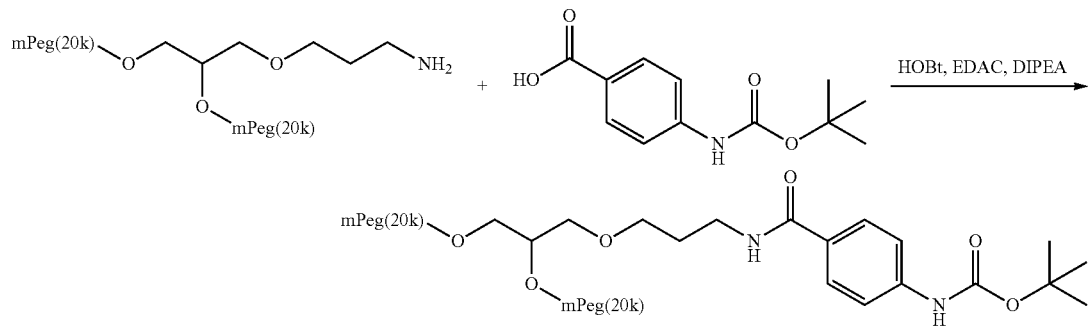

To a solution of mPeg(40 k)-amine (GL2-400PA from NOF Corporation; 5.0 g, 0.125 mmol) in DCM (40 ml) were added 4-Boc-aminobenzoic acid (0.31 g, 1.31 mmol), HOBt hydrate (0.25 g, 1.63 mmol), EDAC (0.44 g, 2.30 mmol), and finally DIPEA (2.0 ml). After stirring at room temperature for 70 h, aminomethyl polystyrene (5 g; approx 1 mmol/g) was added. After stirring for 3 h the mixture was filtered, the polystyrene was washed with DCM, the combined filtrates were concentrated, and the product precipitated by addition of $Et_2O$. Dissolution in DCM, precipitation with $Et_2O$ and filtration was repeated twice. The solid was dissolved in DCM, and an acidic ion exchange resin (Amberlyst 15; 10 g, washed with DCM+MeOH) was added. The mixture was stirred for 0.5 h, filtered, and the product isolated from the filtrate by precipitation with $Et_2O$. Drying under reduced pressure yielded 5 g of the title compound.

(C) 4-Aminobenzoyl mPeg(40 k)

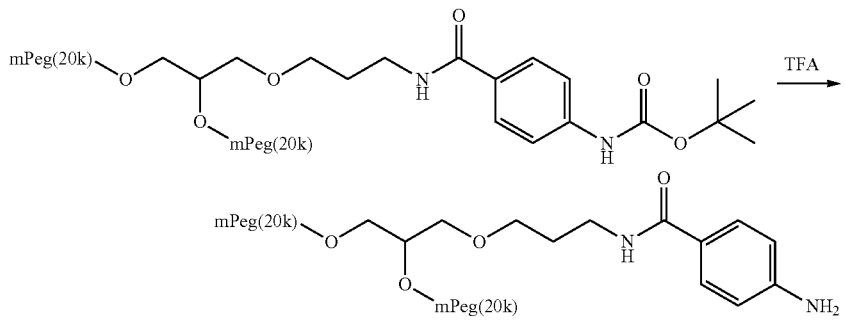

To 4-(Boc-amino)benzoyl mPeg(40 k) (100 mg, 2.5 μmol) were added DCM (10 ml) and TFA (10 ml). After 0.5 h the mixture was concentrated, and the residue coevaporated twice with EtOH. After drying in vacuum overnight the residue was transferred with DCM to a smaller vial, concentrated, and dissolved in water (0.66 ml)+AcOH (0.66 ml). This solution was used for the pegylation of oxidized Ser-hGH.

(D) Oxidation of Ser-hGH to glyoxalyl-hGH

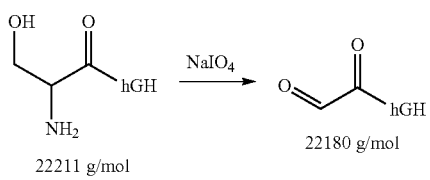

The following solutions were prepared:
Buffer A: triethanolamine (270 mg, 1.8 mmol), 3-methylthiopropanol (580 mg, 5.46 mmol), water (40 ml).
Buffer B: 3-methylthiopropanol (1.2 g)+water (80 ml).
Periodate: NaIO$_4$ (48.1 mg, 0.225 mmol)+water (1.0 ml).

SerhGH (50 mg, 2.3 μmol) was dissolved in buffer A (5.0 ml), and the periodate solution (0.5 ml) was added. After standing at room temperature for 20 min the mixture was transferred to a dialysis tube (Amicon; cut-off 5000), and dialyzed four times with buffer B. The residue was diluted with buffer B to 0.6 ml, and NMP (0.6 ml) was added.

(E) Reductive Amination of Oxidized Ser-hGH with 4-aminobenzoyl mPeg(40 k)

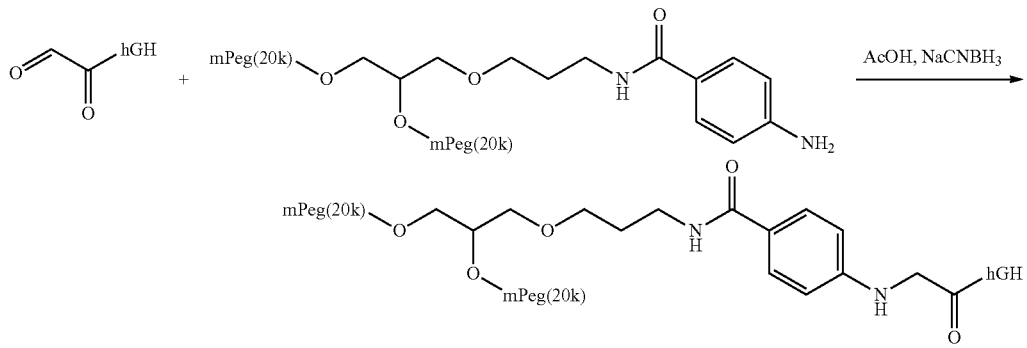

The solution of oxidized Ser-hGH in water and NMP was added immediately after its preparation to the solution of 4-aminobenzoyl mPeg(40 k), and the resulting mixture was slowly rotated at room temperature. After 1 h NaCNBH$_3$ (100 μl of a solution of 20 mg NaCNBH$_3$ and 15 μl AcOH in 0.5 ml water) was added. The mixture is kept at room temperature in the dark. After 42 h the mixture was added in portions to a mixture of triethanolamine (2 g) and water (4 ml). Purification by chromatography yielded the title compound.

Example 2

Human Growth Hormone Pegylated at Position 141 with mPeg(40 k)

(A) Transamination of hGH with 1,3-diamino-2-propanol

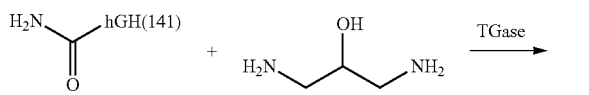

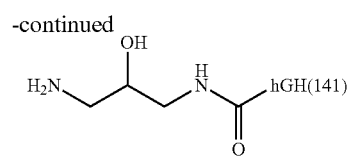

hGH (200 mg, 9 μmol) was dissolved in a phosphate buffer (50 mM, pH 8.0, 14 ml). The resulting solution was mixed with a solution of 1,3-diaminopropan-2-ol (378 mg, 4 mmol) in phosphate buffer (50 mM, 1 ml, pH 8.0) and the pH was adjusted to 8.0 with dilute hydrochloric acid. A solution of transglutaminase (TGase, 18 mg, ~40 U) dissolved in phosphate buffer (50 mM, pH 8.0, 1 ml) was added and the volume was adjusted to 20 ml by addition of phosphate buffer (50 mM, pH 8.0), what led to a concentration of 1,3-diaminopropan-2-ol of 0.2 M. The resulting solution was incubated for 4 h at 37° C.

The temperature was then lowered to room temperature and N-ethylmaleimide was added to a final concentration of 1 mM. After 1 h the mixture was diluted with 10 volumes of tris buffer (50 mM, pH 8.5).

The solution was applied to a MonoQ 10/100 GL column (Amersham Biosciences cat. No. 17-5167-01) preequilibrated with eluant A (50 mM tris, pH 8.5). Elution was performed at a flow of 2.5 ml/min with a gradient of 0% to 100% of eluant B (50 mM tris, 0.2 M NaCl, pH 8.5) in eluant A over 63 min. Fractions were collected based on UV absorption at 280 nm and Maldi-Tof analysis was performed on selected fractions. The fractions corresponding to the largest peak giving the expected molecular weight according to Maldi-Tof mass spectrometry were pooled. This pool contained a mixture of hGH and N$^{\in 141}$—(2-hydroxy-3-aminopropyl) hGH in a ratio 60:40, as determined by CE; method A, and by peptide mapping experiments as described in WO2005070468.

(B) Oxidation of hGH Transaminated with 1,3-diamino-2-propanol

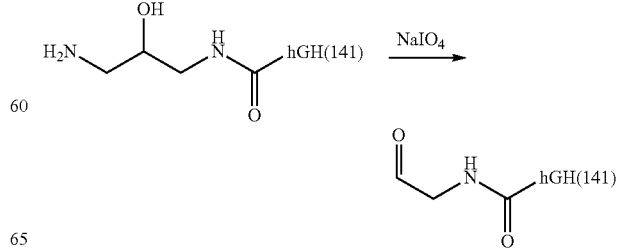

The following solutions were prepared:
Buffer B: 3-methylthiopropanol (1.2 g+water (80 ml).
Periodate: NalO$_4$ (48.1 mg, 0.225 mmol)+water (1.0 ml).

To a solution of hGH transaminated with 1,3-diamino-2-propanol (55 mg (2.5 µmol) transaminated +45 mg unmodified hGH) in a triethanolamine-buffer (4.7 ml) was added 3-methylthiopropanol (70 µl) and then the periodate solution (0.55 ml). After 20 min the mixture was diluted with buffer B and dialyzed 4 times with buffer B. The residue was diluted with buffer B to 0.6 ml and distributed equally into two vials.
(C) Reductive Amination of Oxidized, Transaminated hGH with 4-aminobenzoyl mPeg(40 k)

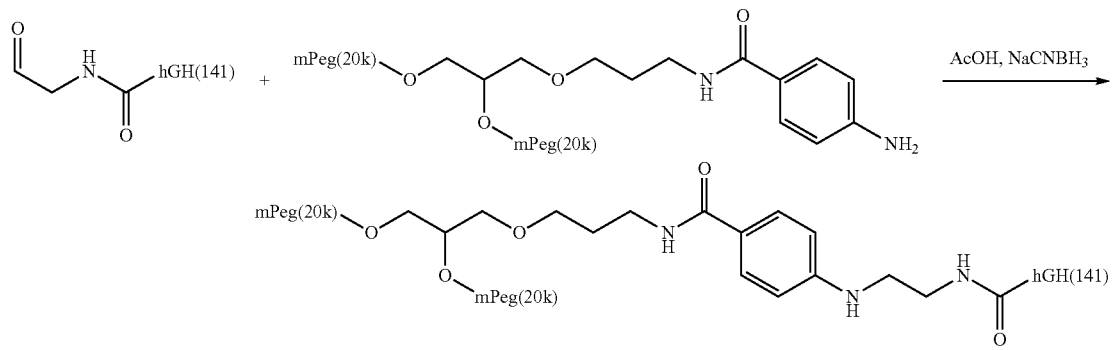

To 4-(Boc-amino)benzoyl mPeg(40 k) (75 mg, 1.88 µmol) was added DCM (10 ml) and TFA (10 ml). After 30 min the mixture was concentrated, and the residue coevaporated twice with EtOH. After drying overnight in vacuo the residue was redissolved in a mixture of water (0.5 ml) and AcOH (0.5 ml, 8.3 mmol).

The content of one vial of oxidized, transaminated hGH (see (B)) was diluted with NMP (0.3 ml) and added to the PEG solution. One hour later the NaCNBH$_3$-solution (0.05 ml of a solution of NaCNBH$_3$ (22 mg, 0.35 mmol; Mwt: 62.8 g/mol) dissolved in water (0.5 ml; c=700 mM) and AcOH (0.015 ml); this solution was prepared just before use) was added. After 66 h the mixture was neutralized by addition to a mixture of triethanolamine (1.7 g, 11.4 mmol) and water (2 ml), and the product was purified by chromatography; 9 mg of the title compound was obtained.

Pharmacological Methods

Assay (I) BAF-3 GHR Assay to Determine Growth Hormone Activity

The BAF-3 cells (a murine pro-B lymphoid cell line derived from the bone marrow) were originally IL-3 dependent for growth and survival. IL-3 activates JAK-2 and STAT which are the same mediators GH is activating upon stimulation. After transfection of the human growth hormone receptor the cell line was transformed into a growth hormone-dependent cell line. This clone could be used to evaluate the effect of different growth hormone samples on the survival of the BAF-3 GHR.

The BAF-3 GHR cells were grown in starvation medium (culture medium without growth hormone) for 24 h at 37° C., 5% CO$_2$.

The cells were washed and resuspended in starvation medium and seeded in plates. 10 µl of growth hormone compound or human growth hormone in different concentrations or control was added to the cells, and the plates were incubated for 68 h at 37° C., 5% CO$_2$.

AlamarBlue® was added to each well and the cells were incubated for further 4 h. AlamarBlue® is a redox indicator, which is reduced by reactions innate to cellular metabolism and, therefore, provides an indirect measure of viable cell number.

Finally, the metabolic activity of the cells was measured in a fluorescence plate reader. The absorbance in the samples was expressed in % of cells not stimulated with growth hormone compound or control, and from the concentration-response curves the activity (amount of a compound that stimulates the cells with 50%) could be calculated.

The data for the compounds described in the examples may be found in Table 1.

TABLE 1

Relative in vitro potency of different hGH derivatives in the BAF hGH-receptor (hGH-R) assay.

| Compound | EC50 (nM) | Ratio [EC50 compound/ EC50 hGH] | n |
| --- | --- | --- | --- |
| hGH (LUOS079) | 0.02 ± 0.005 | 1 (defined) | 3 |
| compound of example 1 | 0.23 ± 0.022 | 10 ± 1 | 4 |
| compound of example 2 | 0.42 ± 0.05 | 19 ± 3 | 4 |

Values are expressed as Mean ± SD

Assay for Determining In Vitro Stability

Solutions of compounds of the invention in various buffers are incubated at 20-40° C. for 1 d to 30 d. Samples are analyzed by HPLC and mass spectrometry, to determine the extent and type of degradation as function of buffer, temperature and time.

In Vivo Dose-Response Study in Hypophysectomised Sprague Dawley Rats

The in vivo dose-response relationship of the compound of example 2 was studied in hypophysectomised male Sprague Dawley rats. The hypophysectomised rat is a well known and recognised animal model of growth hormone deficiency, where no production of growth hormone occurs after the surgical removal of the pituitary gland. This also leads to low circulating levels of insulin-like growth factor-1 (IGF-1) another important clinical feature of growth hormone deficiency in humans.

The hypophysectomy was performed on 4 week old male rats weighing 90-100 g. The animals entered the study 3-4 weeks after the surgery weighing 100-110 g. Animals with a body weight gain of more than 10% during the 3-4 weeks after surgery were not allowed to enter the study.

Sixty hypophysectomised Sprague Dawley rats were randomly allocated to six dosing groups with ten animals in each group. One group received vehicle only and served as an untreated control group. The remaining five groups received 1, 5, 15, 50 and 150 nmol compound of example 2 respectively as a single subcutaneous dose in the neck. The body weight was measured daily between 8-10 am for one week. The data are presented as gain in body weight compared to the day of dosing (Day 0) for 7 days and is presented in FIG. 1.

The invention claimed is:

1. A conjugated peptide according to formula (I)

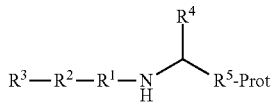

(I)

wherein

Prot is a peptide-derived radical, wherein said peptide-derived radical formed by the formal removal of a hydrogen atom from an amino group (—NH$_2$) of said peptide, $R^1$ is arylene or a heteroarylene, optionally substituted with a $C_{1-6}$-alkyl, halogen, cyano, nitro, hydroxyl, carboxyl, or aryl group;

$R^2$ is a linker comprising the diradical C(=O)—NH—, and $R^3$ is a property-modifying group;

$R^4$ is hydrogen or $C_{1-6}$-alkyl;

$R^5$ is —CH$_2$— or —C(=O)—, or pharmaceutically acceptable salts, thereof.

2. A compound according to claim 1, wherein $R^1$ is a $C_{6-8}$-arylene, a $C_{12-18}$-arylene or a $C_{5-18}$-heteroarylene, optionally substituted with a $C_{1-6}$alkyl, halogen, cyano, nitro, hydroxyl. carboxyl, or aryl group.

3. A compound according to claim 1, wherein $R^2$ is —C(=O)—NH—.

4. A compound according to claim 1, wherein $R^3$ is a linear or branched polyethylene glycol (PEG), poloxamer, poly(lactic acid), poly(lactide)-glycolide copolymer, oligosaccharide, peptides, proteins, or combinations thereof, optionally substituted with acidic or negatively charged functional groups, with basic or cationic functional groups, or with combinations thereof.

5. A compound according to claim 4, wherein $R^3$ is a linear or branched polyethylene glycol of a molecular weight of 5-60 kDa.

6. The peptide radical of $R^5$-Prot in the conjugated peptide according to claim 1, derived from a peptide-derived aldeyde or ketone of formula (A):

$$R^6—C(=O)—R^5\text{-Prot,} \qquad (A)$$

wherein, $R^5$ is —CH$_2$— or C(=O)—, and $R^6$ is hydrogen or an optionally substituted α-carbon atom.

7. A compound according to claim 6, wherein $R^6$ is hydrogen, $C_{1-6}$-alkyl or $C_{1-6}$-cycloalkyl.

8. A compound according to claim 1, wherein Prot is a peptide-derived radical generated by the formal removal of a hydrogen atom from an amino group (—NH$_2$) of a peptide or protein, and wherein said amino group is the N-terminal amino group of the peptide, a side-chain amino group of lysine residue in the peptide, or a side-chain amino group of glutamine or asparagine (CONH2) residue in the peptide.

9. A compound according to claim 1, wherein Prot is a growth hormone-derived radical.

10. A pharmaceutical preparation comprising a compound according to claim 9.

11. A method of treating diseases benefiting from an increase in the level of circulating growth hormone, the method comprising the administration of a therapeutically effective amount of a compound according to claim 9 to a subject in need thereof, wherein said disease is growth hormone deficiency.

* * * * *